(12) United States Patent
Watanabe et al.

(10) Patent No.: US 9,145,432 B2
(45) Date of Patent: *Sep. 29, 2015

(54) COMPOUNDS USEFUL IN VARIOUS FIELDS OF A LUBRICANT

(71) Applicant: FUJIFILM Corporation, Minato-ku (JP)

(72) Inventors: Saisuke Watanabe, Minami-ashigara (JP); Hiyoku Nakata, Minami-ashigara (JP); Ken Kawata, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 134 days.

This patent is subject to a terminal disclaimer.

(21) Appl. No.: 14/020,060

(22) Filed: Sep. 6, 2013

(65) Prior Publication Data

US 2014/0012028 A1    Jan. 9, 2014

Related U.S. Application Data

(62) Division of application No. 12/935,151, filed as application No. PCT/JP2009/056367 on Mar. 27, 2009, now Pat. No. 8,552,213.

(30) Foreign Application Priority Data

Mar. 28, 2008  (JP) ................................. 2008-087957
Mar. 28, 2008  (JP) ................................. 2008-087958
Nov. 26, 2008  (JP) ................................. 2008-301654

(51) Int. Cl.

| | | |
|---|---|---|
| C07F 9/40 | (2006.01) | |
| C07F 7/18 | (2006.01) | |
| C07C 69/734 | (2006.01) | |
| C07C 311/53 | (2006.01) | |
| C07C 69/708 | (2006.01) | |
| C07C 309/70 | (2006.01) | |
| C07C 69/34 | (2006.01) | |
| C07C 69/36 | (2006.01) | |
| C07C 69/38 | (2006.01) | |
| C07C 69/40 | (2006.01) | |
| C07C 69/42 | (2006.01) | |
| C07C 69/44 | (2006.01) | |
| C07C 69/60 | (2006.01) | |
| C07C 69/63 | (2006.01) | |
| C07C 69/76 | (2006.01) | |
| C07C 69/80 | (2006.01) | |
| C07C 69/82 | (2006.01) | |
| C07C 217/08 | (2006.01) | |

(Continued)

(52) U.S. Cl.
CPC .............. *C07F 9/4071* (2013.01); *C07C 69/34* (2013.01); *C07C 69/36* (2013.01); *C07C 69/38* (2013.01); *C07C 69/40* (2013.01); *C07C 69/42* (2013.01); *C07C 69/44* (2013.01); *C07C 69/60* (2013.01); *C07C 69/63* (2013.01); *C07C 69/708* (2013.01); *C07C 69/734* (2013.01); *C07C 69/76* (2013.01); *C07C 69/80* (2013.01); *C07C 69/82* (2013.01); *C07C 217/08* (2013.01); *C07C 271/12* (2013.01); *C07C 271/66* (2013.01); *C07C 307/02* (2013.01); *C07C 309/65* (2013.01); *C07C 309/70* (2013.01); *C07C 311/53* (2013.01); *C07F 7/0852* (2013.01); *C07F 7/0854* (2013.01); *C07F 7/18* (2013.01); *C07F 9/1411* (2013.01); *C10M 129/78* (2013.01); *C10M 2203/1006* (2013.01); *C10M 2205/0285* (2013.01); *C10M 2207/1265* (2013.01); *C10M 2207/283* (2013.01); *C10M 2207/2835* (2013.01); *C10M 2207/30* (2013.01); *C10M 2215/1026* (2013.01); *C10M 2215/2203* (2013.01); *C10N 2220/022* (2013.01); *C10N 2230/06* (2013.01); *C10N 2240/042* (2013.01); *C10N 2240/10* (2013.01); *C10N 2250/10* (2013.01); *C10N 2250/16* (2013.01)

(58) Field of Classification Search
None
See application file for complete search history.

(56) References Cited

U.S. PATENT DOCUMENTS

| 4,772,651 A | 9/1988 | Dunski |
|---|---|---|
| 5,898,023 A | 4/1999 | Francisco et al. |

(Continued)

FOREIGN PATENT DOCUMENTS

| JP | 3-169685 A | 7/1991 |
|---|---|---|
| JP | 11-158482 A | 6/1999 |

(Continued)

OTHER PUBLICATIONS

International Search Report (PCT/ISA/210) dated on Jul. 7, 2009.
Written Opinion (PCT/ISA/237) dated on Jul. 7, 2009.
Brent Vernon et al., "Water-borne, in situ crosslinked biomaterials from phase-segregated precursors", Journal of Biomedical Materials Research, Part A, 2003, 64A, (3), pp. 447-456.

(Continued)

*Primary Examiner* — Kamal Saeed
(74) *Attorney, Agent, or Firm* — Buchanan, Ingersoll & Rooney PC

(57) ABSTRACT

A compound represented by following formula (I): A-L-{$D^1$-(E)$_q$-$D^2$-(B)$_m$—$Z^1$—R}$_p$. In the formula, A represents a p-valent chain or cyclic residue; L represents a single bond or a divalent linking group; p represents an integer of 2 or more; $D^1$ represents a carbonyl group (—C(=O)—) or a sulfonyl group (—S(=O)$_2$—); $D^2$ represents a carbonyl group (—C(=O)—), a sulfonyl group (—S(=O)$_2$—), a carboxyl group (—C(=O)O—), a sulfonyloxyl group (—S(=O)$_2$O—), a carbamoyl group (—C(=O)N(Alk)-) or a sulfamoyl group (—S(=O)$_2$N(Alk)-); E represents a divalent group; and R represents a hydrogen atom, a substituted or non-substituted $C_8$ or longer alkyl group, a perfluoroalkyl group or a trialkylsilyl group.

5 Claims, 26 Drawing Sheets

(51) Int. Cl.
  *C07C 271/12* (2006.01)
  *C07C 271/66* (2006.01)
  *C07C 307/02* (2006.01)
  *C07C 309/65* (2006.01)
  *C07F 7/08* (2006.01)
  *C07F 9/141* (2006.01)
  *C10M 129/78* (2006.01)

(56) References Cited

U.S. PATENT DOCUMENTS

| | | | |
|---|---|---|---|
| 8,524,644 B2 * | 9/2013 | Kawata et al. | 508/459 |
| 2006/0148897 A1 | 7/2006 | Vernon et al. | |
| 2007/0276121 A1 | 11/2007 | Westergom et al. | |
| 2011/0034357 A1 | 2/2011 | Kawata et al. | |
| 2011/0104052 A1 | 5/2011 | Barnett et al. | |

FOREIGN PATENT DOCUMENTS

| | | | |
|---|---|---|---|
| JP | 2002-507657 A | 3/2002 | |
| JP | 2002-530476 A | 9/2002 | |
| JP | 2005-36223 A | 2/2005 | |
| JP | 2005-516110 A | 6/2005 | |
| JP | 2006-257383 A | 9/2006 | |
| JP | 2006-328127 A | 12/2006 | |
| JP | 2007-92055 A | 4/2007 | |
| WO | WO 99/49004 A1 | 9/1999 | |
| WO | WO 00/29521 A1 | 5/2000 | |
| WO | WO 2004/024237 A2 | 3/2004 | |

OTHER PUBLICATIONS

Notification Concerning Transmittal of International Preliminary Report on Patentability (Form PCT/IB/326) issued Oct. 7, 2010 by the International Bureau of WIPO in corresponding International Patent Application No. PCT/JP2009/056367.

Notification of Transmittal of Translation of the International Preliminary Report on Patentability (Form PCT/IB/338) issued Nov. 18, 2010 by the International Bureau of WIPO in corresponding International Patent Application No. PCT/JP2009/056367.

Japanese and English versions of the International Preliminary Report on Patentability (Form PCT/IB/373) and the Written Opinion of the International Searching Authority (Form PCT/ISA/237) issued Nov. 9, 2010 by the International Bureau of WIPO in corresponding International Patent Application No. PCT/JP2009/056367.

Notification Concerning Transmittal of International Preliminary Report on Patentability (Form PCT/IB/326) issued Oct. 7, 2010 by the International Bureau of WIPO in International Patent Application No. PCT/JP2009/056358.

Notification of Transmittal of Translation of the International Preliminary Report on Patentability (Form PCT/IB/338) issued Nov. 18, 2010 by the International Bureau of WIPO in International Patent Application No. PCT/JP2009/056358.

Japanese and English versions of the International Preliminary Report on Patentability (Form PCT/IB/373) and the Written Opinion of the International Searching Authority (Form PCT/ISA/237) issued Nov. 9, 2010 by the International Bureau of WIPO in International Patent Application No. PCT/JP2009/056358.

Office Action issued in corresponding Japanese Patent Application No. 2009-079940 dated Jul. 5, 2013 with English translation.

Office Action issued in corresponding Japanese Patent Application No. 2009-079652 dated Jul. 5, 2013 with English translation.

* cited by examiner

COMPOUNDS USEFUL IN VARIOUS FIELDS OF A LUBRICANT

The present application is a Divisional Application of U.S. application Ser. No. 12/935,151, filed Sep. 28, 2010, which is the National Stage of International Application No. PCT/JP2009/056367, filed Mar. 27, 2009, and claims foreign priority to Japanese Application Nos. 2008-087957 and 2008-087958, filed Mar. 28, 2008, and Japanese Application No. 2008-301654, filed Nov. 26, 2008, the entire contents of each of which are incorporated by reference herein.

TECHNICAL FIELD

The present invention relates to a novel compound. The compound of the invention is useful for various technical fields inclusive of technical fields of a lubricant.

BACKGROUND ART

For the purposes of reducing a coefficient of friction and suppressing wear in various friction-sliding places, lubricating oils have been used in every industrial machine.

In general, current lubricating oils are constituted so as to form a fluid film in a sliding gap under a mild friction condition (fluid lubrication condition) and to form a semi-solid coating film at a frictional interface under a severe friction condition (boundary lubrication condition). That is, the current lubricating oils contain a low-viscosity oil (namely, a base oil) capable of revealing a low coefficient of friction and a chemical which for the purpose of preventing direct contact between interfaces to be caused after the low-viscosity base oil has been broken under a sever friction condition, is able to react with an interface thereof (for example, an iron interface) to form a tough and soft boundary lubricating film capable of imparting a low coefficient of friction. Though the chemical is dissolved in the base oil, it is accumulated with time at an interface thereof due to the reaction with an interface raw material (in general, steel). However, at the same time, the chemical also reacts with the majority of the face which is not directly related to sliding, and accumulation occurs, whereby the valuable chemical is consumed. In addition, even when the chemical is consumed, the base oil does not vanish but actually remains as various decomposition products; and in many cases, such accelerates deterioration of the lubricating oil per se. Moreover, the boundary lubricating film per se formed by the reaction of the chemical is also peeled off by friction-sliding under a severe condition, and the boundary substrate per se is also peeled off; and they are floated or deposited (sludged) together with the foregoing reaction decomposition products, thereby impairing lubricating ability of the lubricating oil and causing a factor in deteriorating its expected performance. In order to prevent this matter, in general, an antioxidant, a dispersant, a cleaning agent and the like are added to a lubricant (Patent Document 1).

In the light of the above, in the majority of current lubricating oils, for the purpose of reducing the friction under an extremely severe condition (boundary lubrication condition) and also the purposes of reducing and inhibiting side effects of the added chemical, a new chemical is further added. Moreover, for the purpose of reducing a lowering of the lubricating function to be caused due to fine worn powders formed from the interface per se by the wear and decomposition floats of the chemical, a new chemical is further added. And since functions of various chemicals are related to each other in the lubricating oil, it is inevitable and unavoidable that a period of time when the lubricating oil can function as a whole and exhibit the best lubricating effect becomes short due to exhaustion and deterioration of the respective chemicals. It may be said that this is a vicious cycle of a certain kind. In consequence, it is not easy to greatly improve the composition for the purpose of improving performances of current lubricating oils.

However, all of the foregoing compounds called "chemical" are ones containing an element reactive with the iron interface, and furthermore, substances formed through a reaction between such a compound and iron have ability to reduce friction and wear thereof. The element which is essential for the lubrication is phosphorus, sulfur or a halogen and furthermore, is zinc or molybdenum working competitively and complementarily. The former three are distinctly an environmentally hazardous element, and release thereof into the air even as an exhaust gas must be utterly avoided.

In addition, lubricating oils to be used for internal combustion engines, automatic transmissions and the like are required to be made low in viscosity for the purpose of achieving fuel saving, and at the same time, from the viewpoints of effective utilization of resources in recent years, reduction of waste oil, cost reduction of lubricating oil user and the like, a requirement for realization of long drain of a lubricating oil is increasing more and more. In particular, following high performances of internal combustion engines, high outputs, severe driving conditions and the like, lubricating oils for internal combustion engine (engine oils) are being required to have higher performances.

However, in conventional lubricating oils for internal combustion engine, in order to ensure heat or oxidation stability, it is generally conducted to use a highly refined base oil such as hydrocracked mineral oils, etc., or a high-performance base oil such as synthetic oils, etc. and blend the base oil with a sulfur-containing compound having peroxide decomposing ability such as zinc dithiophosphate (ZDTP), molybdenum dithiocarbamate (MoDTC), etc., or an ashless antioxidant such as such as phenol based or amine based antioxidants, etc. However, it may not be said that the heat or oxidation stability by itself is always sufficient. Moreover, though it is possible to improve the heat or oxidation stability to some extent by increasing the blending amount of the antioxidant, there is naturally a limit in an effect for enhancing the heat or oxidation stability according to this technique.

And from the viewpoint of an environmental issue such as a reduction of emission of carbon dioxide, etc., the engine oils are required to be reduced in the content of sulfur or phosphorus for the purposes of enhancing fuel-saving performance and durability and keeping catalytic ability for cleaning an exhaust gas. On the other hand, in diesel engines in recent years, though an emission control mechanism of particulate matter, such as a diesel particulate filter (DPF), etc., is started to be installed, diesel engine oils are required to realize a low ash from the standpoint of an issue of plugging of the mechanism. The realization of a low ash of engine oils means a reduction of a metallic cleaning agent, and it is an extremely important problem to ensure diesel engine cleaning properties to be kept by blending a large amount of a metallic cleaning agent or an ashless dispersant, in particular, cleaning properties of a top ring groove with a high heat load.

When an internal combustion engine is taken as an example, the foregoing lubrication is concerned with lubrication of portions other than a combustion chamber and a lubricating composition. However, as for the lubrication of the combustion chamber, there is actually a big problem, too. That is, studies for controlling (preventing or decreasing) a reduction of deposits formed in a fuel introducing port of the combustion chamber, or a reduction of friction and wear to be caused thereby, by trace additives to be added to the fuel have been continued over a period of many years.

In particular, in recent years, from the viewpoint of exhaust gas regulation, it has been becoming essential to realize a low sulfur concentration of a fuel composition. However, there is a concern that according to this, the lubricating properties are lowered, thereby causing a lowering of durability of a valve gear mechanism including cams and valves. Here, it is also driven by necessity to review the conventional element contributing to a reduction of friction and wear.

That is, in order to exhibit efficacy by small amount addition, reactivity with an interface raw material is an essential requirement, and nevertheless an element capable of revealing desired low friction by forming a boundary lubricating film is essential, at the same time, it is required to reduce sulfur, phosphorus and heavy metals, the presence per se of which is problematic. The lubricating oils are a material supporting the current industrial machines themselves, and even if they are not easily displaced, this is the moment at which a composition of lubricating oil and a lubrication mechanism per se as a background thereof must be seriously reviewed by the latest scientific technologies and functional raw material technologies after a lapse of 150 years or more.

At the beginning, while it has been described that "For the purposes of reducing a coefficient of friction and suppressing wear in various friction-sliding places, lubricating oils have been used in every industrial machine", a mission of the lubricating oil itself is to keep and preserve a motor function of machine. Though we make a machine work and utilize it, when the work (action) is taken out (counteraction), friction is inevitably caused at a mutually sliding interface. In order to reduce vigorous wear generated by the friction and prevent a mechanical damage such as seizure, etc. from occurring, it is necessary to ensure a sliding gap, and for that reason, various solid or liquid lubricating films have been applied.

A theoretical analysis of the behavior of such a liquid film in the friction state starts from the matter that the Navier-Stokes equations describing the motion of a viscous fluid in the hydrodynamics were applied to a gap with a narrow Reynolds. In those days, an experimentally verified phenomenon in which a wedge-shaped oil film in a bearing generates a high hydrodynamic pressure was theoretically explained, thereby laying the foundation of the fluid lubrication theory of the day.

According to this theory, in view of the fact that the Sommerfeld number which is utilized as a basic characteristic number of the bearing design is expressed by the following equation, it is noted that a film thickness d of a sliding gap is related to a pressure P, a viscosity $\eta$ ($\rightarrow$ also correlated with a temperature T) and a sliding velocity V. Since the film thickness d itself of the sliding gap accurately depends upon an average roughness Ra of the surface thereof, it may be said that factors relating to breakage of the film thickness d of the sliding gap are the pressure P, the temperature T, the viscosity $\eta$, the average roughness Ra of the surface and the sliding velocity V.

$$\text{Sommerfeld number } S = [\eta(T)*R \text{ (bearing radius)} * V \text{ (velocity)}] / [2\pi P \text{ (pressure)} * d^2 \text{ (gap)}]$$

From the viewpoint of keeping the oil film, as for the factors influencing the gap d, it may be easily analogized that at a high temperature, factors of a reduction of the viscosity of the oil film and an interface roughness are important and that under a high pressure, the pressure and the pressure dependency of the oil film viscosity are naturally important.

In consequence, the history of a technology for keeping a liquid film started from control of the viscosity of a base oil. First of all, in order to prevent breakage, an oil with relatively high viscosity, namely a highly viscous oil is used. However, a machine must start up, and at that time, a high viscosity is disadvantageous. Furthermore, in general, at the start-up time, the temperature is lower than that at the operation time, in most cases, the oil hardly moves because of its extremely high viscosity; and therefore, in a sense of utterly avoiding breakage at the high-temperature time, a high viscosity index oil which is originally low in viscosity was used, and furthermore, a polymer (viscosity index improver) was added to a low-viscosity base oil.

The technology developed in response to severer conditions at a high temperature and under a high pressure is a technology concerning an interface protective film (boundary lubricating film) capable of firmly adhering directly to an interface, in particular an iron interface and having flexibility. Historically, starting from the addition of a soap, inorganic films such as iron chloride, iron sulfide, iron phosphate, etc. were formed; and in recent years, reactive and low-friction organometallic complexes such as Mo-DTC, Zn-DTP, etc. have been developed, and a trace amount thereof is added to a base oil.

Though there were an improvement of viscosity physical properties against the temperature as described previously and a technical development of forming a lubricating film by another method, a technical and simple approach as in the invention, in which a viscosity-pressure modulus is controlled and optimized for the purpose of inhibiting breakage of an oil film while controlling the viscosity against the pressure has not been revealed yet.

However, the theory concerning the viscosity-pressure modulus has been surely established with the times.

As for the friction mechanism, there is known an elastic fluid lubrication mechanism between the foregoing mild fluid lubrication mechanism and severe boundary lubrication mechanism. A theoretical study of this elastic fluid lubrication mechanism started from the study regarding the true contact face shape and the generated pressure, published by Hertz in 1882; established by a summary of the EHL elastic fluid lubrication theory by Petrosevich in 1951; and became a practical theory by an oil film formation theory taking into consideration of elastic deformation by Dowson/Higginson in 1968.

A region where this elastic fluid lubrication mechanism works is a friction region under a high pressure of, for example, several tons per cm$^2$, namely about several hundred MPa. At a glance, though such a condition is severe, in fact, since iron starts to cause elastic deformation within such a pressure range, the area of the true contact face of the iron interface coming into contact with the oil film increases, and the substantial pressure becomes low. That is, within this region, so far as an elastic limit of iron or oil film breakage is not caused, the coefficient of friction does not increases, and it may be said that such a region is a "blessed region" for the sliding interface. Moreover, at the same time, in this region, an oil film made of a general lubricating oil such as mineral oils becomes high in viscosity by about 1,000 times that at the time of atmospheric pressure, but there may be the case where it becomes low in viscosity by only about 500 times depending upon a chemical structure of the raw material. Barus expressed this phenomenon relative to pressure dependency of the viscosity of liquid in terms of the following equation (VII) and exhibited that an increase rate $\alpha$ of viscosity which is inherent in the substance to pressure is related (Non-Patent Document 1).

$$\eta = \eta_0 \exp(\alpha P) \quad \text{(VII)}$$

Here, $\alpha$ represents a viscosity-pressure modulus; and $\eta_0$ represents a viscosity at atmospheric pressure.

Moreover, Doolittle advocated a thought of a free volume model that a viscosity of liquid is determined by a ratio of an occupied volume of molecule occupied in a liquid volume and a free volume generated by thermal expansion (Non-Patent Document 2).

$$\eta = A\exp(BV_0/V_f) \quad (VIII)$$

Here, $\eta$ represents a viscosity; $V_0$ represents an occupied volume of molecule; and $V_f$ represents a free volume.

In comparison between the equation (VIII) of Doolittle and the equation (VII) of Barus, it is noted that the viscosity-pressure modulus $\alpha$ is in inverse proportion to the free volume of molecule. That is, what the viscosity-pressure modulus is small suggests that the free volume of molecule is large. In consequence, it is noted that it is possible to control the pressure dependency of the viscosity of liquid by optimizing a chemical structure of raw material, namely, it is possible to provide a raw material having a lower viscosity than oils constituting current lubricating oils under the same high-load and high-pressure conditions by optimizing the chemical structure. For example, assuming that an oil film of a true contact part is formed by a raw material having a viscosity-pressure modulus $\alpha$ of about a half of that of mineral oils or hydrocarbon based chemical synthetic oils such as poly-$\alpha$-olefins, which are usually used as a lubricating oil, this elastic fluid lubrication region is laid under a milder condition. That is, in usual lubricating oils, even under a high load which is classified into the boundary lubrication region, in view of the fact that a cooling effect by an oil film as well as low pressure and low viscosity of the true contact site is added due to the elastic deformation of the interface and the low-viscosity oil film under a high pressure, it is expected to substantially avoid the boundary lubrication region and realize an ideal lubrication mechanism made of only fluid lubrication.

In recent years, it is disclosed that discotic compounds having a plurality of radially arranged relatively long carbon chains and lubricating oils containing the same (namely, a metallic raw material-free lubricating oil) exhibit a low coefficient of friction in the elastic fluid lubrication region (for example, Patent Documents 2 to 4). Such a discotic compound has a discotic core and side chains radially extending from the discotic core, and it is expected that a sector-shaped free volume can be inevitably ensured in a highly arranged state, too. In consequence, discotic or tabular compounds having radially arranged side chains have many free volumes in common as compared with an occupied volume thereof, and therefore, they exhibit a small viscosity-pressure modulus. That is, it is expected that the viscosity is relatively small even under a high pressure, and lower viscosity and lower friction properties are revealed under a high pressure (Non-Patent Document 3).

However, what is common among these raw materials is the matter that the viscosity thereof is larger by one digit than that of mineral oils and chemical synthetic oils usually used for lubricating oils, and it is absolutely impossible to use a large amount of such a raw material inexpensively in place of low-viscosity base oils.

That is, though the viscosity under a high pressure is defined by the viscosity $\eta_0$ and the viscosity-pressure modulus $\alpha$ as expressed by the foregoing equation (VII), when a low-viscosity base oil is actually used, it already starts to be broken in an elastic fluid lubrication region, and it becomes in a viscosity-free state, namely an elasto-plastic body under a high pressure. It has been elucidated that easiness of breakage of this lubricating oil film is correlated with an agglomerated state of fluid molecules, namely a packing state of lubricating oil molecules and can be evaluated by a product $\alpha P$ of the viscosity-pressure modulus $\alpha$ and the pressure P (Non-patent Document 4).

In general, the lubricating oil film acts as a viscous fluid when the product $\alpha P$ is not more than 13, as a visco-elastic fluid when the product $\alpha P$ is between 13 and 25 and as an elasto-plastic body when the product $\alpha P$ is 25 or more, respectively. In the case where two kinds of lubricating oil films having the same viscosity $\eta$ under a certain pressure P, where a viscosity-pressure modulus is defined as $\alpha_1$ and $\alpha_2$, respectively, and also a normal pressure viscosity is defined as $\eta_1$ and $\eta_2$, respectively, the following equation is established.

$$\ln \eta = \ln \eta_1 + \alpha_1 \cdot P = \ln \eta_2 + \alpha_2 \cdot P$$

In the case of $18 = \alpha_1 \cdot P < \alpha_2 \cdot P = 24$, namely $\alpha_1/\alpha_2 = 18/24$, it is noted that when the pressure P is increased a little more, the film having a viscosity-pressure modulus $\alpha_2$ becomes an elasto-plastic body and is more easily broken even under the same pressure at the same viscosity.

In consequence, even when a base oil having a relatively large $\eta_0$ to such extent that it can be used even in a fluid lubrication region is utilized, since the viscosity-pressure modulus $\alpha$ of an chain hydrocarbon such as mineral oils constituting a base oil is large, there is eventually a tendency that the viscosity $\eta$ under a high pressure becomes large, and it has been considered that neither base oil having a visco-elastic fluid region nor organic compound, each of which has a low $\eta_0$ capable of imparting a low coefficient of friction under fluid lubrication and a low $\alpha$ capable of imparting a low coefficient of friction under elastic fluid lubrication at the same time, is present so far.

For the time being, even if a raw material capable of clearing the foregoing restrictions could be developed, taking into consideration necessary conditions of base oils requiring large-amount feed and low costs, it is difficult to provide a raw material satisfying all of them. Therefore, as for engine oils which are essential to be low in viscosity for the purpose of achieving low fuel consumption, it may be considered that there is a background wherein a concept itself for effectively utilizing elastic fluid lubrication was not recognized. It may be said that convergence of the raw material development to a combination of a current low-viscosity based oil and a trace chemical capable of forming a boundary lubricating film as described at the beginning was an inevitable result.

[Patent Document 1] JP-T-2005-516110
[Patent Document 2] JP-A-2006-328127
[Patent Document 3] JP-A-2007-92055
[Patent Document 4] JP-A-2006-257383
[Non-Patent Document 1] C. Barus, *Am. J. Sci.,* 45 (1893), page 87
[Non-Patent Document 2] A. K. Doolittle, *J. Appl. Phys.,* 22 (1951), 1471
[Non-Patent Document 3] Masanori HAMAGUCHI, Nobuyoshi OHNO, Kenji TATEISHI and Ken KAWATA, *Preprint of the International Tribology Conference* (Tokyo, 2005-11), page 175
[Non-Patent Document 4] Nobuyoshi OHNO, Noriyuki KUWANO and Fujio HIRANO, *Junkatsu* (Lubrication), 33, 12 (1988), 922; 929

DISCLOSURE OF THE INVENTION

Problems to be Resolved by the Invention

One object of the invention is to provide a novel compound which is useful in various fields inclusive of technical fields of a lubricant, etc.

Means of Solving the Problems

The means for achieving the objects are as follows.
[1] A compound represented by following formula (Z):

$$A\text{-}L\text{-}\{D^1\text{-}(E)_q\text{-}D^2\text{-}(B)_m\text{—}Z^1\text{—}R\}_p \quad (Z)$$

wherein
A represents a p-valent chain or cyclic residue;
L represents a single bond, an oxy group, a substituted or non-substituted oxymethylene group represented by follow ing formula (A-a), or a substituted or nonsubstituted oxyethyleneoxy group represented by following formula (A-b):

$$—(O—C(Alk)_2)- \quad (A\text{-}a)$$

$$—(O—C(Alk)_2C(Alk)_2O)— \quad (A\text{-}b)$$

Alk represents a hydrogen atom, a $C_1$-$C_6$ alkyl group or a cycloalkyl group;

p represents an integer of 2 or more;

$D^1$ represents a carbonyl group (—C(=O)—) or a sulfonyl group (—S(=O)$_2$—), and each $D^1$ may be the same as or different from every other $D^1$;

$D^2$ represents a carbonyl group (—C(=O)—), a sulfonyl group (—S(=O)$_2$—), a carboxyl group (—C(=O)O—), a sulfonyloxyl group (—S(=O)$_2$O—), a carbamoyl group (—C(=O)N(Alk)-) or a sulfamoyl group (—S($\alpha$O)$_2$N(Alk)-), and each $D^2$ may be the same as or different from every other $D^2$, wherein Alk represents a hydrogen atom, a $C_1$-$C_6$ alkyl group or a cycloalkyl group;

E represents a substituted or nonsubstituted alkylene group, cycloalkylene group, alkenylene group, alkynylene group or arylene group, a divalent heterocyclic aromatic ring group or heterocyclic non-aromatic ring group, a divalent group selected among an imino group, an alkylimino group, an oxy group, a sulfide group, a sulfenyl group, a sulfonyl group, a phosphoryl group and an alkyl-substituted silyl group, or a divalent group composed of a combination of two or more of these groups; q represents an integer of 0 or more; and when q is 2 or more, each E may be the same as or different from every other E;

R represents a hydrogen atom, a substituted or non-substituted $C_8$ or longer alkyl group, a perfluoroalkyl group or a trialkylsilyl group, and each R may be the same as or different from every other R;

B varies depending upon R;

in the case where R represents a hydrogen atom or a substituted or non-substituted $C_8$ or longer alkyl group, B represents a substituted or non-substituted oxyethylene group or a substituted or non-substituted oxypropylene group; plural Bs connecting to each other may be the same as or different from each other; and m represents a natural number of 1 or more;

in the case where R represents a perfluoroalkyl group, B represents an oxyperfluoromethylene group, an oxyperfluoroethylene group or an optionally branched oxyperfluoropropylene group; plural Bs connecting to each other may be the same as or different from each other; and m represents a natural number of 1 or more;

in the case where R represents a trialkylsilyl group, B represents a dialkylsiloxy group in which the alkyl group is selected among a methyl group, an ethyl group and an optionally branched propyl group; each B may be the same as or different from every other B; plural Bs connecting to each other may be the same as or different from each other; and m represents a natural number of 1 or more; and $Z^1$ represents a single bond, a divalent group selected among a carbonyl group, a sulfonyl group, a phosphoryl group, an oxy group, a substituted or non-substituted amino group, a sulfide group, an alkenylene group, an alkynylene group and an arylene group or a divalent group composed of a combination of two or more of these groups.

[2] The compound according to [1], wherein in the formula (Z), A is a residue of pentaerythritol, glycerol, oligo-pentaerythritol, xylitol, sorbitol, inositol, trimethylolpropane, ditrimethylpropane, neopentyl glycol or polyglycerin.

[3] The compound according to [1], wherein in formula (Z), A is a group represented by any of following formulae (AI) to (AIII):

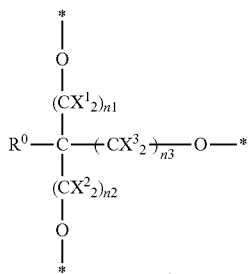

(AI)

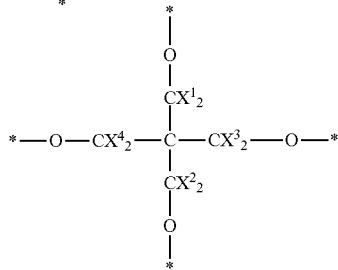

(AII)

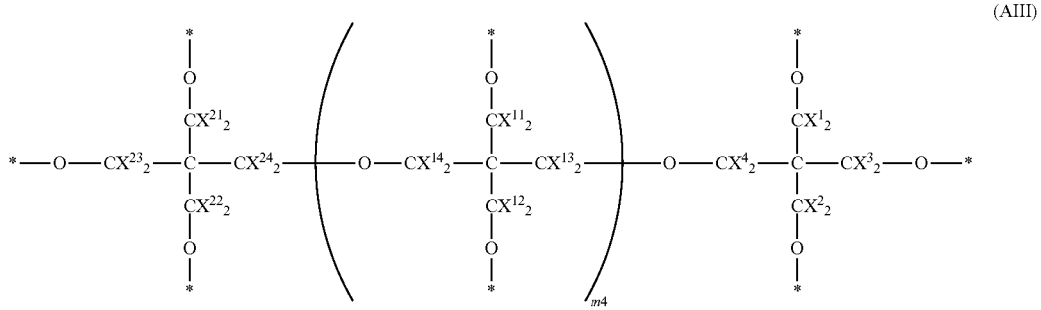

(AIII)

wherein

\* means a bonding site to -L-$D^1$-$(E)_q$-$D^2$-$(B)_m$—$Z^1$—R; C represents a carbon atom; $R^0$ represents a hydrogen atom or a substituent; each of $X^1$ to $X^4$, $X^{11}$ to $X^{14}$ and $X^{21}$ to $X^{24}$ represents a hydrogen atom or a halogen atom and may be the same as or different from every other; each of n1 to n3 represents an integer of from 0 to 5; and m4 represents an integer of from 0 to 2.

[4] The compound according to any one of [1]-[3], wherein in the formula (Z), each —$(B)_m$—$Z^1$—R is a group represented by following formula (ECa), and each —$(B)_m$—$Z^1$—R may be the same as or different from every other —$(B)_m$—$Z^1$—R:

wherein

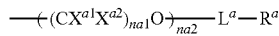
(ECa)

in the formula (ECa), C represents a carbon atom; O represents an oxygen atom; $R^a$ corresponding to R in the formula (Z) represents a substituted or non-substituted $C_8$ or longer alkyl group; $L^a$ corresponding to $Z^1$ in the formula (Z) represents a single bond or a divalent connecting group; each of $X^{a1}$ and $X^{a2}$ represents a hydrogen atom or a halogen atom; na1 represents an integer of from 1 to 4; when na1 is 2 or more, plural $X^{a1}$s and $X^{a2}$s may be the same as or different from each other; and na2 represents a number of from 1 to 35.

[5] The compound according to [4], wherein in formula (Z), $L^a$ corresponding to $Z^1$ is a single bond or a divalent connecting group composed of a combination of one or more members selected among a carbonyl group, a sulfonyl group, a phosphoryl group, an oxy group, a substituted or non-substituted amino group, a thio group, an alkylene group, an alkenylene group, an alkynylene group and an arylene group.

[6] The compound according to any one of [1]-[3], wherein in formula (Z), each —$(B)_m$—$Z^1$—R is a group represented by following formula (ECb), and each —$(B)_m$—$Z^1$—R may be the same as or different from every other —$(B)_m$—$Z^1$—R:

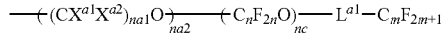
(ECb)

wherein in the formula (ECb), the same symbols as those in the formula (ECa) according to [4] are synonymous, respectively; $L^{a1}$ corresponding to $Z^1$ in the formula (Z) represents a single bond; na2 represents a number of from 0 to 2; nc represents a number of from 1 to 10; m represents a number of from 1 to 12; and n represents a number of from 1 to 3.

[7] The compound according to any one of [1]-[3], wherein in formula (Z), each —$(B)_m$—$Z^1$—R is a group represented by following formula (ECc), and each —$(B)_m$—$Z^1$—R may be the same as or different from every other —$(B)_m$—$Z^1$—R:

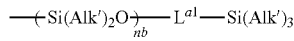
(ECc)

wherein in formula (ECc), the same symbols as those in formula (ECa) according to [4] are synonymous, respectively; each Alk' may be the same as or different from every other Alk' and represents a $C_1$-$C_4$ alkyl group; $L^{a1}$ corresponding to $Z^1$ in the formula (Z) represents a single bond; and nb represents a number of from 1 to 10.

Effect of the Invention

According to the invention, it is possible to provide a novel compound which is useful in various fields inclusive of technical fields of a lubricant, etc.

MODE FOR CARRYING OUT THE INVENTION

The invention is described in detail hereinunder. Note that, in this description, any numerical expressions in a style of " . . . to . . . " will be used to indicate a range including the lower and upper limits represented by the numerals given before and after "to", respectively.

1. Compound Represented by Formula (Z)

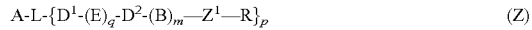
(Z)

In the formula, A represents a p-valent chain or cyclic residue.

A preferred example of A is a residue containing a branched structure in which atoms within the third (γ-position) from the atom (α-position) in A bonding to -L are secondary or more. The compound represented by the formula (Z) containing such A belongs to a compound group expressed as a so-called "starburst shape" or "star shape", and exhibits preferred natures as a lubricant composition or the like.

The compound "having a small increase rate of viscosity by pressure" as described previously is useful in a technical field of lubricant, and it is also described previously that Non-Patent Document 2 discloses that such a nature can be achieved by a compound "having a large free volume as far as possible". An example of the compound "having a large free volume as far as possible" is a compound in which the free volume of plural side chains present in the molecule is large.

When a triphenylene compound is taken as an example for the compound having a discotic structure, for example, in a triphenylene having long-chain alkoxy groups at 2-, 3-, 6-, 7-, 10- and 11-positions, side chains composed of such a long-chain alkoxy group naturally extend radially, and the farther the side chain is from the center starting from the oxygen atom in the alkoxy group, the larger the volume of a space where the side chain can freely move (free volume) is. Even when the subject compound is accumulated in a high density, or it takes a hexagonal closest packing structure of a columnar structure such as a liquid crystal phase or a crystal, a minimal space where the side chain can take a certain movement. This is a significant difference between a discotic molecule and a string-like molecule. When the string-like molecule is uniaxially oriented, the free volume is lost.

Next, a molecule having a structure in which side chains extend equally in four directions against the space centering an SP3 element in exactly a "starburst shape" or "star shape" as in methane, tetramethylsilane, trimethylamine, etc. is considered. In such a molecule, it may be considered that similar to the molecule having a discotic structure, it is theoretically possible to similarly ensure its free volume; however, the actual situation is considerably different. In the discotic molecule as described previously, a discotic nucleus itself ensures a space where a side chain can freely move until a distance of a certain degree from its center, from the first due to an incorruptible nucleus structure thereof, whereas in the "starburst-shaped" or "star-shaped" molecule, a structure in which carbon chains are extended centering the SP3 element directly from this element is taken; and therefore, there is a significant difference therebetween.

For example, in comparison between the position of oxygen of a hexaalkoxytriphenylene as the foregoing discotic compound and the position of oxygen of triethoxylate of trimethylolmethane as the "starburst-shaped" or star-shaped" compound, as schematically below, when approximated in terms of a length of the chain of SP3 carbon, the position of oxygen is corresponding to the position of carbon from approximately the fourth from SP3 carbon of the central nucleus, namely carbon of the epoxy group terminal. At a glance, the latter has a higher degree of freedom; however, when the density increases, and the molecules start to agglomerate, other side chain also comes into a space in the vicinity of each of the side chains, the respective side chains are bent, or the side chains become approximately in a rod-like shape in such a manner of closing an umbrella, thereby possibly reducing the free volume. It may be easily supposed that when the density is actually increased, the state of the side chains will change in such a way.

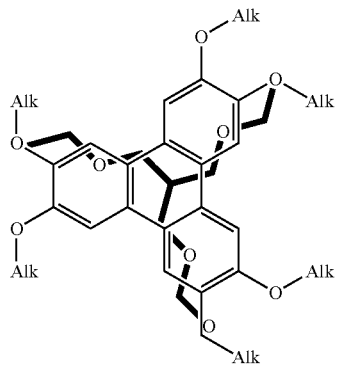

Even in molecules having a nucleus of a non-discotic structure, such as such an SP3 element-containing nucleus, etc., for the purpose of enabling a side chain thereof to ensure a large space volume similar to a side chain of a discotic molecule, the present inventor made extensive and intensive investigations on what structure of the side chain is suitable. As a result, the invention has been accomplished on the basis of the resulting knowledge.

Though the following acetoxytrimethylolmethane is one obtained by converting the triethoxylate of trimethylolmethane into an ester, this structure is a basic structure of fat and oil in the world of lubrication. The fat and oil as referred to herein is a polyol ester of a fatty acid and has a structure in which a lower viscosity-pressure modulus, namely a lower coefficient of friction under a high pressure than that of a mineral oil can be easily revealed.

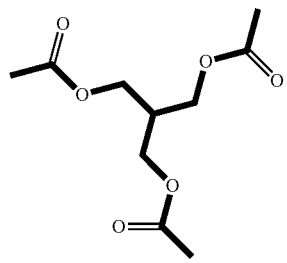

It may be presumed that reasons for this reside in the facts that the rotational barrier energy of C—O in the ester is smaller than that of C—C; and that since electron repulsion and steric repulsion between carbonyl groups are easy to open radially, the free volume can be largely ensured. Certainly, an ester of a polyol tends to be low in friction as compared with an ester of a polycarboxylic acid. It may be considered that this is related to the size of the free volume influencing the whole of side chains of the rotation of C—O.

But, current ester oils are low in friction as compared with mineral oils, a degree of which is, however, not conspicuous so much. Then, the present inventor has made extensive and intensive investigations regarding a lubricating effect of a compound having a carbonyl group in the tip of a further extended side chain and found that the following compound obtained by linking a residue corresponding to succinic acid to trimethylolmethane exhibits a conspicuous friction reducing effect.

This result is revealed in not only a 1,4-dicarbonyl group as in succinic acid but a 1,3-dicarbonyl group, a 1,5-dicarbonyl group interposing oxygen in a center thereof, etc. Moreover, a polyol ester of acylated sarcosinic acid also reveals the same friction reducing effect.

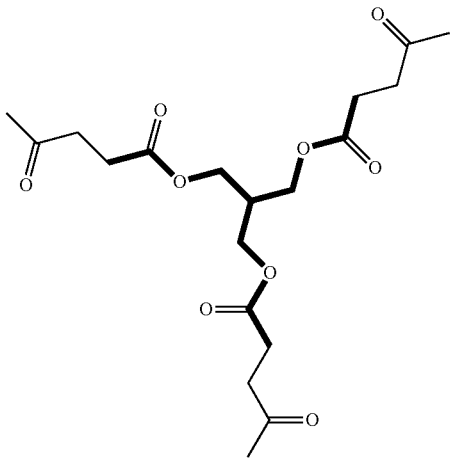

In consequence, the invention is concerned with a compound having a chain or cyclic chemical structure capable of radially arranging side chains and having radially extending side chains linked thereto, and it utilizes a compound capable of ensuring a larger free volume. In order that the side chains may ensure a large free volume, it is preferable to have a chemical structure designed such that the side chains are easy to freely rotate in the vicinity of a bonding site to a central nucleus and that the side chains cause repulsion each other. In this specification, the compound having the thus designed side chains is collectively expressed as a "starburst-shaped" or "star-shaped" compound.

While the compound having a central nucleus containing an SP3 carbon element and containing a branched structure formed thereby has been described, the structure of the central nucleus is not particularly limited so far as the side chains are able to ensure a large free volume. As a matter of course, the structure may be a cyclic structure. Moreover, in a compound obtained by connecting a side chain having a prescribed structure $(-D^1-(E)_q-D^2-(B)_m-Z^1-R)$ which the compound represented by the foregoing formula (Z) has, to a central nucleus containing an element capable of becoming trivalent or polyvalent, such as nitrogen, silicon, boron, phosphorus, etc. and containing a branched structure formed thereby, the side chain is also able to ensure a large free volume and exhibits the same effect; and such compounds fall within the scope of the invention.

Moreover, the compound of the invention may be either a polymer or an oligomer. More specifically, in a polymer or oligomer obtained by connecting the side chain having a prescribed structure ($-D^1-(E)_q-D^2-(B)_m-Z^1-R$) to a side chain of one or two or more kinds of repeating units constituting a principal chain thereof, and the side chain is also able to ensure a large free volume and exhibits the same effect. The principal chain of the polymer or oligomer may be, for example, a simple structure as in a polyvinyl alcohol chain. Specifically, a polymer or oligomer obtained by substituting an acetyl group of polyvinyl acetate with the side chain having a prescribed structure ($-D^1-(E)_q-D^2-(B)_m-Z^1-R$), which the compound represented by the foregoing formula (Z) has, falls within the scope of the invention.

Among examples of the central nucleus structure bonding the foregoing side chain thereto, those of hydrocarbon chains include pentaerythritol, oligo-pentaerythritols inclusive of di-, tri- or tetraerythritol, groups obtained by connecting one hydroxyl group of pentaerythritol to other divalent group (for example, a substituted or non-substituted alkylene group, cycloalkylene group, alkenylene group, alkynylene group or arylene group, a divalent heterocyclic aromatic ring group or heterocyclic non-aromatic ring group, a divalent group selected among an imino group, an oxy group, a sulfide group, a sulfenyl group, a sulfonyl group, a phosphoryl group and an alkyl-substituted silyl group, or a divalent group composed of a combination of two or more of these groups); and residues of glycerol, xylitol, sorbitol, inositol, trimethylolpropane, ditrimethylpropane, neopentyl glycol or polyglycerin.

In the foregoing formula (Z), preferred examples of A are a group represented by any of following formulae (AI) to (AIII).

In the formulae, * means a bonding site to $-D^1-(E)_q-D^2-(B)_m-Z^1-R$; C represents a carbon atom; $R^0$ represents a hydrogen atom or a substituent; each of $X^1$ to $X^4$, $X^{11}$ to $X^{14}$ and $X^{21}$ to $X^{24}$ represents a hydrogen atom or a halogen atom (for example, a fluorine atom or a chlorine atom) and may be the same as or different from every other; each of n1 to n3 represents an integer of from 0 to 5 and preferably represents an integer of 1 or 2; and m4 represents an integer of from 0 to 8 and preferably represents an integer of 0 or 2.

In the foregoing formula (AI), examples of the substituent represented by $R^0$ include a substituted or non-substituted alkyl group having from 1 to 50 carbon atoms (for example, in addition to methyl and ethyl, linear or branched propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl or tetracosyl); an alkenyl group having from 2 to 35 carbon atoms (for example, propenyl, butenyl, pentenyl, hexenyl, heptenyl, octenyl, nonenyl, decenyl, undecenyl or dodecenyl); a cycloalkyl group having from 3 to 10 carbon atoms (for example, cyclopropyl, cyclobutyl, cyclopentyl, cyclohexyl or cycloheptyl); an aromatic ring group having from 6 to 30 carbon atoms (for example, phenyl, naphthyl, biphenyl, phenanthryl or anthracenyl); a heterocyclic group (preferably a residue of a heterocyclic ring containing at least one hetero atom selected among a nitrogen atom, an oxygen atom and a sulfur atom; for example, pyridyl, pyrimidyl, triazinyl, thienyl, furyl, pyrrolyl, pyrazolyl, imidazolyl, triazolyl, thiazolyl, imidazolyl, oxazolyl, thiadialyl, oxadiazolyl, quinolyl or isoquinolyl); and a group composed of a combination of these groups. If possible, such a substituent may further have one or more substituents, and examples of the substituent include an alkoxy group, an alkoxycarbonyl group, a halogen atom, an ether group, an alkyl carbonyl group, a cyano group, a thioether group, a sulfoxide group, a sulfonyl group, an amide group, etc.

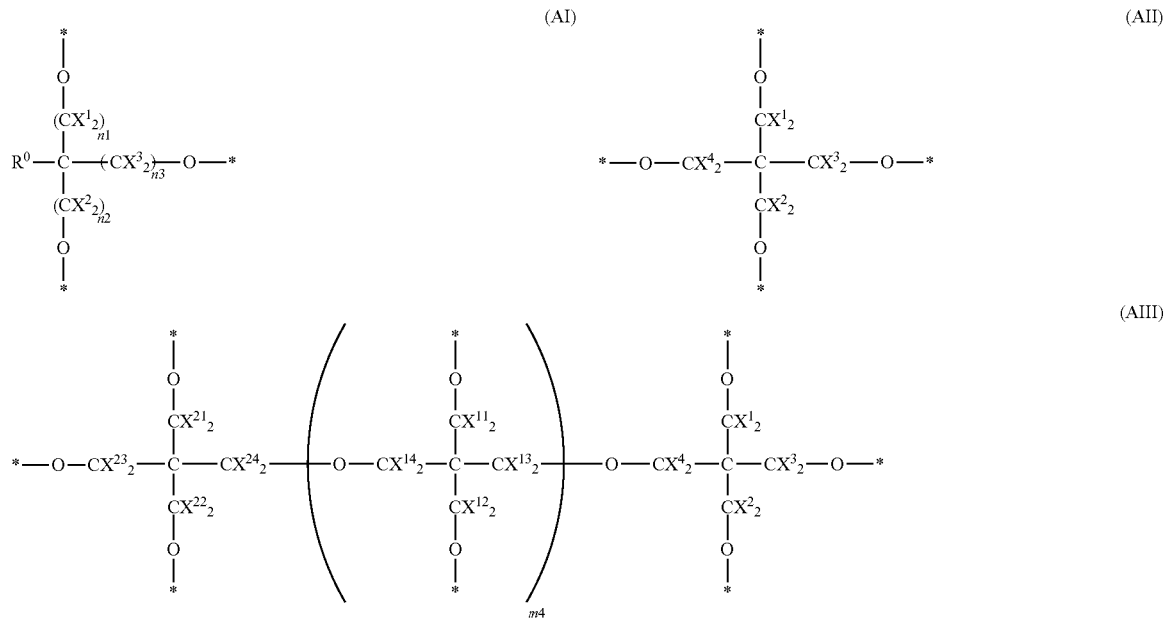

Though all of the compounds having a group represented by any of the formulae (AI) to (AIII) as A are preferable, from the viewpoint of synthesis, compounds having a group presented by the formula (AII), namely pentaerythritol derivatives are preferable.

In the formula (Z), L represents a single bond, an oxy group, a substituted or non-substituted oxymethylene group represented by following formula (A-a), or a substituted or non-substituted oxyethyleneoxy group represented by following formula (A-b). In following formulae, Alk represents a hydrogen atom, a $C_1$-$C_6$ alkyl group or a cycloalkyl group.

   (A-a)

   (A-b)

In the formula (Z), $D^1$ represents a carbonyl group (—C(=O)—) or a sulfonyl group (—S(=O)$_2$—), and each $D^1$ may be the same as or different from every other $D^1$; and $D^2$ represents a carbonyl group (—C(=O)—), a sulfonyl group (—S(=O)$_2$—), a carboxyl group (—C(=O)O—), a sulfonyloxyl group (—S(=O)$_2$O—), a carbamoyl group (—C(=O)N(Alk)-) or a sulfamoyl group (—S(=O)$_2$N(Alk)-). Alk represents a hydrogen atom, a $C_1$-$C_6$ alkyl group or a cycloalkyl group.

In the formula (Z), each E represents a single bond, a substituted or non-substituted alkylene group (preferably a $C_1$-$C_8$ alkylene group; for example, methylene, ethylene, propylene, butylene, pentylene, hexylene, heptylene or octylene), cycloalkylene group (preferably a $C_3$-$C_{15}$ cycloalkylene group; for example, cyclopropylene, cyclobutylene, cyclopentylene or cyclohexylene), alkenylene group (preferably a $C_2$-$C_8$ alkenylene group; for example, ethene, propene, butene or pentene), alkynylene group (preferably a $C_2$-$C_8$ alkynylene group; for example, ethyne, propyne, butyne or pentyne) or arylene group (preferably a $C_6$-$C_{10}$ arylene group; for example, phenylene), a divalent heterocyclic aromatic ring group or heterocyclic non-aromatic ring group, a divalent group selected among a substituted or non-substituted imino group, an oxy group, a sulfide group, a sulfenyl group, a sulfonyl group, a phosphoryl group and an alkyl-substituted silyl group, or a divalent group composed of a combination of two or more of these groups.

q represents an integer of 0 or more, and may be different from each other when q is 2 or more.

In the foregoing formula (Z), preferred examples of -$D^1$-(E)$_q$-$D^2$- include the following group.

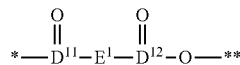

In the foregoing formula, * represents a site bonding to L in the formula; and ** represents a site bonding to B in the formula. Each of $D^{11}$ and $D^{12}$ represents a carbon atom or S(=O), and preferably a carbon atom. $E^1$ represents a single bond; a linear or branched, substituted or non-substituted $C_1$-$C_8$ alkylene group, $C_2$-$C_8$ alkenylene group or $C_2$-$C_8$ alkynylene group (provided that the carbon atom may be substituted with an oxygen atom); a substituted or non-substituted $C_3$-$C_{15}$ cycloalkylene group, cycloalkenylene group or cycloalkynylene group; a substituted or non-substituted $C_6$-$C_{10}$ arylene group; a substituted or non-substituted aromatic or non-aromatic heterocyclic group; —NH—; or —NH-Alk"-NH— (wherein Alk" represents a $C_1$-$C_4$ alkylene group). Examples of the substituent of the alkylene group and the like include a halogen atom (for example, a fluorine atom or a chlorine atom). Preferred examples of $E^1$ include a single bond and a divalent group such as methylene, ethylene, propylene, methyleneoxymethylene, vinylene, imino, tetrafluoroethylene, iminohexyleneimino, etc.

In the formula (Z), R represents a hydrogen atom, a substituted or non-substituted $C_8$ or longer alkyl group, a perfluoroalkyl group or a trialkylsilyl group.

The $C_8$ or longer alkyl group represented by each R is preferably a $C_{12}$ or longer alkyl group. Moreover, the alkyl group is preferably a $C_{30}$ or shorter alkyl group, and more preferably a $C_{20}$ or shorter alkyl group. The alkyl group may be either linear or branched. Specific examples thereof include decyl, tridecyl, tetradecyl, pentadecyl, hexadecyl, heptadecyl, octadecyl, nonadecyl, eicosyl, heneicosyl, docosyl, tricosyl, octacosyl, triacontyl, pentatriacontyl, tetracontyl, pentacontyl, hexacontyl, octacontyl and decacontyl. Such an alkyl group may have one or more substituents. Examples of the substituent include a halogen atom (for example, a fluorine atom and a chlorine atom), a hydroxyl group, an amino group, an alkylamino group, a mercapto group, an alkylthio group, an alkoxy group, a cyano group, etc.

The perfluoroalkyl group represented by each R is preferably a $C_1$-$C_{10}$ perfluoroalkyl group, more preferably a $C_1$-$C_6$ perfluoroalkyl group, further preferably a $C_1$-$C_4$ perfluoroalkyl group, and especially preferably a $C_1$-$C_2$ perfluoroalkyl group. Examples thereof include a trifluoromethyl group, a perfluoroethyl group, a perfluoropropyl group, a perfluorobutyl group, a perfluoropentyl group, a perfluorohexyl group, a perfluoroheptyl group and a perfluorooctyl group.

The alkyl group bonding to Si of the trialkylsilyl group represented by each R is preferably a $C_1$-$C_4$ alkyl group such as methyl, ethyl, etc. Such an alkyl group may be branched.

In the formula (Z), B varies depending upon R; in the case where R represents a hydrogen atom or a substituted or non-substituted $C_8$ or longer alkyl group, B represents a substituted or non-substituted oxyethylene group or a substituted or non-substituted oxypropylene group; plural Bs connecting to each other may be the same as or different from each other; and m represents a natural number of 1 or more, preferably a number of from 4 to 20, and more preferably from 7 to 12.

Each B may be the same as or different from every other B, and for example, a plural kind of units B having a different chain length of the alkylene moiety from each other may be contained, and/or both a unit B in which the alkylene moiety is non-substituted and a unit B in which the alkylene moiety is substituted may be contained. The alkylene moiety of the alkyleneoxy group may have a substituent, and examples of the substituent include a halogen atom (for example, a fluorine atom or a chlorine atom). Moreover, the chain length of the substituted or non-substituted oxyethylene group or the substituted or non-substituted oxypropylene group may have distribution.

In the case where R represents a perfluoroalkyl group, B represents an oxyperfluoromethylene group, an oxyperfluoroethylene group or an optionally branched oxyperfluoropropylene group (examples of the branched oxyperfluoropropylene group include a perfluoroisopropylene group); plural Bs connecting to each other may be the same as or different from each other; and m represents a natural number of 1 or more, preferably a number of from 4 to 20, and more preferably from 7 to 12.

In the case where R represents a trialkylsilyl group, B represents a dialkylsiloxy group in which the alkyl group is selected among a methyl group, an ethyl group and an optionally branched propyl group (examples of the branched propyl group include an isopropyl group); each B may be the same as or different from every other B; plural Bs connecting to each other may be the same as or different from each other; and m represents a natural number of 1 or more, preferably a number of from 4 to 20, and more preferably from 7 to 12.

In the formula (Z), $Z^1$ represents a single bond, a divalent group selected among a carbonyl group, a sulfonyl group, a phosphoryl group, an oxy group, a substituted or non-substituted amino group, a sulfide group, an alkenylene group, an alkynylene group and an arylene group or a divalent group composed of a combination of two or more of these groups. As an example of the divalent connecting group, a divalent connecting group composed of a combination of one or more members selected among a carbonyl group, a sulfonyl group, a phosphoryl group, an oxy group, a substituted or non-substituted imino group, a sulfide group, a $C_1$-$C_6$ alkylene group, a $C_1$-$C_{16}$ cycloalkylene group, a $C_2$-$C_8$ alkenylene group, a $C_2$-$C_5$ alkynylene group, a $C_6$-$C_{10}$ arylene group and a $C_3$-$C_{10}$ heterocyclic group is preferable. Examples of the connecting group composed of a combination of plural groups include —CONH—, —CO-cyclohexylene-, —CO—Rh— (wherein Rh represents a phenylene group; hereinafter the same), —CO—C≡C-Ph-, —CO—CH=CH-Ph-, —CO-Ph-N=N-Ph-O—, —$C_nH_{2n}$—NR— (n represents from 1 to 4; R represents a hydrogen atom or a $C_1$-$C_4$ alkyl group; and the right side is bonded to the end side) and —N,N'-pyrazylene-.

As described previously, in the formula (Z), each R may be the same as or different from every other R and represents a substituted or non-substituted $C_8$ or longer alkyl group, a perfluoroalkyl group or a trialkylsilyl group. In more detail, as for —(B)$_m$—$Z^1$—R in the formula (Z), when R represents a substituted or non-substituted alkyl group having 8 or more carbon atoms, following formula (ECa) is preferable; when R represents a perfluoroalkyl group, following formula (ECb) is preferable; and when R represents a trialkylsilyl group, following formula (ECa) is preferable.

In the formula (Z), when R represents a substituted or non-substituted $C_8$ or longer alkyl group, —(B)$_m$—$Z^1$—R is preferably a group represented by following formula (ECa).

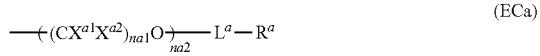

In the formula (ECa), C represents a carbon atom; O represents an oxygen atom; $L^a$ (corresponding to $Z^1$ in the formula (Z)) represents a single bond or a divalent connecting group; each of $X^{a1}$ and $X^{a2}$ represents a hydrogen atom, a halogen atom or a substituent (preferably a hydrogen atom or a fluorine atom, and more preferably a hydrogen atom); na1 represents an integer of from 1 to 4; when na1 is 2 or more, plural $X^{a1}$s and $X^{a2}$s may be the same as or different from each other; na2 represents a number of from 1 to 35 (preferably from 4 to 20, and more preferably from 4 to 10); and $R^a$ (corresponding to R in the formula (Z)) represents a substituted or non-substituted $C_8$ or longer alkyl group (preferably $C_{12}$ or longer and also preferably $C_{30}$ or shorter, and more preferably $C_{24}$ or shorter).

$L^a$ is preferably a single bond or a divalent connecting group composed of a combination of one or more members selected among a carbonyl group, a sulfonyl group, a phosphoryl group, an oxy group, a substituted or non-substituted amino group, a thio group, an alkylene group, an alkenylene group, an alkynylene group and an arylene group.

In the formula (Z), when R represents a perfluoroalkyl group, —(B)$_m$—$Z^1$—R is preferably a group represented by following formula (ECb).

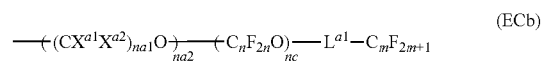

In the formula (ECb), the same symbols as those in the formula (ECa) are synonymous, respectively; $L^{a1}$ corresponding to $Z^1$ in the formula (Z) represents a single bond; na2 represents a number of from 0 to 2; nc represents a number of from 1 to 10; m represents a number of from 1 to 12; and n represents a number of from 1 to 6.

nc is preferably from 3 to 8. m is preferably a number of from 1 to 8, and more preferably from 1 to 4. n is preferably from 1 to 3.

Moreover, a preferred example of the formula (ECb) is a group represented by following formula (ECb').

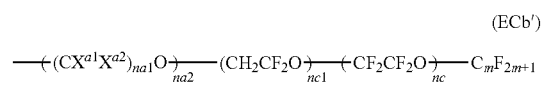

In the formula (ECb'), the same symbols as those in the formula (ECb) are synonymous, and preferred ranges thereof are also the same. nc1 is 1 or 2, and preferably 1.

In the formula (Z), when R represents a trialkylsilyl group, —(B)$_m$—$Z^1$—R is preferably a group represented by following formula (ECc).

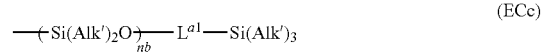

In the formula (ECc), the same symbols as those in the formula (ECa) are synonymous, respectively; each Alk' may be the same as or different from every other Alk' and represents a $C_1$-$C_8$ alkyl group; $L^{a1}$ (corresponding to $Z^1$ in the formula (Z)) represents a single bond; and nb represents a number of from 1 to 10. nb is preferably a number of from 2 to 20, and more preferably from 3 to 10.

In the foregoing formula (Z), p represents an integer of 2 or more, preferably 3 or more, and more preferably from 3 to 8. In view of the fact that the compound of the formula (Z) has plural side chains having a prescribed structure, it is able to achieve a low coefficient of friction.

Examples of the compound represented by the formula (Z) are given below, but it should not be construed that the invention is limited thereto.

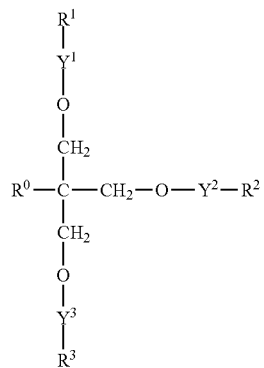

(AI)

| Compound No. | $R^0$ | $Y^1 = Y^2 = Y^3$ | $R^1$ | $R^2$ | $R^3$ |
|---|---|---|---|---|---|
| AI-1 | $C_2H_5$ | $COC_2H_4CO_2$ | $(C_2H_4O)_{6.5}C_{22}H_{44}$-n | $(C_2H_4O)_{6.5}C_{22}H_{45}$-n | $(C_2H_4O)_{6.5}C_{22}H_{45}$-n |
| AI-2 | $C_2H_5$ | $COC_2H_4CO_2$ | $(C_2H_4O)_{6.5}C_{20}H_{41}$-n | $(C_2H_4O)_{6.5}C_{20}H_{41}$-n | $(C_2H_4O)_{6.5}C_{20}H_{41}$-n |
| AI-3 | $C_2H_5$ | $COC_2H_4CO_2$ | $(C_2H_4O)_{6.5}C_{18}H_{37}$-n | $(C_2H_4O)_{6.5}C_{18}H_{37}$-n | $(C_2H_4O)_{6.5}C_{18}H_{37}$-n |
| AI-4 | $C_2H_5$ | $COC_2H_4CO_2$ | $(C_2H_4O)_{6.5}C_{16}H_{33}$-n | $(C_2H_4O)_{6.5}C_{16}H_{33}$-n | $(C_2H_4O)_{6.5}C_{16}H_{33}$-n |
| AI-5 | $C_2H_5$ | $COC_2H_4CO_2$ | $(C_2H_4O)_{6.5}C_{14}H_{29}$-n | $(C_2H_4O)_{6.5}C_{14}H_{29}$-n | $(C_2H_4O)_{6.5}C_{14}H_{29}$-n |
| AI-6 | $C_2H_5$ | $COC_2H_4CO_2$ | $(C_2H_4O)_{6.5}C_{12}H_{25}$-n | $(C_2H_4O)_{6.5}C_{12}H_{25}$-n | $(C_2H_4O)_{6.5}C_{12}H_{25}$-n |
| AI-7 | $C_2H_5$ | $COC_2H_4CO_2$ | $(C_2H_4O)_{6.5}C_{26}H_{53}$-n | $(C_2H_4O)_{6.5}C_{26}H_{53}$-n | $(C_2H_4O)_{6.5}C_{26}H_{53}$-n |
| AI-8 | $C_2H_5$ | $COC_2H_4CO_2$ | $(C_2H_4O)_{6.5}C_{35}H_{71}$-n | $(C_2H_4O)_{6.5}C_{35}H_{71}$-n | $(C_2H_4O)_{6.5}C_{35}H_{71}$-n |
| AI-9 | $CH_3$ | $COC_2H_4CO_2$ | $(C_2H_4O)_{6.5}CH(C_6H_{13}$-n$)C_9H_{19}$-n | $(C_2H_4O)_{6.5}CH$-$CH(C_6H_{13}$-n$)C_9H_{19}$-n | $(C_2H_4O)_{6.5}CH$-$(C_6H_{13}$-n$)C_9H_{19}$-n |
| AI-10 | $CH_3$ | $COC_2H_4CO_2$ | $(C_2H_4O)_{6.5}CH(C_6H_{13}$-n$)C_9H_{19}$-n | $(C_2H_4O)_{6.5}C_{18}H_{37}$-n | $(C_2H_4O)_{6.5}C_{20}H_{41}$-n |
| AI-11 | $CH_3$ | $COC_2H_4CO_2$ | $(C_2H_4O)_4COC_{21}H_{43}$-n | $(C_2H_4O)_4COC_{21}H_{43}$-n | $(C_2H_4O)_4COC_{21}H_{43}$-n |
| AI-12 | $CH_3$ | $COC_2H_4CO_2$ | $(C_2H_4O)_{6.2}CONHC_{18}H_{37}$-n | $(C_2H_4O)_{6.2}$-$CONHC_{18}H_{37}$-n | $(C_2H_4O)_{6.2}$-$CONHC_{18}H_{37}$-n |
| AI-13 | $CH_3$ | $COC_2H_4CO_2$ | $(C_2H_4O)_{6.2}COC_6H_4C_{18}H_{37}$-n | $(C_2H_4O)_{6.2}$-$COC_6H_4C_{18}H_{37}$-n | $(C_2H_4O)_{6.2}$-$COC_6H_4C_{18}H_{37}$-n |
| AI-14 | $CH_3$ | $COC_2H_4CO_2$ | $(C_2H_4O)_4PO_2C_{21}H_{43}$-n | $(C_2H_4O)_4PO_2C_{21}H_{43}$-n | $(C_2H_4O)_4PO_2C_{21}H_{43}$-n |
| AI-15 | $CH_3$ | $COC_2H_4CO_2$ | $(C_2H_4O)_4SO_2C_{18}H_{37}$-n | $(C_2H_4O)_4SO_2C_{18}H_{37}$-n | $(C_2H_4O)_4SO_2C_{18}H_{37}$-n |
| AI-16 | $CH_3$ | $COC_2H_4CO_2$ | $(C_2H_4O)_{6.2}COC{\equiv}CC_6H_4C_{18}H_{37}$-n | $(C_2H_4O)_{6.2}$-$COC{\equiv}CC_6H_4C_{18}H_{37}$-n | $(C_2H_4O)_{6.2}$-$COC{\equiv}CC_6H_4C_{18}H_{37}$-n |
| AI-17 | $CH_3$ | $COC_2H_4CO_2$ | $(C_2H_4O)_{6.2}COCH{=}CHC_6H_4C_{18}H_{37}$-n | $(C_2H_4O)_{6.2}$-$COCH{=}CHC_6H_4C_{18}H_{37}$-n | $(C_2H_4O)_{6.2}$-$COCH{=}CHC_6H_4C_{18}H_{37}$-n |
| AI-18 | $CH_3$ | $COC_2H_4CO_2$ | $(C_2H_4O)_{6.2}C_2H_4N(CH_3)C_{18}H_{37}$-n | $(C_2H_4O)_{6.2}$-$C_2H_4N(CH_3)C_{18}H_{37}$-n | $(C_2H_4O)_{6.2}$-$C_2H_4N(CH_3)C_{18}H_{37}$-n |
| AI-19 | $CH_3$ | $COC_2H_4CO_2$ | $(C_3H_6O)_3C_{16}H_{33}$-n | $(C_3H_6O)_3C_{16}H_{33}$-n | $(C_3H_6O)_3C_{16}H_{33}$-n |
| AI-20 | $CH_3$ | $COC_2H_4CO_2$ | $(C_3H_6O)_{32}(C_2H_4O)_4COC_{21}H_{43}$-n | $(C_3H_6O)_{32}$-$(C_2H_4O)_4COC_{21}H_{43}$-n | $(C_3H_6O)_{32}$-$(C_2H_4O)_4COC_{21}H_{43}$-n |
| AI-21 | $CH_3$ | $COC_2H_4CO_2$ | $(C_3H_6O)_{32}(C_2H_4O)_4COC_{22}H_{45}$-n | $(C_3H_6O)_{32}$-$(C_2H_4O)_4COC_{22}H_{45}$-n | $(C_3H_6O)_{32}$-$(C_2H_4O)_4COC_{22}H_{45}$-n |
| AI-22 | $CH_3$ | $COCH_2CO_2$ | $(C_2H_4O)_{6.5}C_{22}H_{45}$-n | $(C_2H_4O)_{6.5}C_{22}H_{45}$-n | $(C_2H_4O)_{6.5}C_{22}H_{45}$-n |
| AI-23 | $CH_3$ | $COC_3H_6CO_2$ | $(C_2H_4O)_{6.5}C_{22}H_{45}$-n | $(C_2H_4O)_{6.5}C_{22}H_{45}$-n | $(C_2H_4O)_{6.5}C_{22}H_{45}$-n |
| AI-24 | $CH_3$ | $COC_4H_8CO_2$ | $(C_2H_4O)_{6.5}C_{22}H_{45}$-n | $(C_2H_4O)_{6.5}C_{22}H_{45}$-n | $(C_2H_4O)_{6.5}C_{22}H_{45}$-n |
| AI-25 | $CH_3$ | $COCH{=}CHCO_2$ | $(C_2H_4O)_{6.5}C_{22}H_{45}$-n | $(C_2H_4O)_{6.5}C_{22}H_{45}$-n | $(C_2H_4O)_{6.5}C_{22}H_{45}$-n |
| AI-26 | $CH_3$ | $COCH_2OCH_2CO_2$ | $(C_2H_4O)_{6.5}C_{22}H_{45}$-n | $(C_2H_4O)_{6.5}C_{22}H_{45}$-n | $(C_2H_4O)_{6.5}C_{22}H_{45}$-n |
| AI-27 | $CH_3$ | $1.2$-$COC_6H_4CO_2$ | $(C_2H_4O)_{6.5}C_{22}H_{45}$-n | $(C_2H_4O)_{6.5}C_{22}H_{45}$-n | $(C_2H_4O)_{6.5}C_{22}H_{45}$-n |
| AI-28 | $C_6H_5$ | $1.4$-$COC_6H_4CO_2$ | $(C_2H_4O)_{6.5}C_{22}H_{45}$-n | $(C_2H_4O)_{6.5}C_{22}H_{45}$-n | $(C_2H_4O)_{6.5}C_{22}H_{45}$-n |
| AI-29 | $C_6H_5$ | $COCH_2C(CH3)_2CH_2CO_2$ | $(C_2H_4O)_{6.5}C_{22}H_{45}$-n | $(C_2H_4O)_{6.5}C_{22}H_{45}$-n | $(C_2H_4O)_{6.5}C_{22}H_{45}$-n |
| AI-30 | $C_2F_5$ | $COC_2F_4CO_2$ | $(C_2H_4O)_{6.5}C_{22}H_{45}$-n | $(C_2H_4O)_{6.5}C_{22}H_{45}$-n | $(C_2H_4O)_{6.5}C_{22}H_{45}$-n |
| AI-31 | $C_2F_5$ | $1.2$-$COC_6F_4CO_2$ | $(C_2H_4O)_{6.5}C_{22}H_{45}$-n | $(C_2H_4O)_{6.5}C_{22}H_{45}$-n | $(C_2H_4O)_{6.5}C_{22}H_{45}$-n |
| AI-32 | $C_2F_5$ | $CONHCO_2$ | $(C_2H_4O)_{6.5}C_{22}H_{45}$-n | $(C_2H_4O)_{6.5}C_{22}H_{45}$-n | $(C_2H_4O)_{6.5}C_{22}H_{45}$-n |
| AI-33 | $C_2F_5$ | $CONHSO_3$ | $(C_2H_4O)_{6.5}C_{22}H_{45}$-n | $(C_2H_4O)_{6.5}C_{22}H_{45}$-n | $(C_2H_4O)_{6.5}C_{22}H_{45}$-n |
| AI-34 | $C_2F_5$ | $SO2NHCO_2$ | $(C_2H_4O)_{6.5}C_{22}H_{45}$-n | $(C_2H_4O)_{6.5}C_{22}H_{45}$-n | $(C_2H_4O)_{6.5}C_{22}H_{45}$-n |
| AI-36 | $C_2F_5$ | $COCO_2$ | $(C_2H_4O)_{6.5}C_{22}H_{45}$-n | $(C_2H_4O)_{6.5}C_{22}H_{45}$-n | $(C_2H_4O)_{65}C_{22}H_{45}$-n |
| AI-37 | $C_2F_5$ | $COC_2H_4CO_2$ | $(C_2H_4O)_{10.3}C_{22}H_{45}$-n | $(C_2H_4O)_{10.3}C_{22}H_{45}$-n | $(C_2H_4O)_{10.3}C_{22}H_{45}$-n |
| AI-38 | $C_2F_5$ | $COC_2H_4CO_2$ | $(C_2H_4O)_{19.7}C_{22}H_{45}$-n | $(C_2H_4O)_{19.7}C_{22}H_{45}$-n | $(C_2H_4O)_{19.7}C_{22}H_{45}$-n |
| AI-39 | $C_5H_4N$ | $COC_2H_4CO_2$ | $(C_2H_4O)_{35.2}C_{22}H_{45}$-n | $(C_2H_4O)_{35.2}C_{22}H_{45}$-n | $(C_2H_4O)_{35.2}C_{22}H_{45}$-n |

-continued

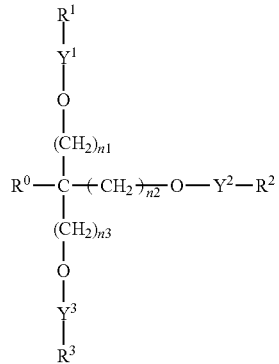

(AI)

| Compound No. | R⁰ | n1 | n2 | n3 | $Y^1 = Y^2 = Y^3$ | $R^1$ | $R^2$ | $R^3$ |
|---|---|---|---|---|---|---|---|---|
| AI-42 | $C_5H_4N$ | 4 | 4 | 4 | $COC_2H_4CO_2$ | $(C_2H_4O)_{6.5}C_{22}H_{45}$-n | $(C_2H_4O)_{6.5}C_{22}H_{45}$-n | $(C_2H_4O)_{6.5}C_{22}H_{45}$-n |
| AI-43 | H | 1 | 1 | 1 | $COC_2H_4CO_2$ | $(C_2H_4O)_{6.5}C_{22}H_{45}$-n | $(C_2H_4O)_{6.5}C_{22}H_{45}$-n | $(C_2H_4O)_{6.5}C_{22}H_{45}$-n |
| AI-44 | H | 1 | 1 | 1 | $COC_2H_4CO_2$ | $(C_2H_4O)_{6.5}CH(C_6H_{13}$-n$)C_9H_{19}$-n | $(C_2H_4O)_{6.5}$-$CH(C_6H_{13}$-n$)C_9H_{19}$-n | $(C_2H_4O)_{6.5}$-$CH(C_6H_{13}$-n$)C_9H_{19}$-n |
| AI-45 | H | 1 | 1 | 1 | $COC_2H_4CO_2$ | $(C_2H_4O)_{6.2}CONHC_{15}H_{31}$-n | $(C_2H_4O)_{6.2}$-$CONHC_{15}H_{31}$-n | $(C_2H_4O)_{6.2}$-$CONHC_{15}H_{31}$-n |
| AI-55 | H | 1 | 1 | 1 | $CONHC_6H_{12}NHCO_2$ | $(C_2H_4O)_{6.5}C_{22}H_{45}$-n | $(C_2H_4O)_{6.5}C_{22}H_{45}$-n | $(C_2H_4O)_{6.5}C_{22}H_{45}$-n |
| AI-56 | $C_2H_5$ | 1 | 1 | 1 | $CONHC_6H_{12}NHCO_2$ | $(C_2H_4O)_{6.5}C_{15}H_{31}$-n | $(C_2H_4O)_{6.5}C_{15}H_{31}$-n | $(C_2H_4O)_{6.5}C_{15}H_{31}$-n |
| AI-57 | $C_2H_5$ | 1 | 1 | 1 | $CONHC_6H_{12}NHCO_2$ | $(C_2H_4O)_{6.5}C_{26}H_{53}$-n | $(C_2H_4O)_{6.5}C_{26}H_{53}$-n | $(C_2H_4O)_{6.5}C_{26}H_{53}$-n |
| AI-58 | $C_2H_5$ | 1 | 1 | 1 | $CONHC_6H_{12}NHCO_2$ | $(C_2H_4O)_{6.5}CH(C_6H_{13}$-n$)C_9H_{19}$-n | $(C_2H_4O)_{6.5}$-$CH(C_6H_{13}$-n$)C_9H_{19}$-n | $(C_2H_4O)_{6.5}$-$CH(C_6H_{13}$-n$)C_9H_{19}$-n |
| AI-59 | $C_2H_5$ | 1 | 1 | 1 | $CONHC_6H_{12}NHCO_2$ | $(C_2H_4O)_4COC_{21}H_{43}$-n | $(C_2H_4O)_4COC_{21}H_{43}$-n | $(C_2H_4O)_4COC_{21}H_{43}$-n |
| AI-60 | $C_2H_5$ | 1 | 1 | 1 | $CONHC_6H_{12}NHCO_2$ | $(C_2H_4O)_4COC_{21}H_{43}$-n | $(C_2H_4O)_4COC_{21}H_{43}$-n | $(C_2H_4O)_4COC_{21}H_{43}$-n |
| AI-61 | $C_2H_5$ | 1 | 1 | 0 | $CONHC_6H_{12}NHCO_2$ | $(C_2H_4O)_4COC_{21}H_{43}$-n | $(C_2H_4O)_4COC_{21}H_{43}$-n | $(C_2H_4O)_4COC_{21}H_{43}$-n |
| AI-62 | $C_2H_5$ | 1 | 0 | 0 | $CONHC_6H_{12}NHCO_2$ | $(C_2H_4O)_4COC_{21}H_{43}$-n | $(C_2H_4O)_4COC_{21}H_{43}$-n | $(C_2H_4O)_4COC_{21}H_{43}$-n |
| AI-63 | $C_2H_5$ | 0 | 0 | 0 | $CONHC_6H_{12}NHCO_2$ | $(C_2H_4O)_4COC_{21}H_{43}$-n | $(C_2H_4O)_4COC_{21}H_{43}$-n | $(C_2H_4O)_4COC_{21}H_{43}$-n |
| AI-64 | $C_2H_5$ | 1 | 1 | 0 | $COCH_2CO_2$ | $(C_2H_4O)_{6.5}C_{22}H_{45}$-n | $(C_2H_4O)_{6.5}C_{22}H_{45}$-n | $(C_2H_4O)_{6.5}C_{22}H_{45}$-n |
| AI-65 | $C_2H_5$ | 1 | 0 | 0 | $COCH_2CO_2$ | $(C_2H_4O)_{6.5}C_{22}H_{45}$-n | $(C_2H_4O)_{6.5}C_{22}H_{45}$-n | $(C_2H_4O)_{6.5}C_{22}H_{45}$-n |
| AI-66 | $C_2H_5$ | 1 | 0 | 0 | $COCH_2CO_2$ | $(C_2H_4O)_{6.5}C_{22}H_{45}$-n | $(C_2H_4O)_{6.5}C_{22}H_{45}$-n | $(C_2H_4O)_{6.5}C_{22}H_{45}$-n |

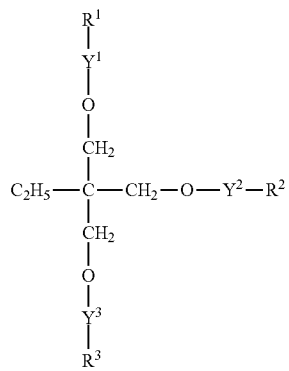

(AI)

| Compound No. | $Y^1$ | $Y^2$ | $Y^3$ | $R^1 = R^2 = R^3$ |
|---|---|---|---|---|
| AI-67 | $COCH_2CO_2$ | $COC_2H_4CO_2$ | $COC_2H_4CO_2$ | $(C_2H_4O)_{10.3}C_8H_{17}$-n |
| AI-68 | $COCH_2CO_2$ | $COC_2H_4CO_2$ | $COC_2H_4CO_2$ | $(C_2H_4O)_{19.7}C_8H_{17}$-n |
| AI-69 | $COCH_2CO_2$ | $COC_2H_4CO_2$ | $COC_2H_4CO_2$ | $(C_2H_4O)_{15.2}C_8H_{17}$-n |
| AI-70 | $COCH_2CO_2$ | $COCH_2CO_2$ | $COCH_2CO_2$ | $(C_2H_4O)_{15.2}C_8H_{17}$-n |
| AI-71 | $CONHCO_2$ | $COC_2H_4CO_2$ | $COC_2H_4CO_2$ | $(C_2H_4O)_{15.2}CH_2CF_2O(C_2F_4O)_2C_2F_5$-n |
| AI-72 | $CONHSO_3$ | $COC_2H_4CO_2$ | $COC_2H_4CO_2$ | $(C_2H_4O)_{15.2}CH_2CF_2O(C_2F_4O)_2C_2F_5$-n |
| AI-73 | $SO2NHCO_2$ | $COC_2H_4CO_2$ | $COC_2H_4CO_2$ | $(C_2H_4O)_{15.2}CH_2CF_2O(C_2F_4O)_2C_2F_5$-n |
| AI-74 | $CSNHCO_2$ | $COC_2H_4CO_2$ | $COC_2H_4CO_2$ | $(C_2H_4O)_{15.2}CH_2CF_2O(C_2F_4O)_2C_2F_5$-n |
| AI-75 | $COCO_2$ | $COC_2H_4CO_2$ | $COC_2H_4CO_2$ | $(C_2H_4O)_{15.2}CH_2CF_2O(C_2F_4O)_2C_2F_5$-n |
| AI-76 | $COC_2H_4CO_2$ | $COC_2H_4CO_2$ | $COC_2H_4CO_2$ | $(C_2H_4O)_{10.3}(SiMe_2O)_4SiMe_3$-n |
| AI-77 | $COCH_2CO_2$ | $COC_2H_4CO_2$ | $COC_2H_4CO_2$ | $(C_2H_4O)_{10.3}(SiMe_2O)_4SiMe_3$-n |
| AI-78 | $CONHCO_2$ | $COC_2H_4CO_2$ | $COC_2H_4CO_2$ | $(C_2H_4O)_{10.3}(SiMe_2O)_4SiMe_3$-n |
| AI-79 | $CONHSO_3$ | $COC_2H_4CO_2$ | $COC_2H_4CO_2$ | $(C_2H_4O)_{10.3}(SiMe_2O)_4SiMe_3$-n |

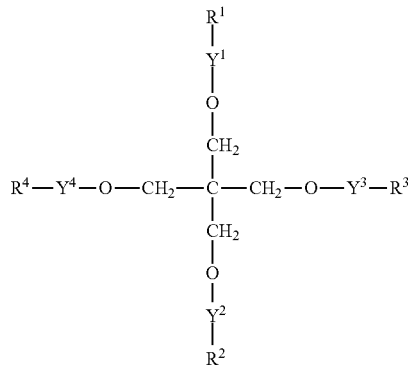

(AII)

| Compound No. | $Y^1 = Y^2 = Y^3 = Y^4$ | $R^1 = R^2 = R^3 = R^4$ |
|---|---|---|
| AII-1 | $COC_2H_4CO_2$ | $(C_2H_4O)_{6.5}C_{22}H_{45}$-n |
| AII-2 | $COC_2H_4CO_2$ | $(C_2H_4O)_{4.0}C_{22}H_{45}$-n |
| AII-3 | $COC_2H_4CO_2$ | $(C_2H_4O)_{6.52}C_{20}H_{41}$-n |
| AII-4 | $COC_2H_4CO_2$ | $(C_2H_4O)_{6.55}C_{18}H_{37}$-n |
| AII-5 | $COC_2H_4CO_2$ | $(C_2H_4O)_4C_{18}H_{37}$-n |
| AII-6 | $COC_2H_4CO_2$ | $(C_2H_4O)_{6.42}C_{16}H_{33}$-n |
| AII-7 | $COC_2H_4CO_2$ | $(C_2H_4O)_{6.15}C_{14}H_{29}$-n |
| AII-8 | $COC_2H_4CO_2$ | $(C_2H_4O)_4C_{14}H_{29}$-n |
| AII-9 | $COC_2H_4CO_2$ | $(C_2H_4O)_{6.5}C_{12}H_{25}$-n |
| AII-10 | $COC_2H_4CO_2$ | $(C_2H_4O)_{6.5}C_{26}H_{53}$-n |
| AII-11 | $COC_2H_4CO_2$ | $(C_2H_4O)_{6.5}C_{35}H_{71}$-n |
| AII-12 | $COC_2H_4CO_2$ | $(C_2H_4O)_{3.0}C_{22}H_{45}$-n |
| AII-13 | $COC_2H_4CO_2$ | $(C_2H_4O)_{4.0}C_{22}H_{46}$-n |
| AII-14 | $COC_2H_4CO_2$ | $(C_2H_4O)_{6.18}C_{22}H_{45}$-n |
| AII-15 | $COC_2H_4CO_2$ | $(C_2H_4O)_{7.8}C_{22}H_{46}$-n |
| AII-16 | $COC_2H_4CO_2$ | $(C_2H_4O)_{8.4}C_{22}H_{47}$-n |
| AII-17 | $COC_2H_4CO_2$ | $(C_2H_4O)_{10.3}C_{22}H_{48}$-n |
| AII-18 | $COC_2H_4CO_2$ | $(C_2H_4O)_{19.0}C_{22}H_{49}$-n |
| AII-19 | $COC_2H_4CO2$ | $(C_2H_4O)_{27.7}C_{22}H_{50}$-n |
| AII-20 | $COC_2H_4CO2$ | $(C_2H_4O)_{6.5}CH_2CH(C_6H_{13}$-n$)C_9H_{19}$-n |

| Compound No. | $Y^1 = Y^2 = Y^3 = Y^4$ | $R^1$ | $R^2$ | $R^3$ | $R^4$ |
|---|---|---|---|---|---|
| AII-21 | $COC_2H_4CO_2$ | $(C_2H_4O)_{6.5}CH_2CH(C_6H_{13}$-n$)C_9H_{19}$-n | $(C_2H_4O)_{6.5}C_{18}H_{37}$-n | $(C_2H_4O)_{6.5}C_{20}H_{41}$-n | $(C_2H_4O)_{6.5}C_{20}H_{41}$-n |

| Compound No. | $Y^1 = Y^2 = Y^3 = Y^4$ | $R^1 = R^2 = R^3 = R^4$ |
|---|---|---|
| AII-22 | $COC_2H_4CO_2$ | $(C_2H_4O)_4COC_{21}H_{43}$-n |
| AII-23 | $COC_2H_4CO_2$ | $(C_2H_4O)_{6.2}CONHC_{18}H_{37}$-n |
| AII-24 | $COC_2H_4CO_2$ | $(C_2H_4O)_{6.2}COC_6H_4C_{18}H_{37}$-n |
| AII-25 | $COC_2H_4CO_2$ | $(C_2H_4O)_4PO_2C_{21}H_{43}$-n |
| AII-26 | $COC_2H_4CO_2$ | $(C_2H_4O)_4SO_2C_{18}H_{37}$-n |
| AII-27 | $COC_2H_4CO_2$ | $(C_2H_4O)_{6.2}COC{\equiv}CC_6H_4C_{18}H_{37}$-n |
| AII-28 | $COC_2H_4CO_2$ | $(C_2H_4O)_{6.2}COCH{=}CHC_6H_4C_{18}H_{37}$-n |
| AII-29 | $COC_2H_4CO_2$ | $(C_2H_4O)_{6.2}C_2H_4N(CH_3)C_{18}H_{37}$-n |
| AII-30 | $COC_2H_4CO_2$ | $(C_3H_6O)_5C_{16}H_{33}$-n |
| AII-31 | $COC_2H_4CO_2$ | $(C_3H_6O)_{5.2}(C_2H_4O)_4COC_{21}H_{43}$-n |
| AII-32 | $COC_2H_4CO_2$ | $(C_3H_6O)_{5.2}(C_2H_4O)_4C_{22}H_{45}$-n |
| AII-33 | $COCH_2CO_2$ | $(C_2H_4O)_{6.18}C_{22}H_{45}$-n |
| AII-34 | $COC_3H_6CO_2$ | $(C_2H_4O)_{6.18}C_{22}H_{45}$-n |
| AII-35 | $COC_4H_8CO_2$ | $(C_2H_4O)_{6.18}C_{22}H_{45}$-n |
| AII-36 | $COCH{=}CHCO_2$ | $(C_2H_4O)_{6.18}C_{22}H_{45}$-n |
| AII-37 | $COCH_2OCH_2CO_2$ | $(C_2H_4O)_{6.18}C_{22}H_{45}$-n |
| AII-38 | $1.2\text{-}COC_6H_4CO_2$ | $(C_2H_4O)_{6.18}C_{22}H_{45}$-n |
| AII-39 | $1.4\text{-}COC_6H_4CO_2$ | $(C_2H_4O)_{6.18}C_{22}H_{45}$-n |
| AII-40 | $COCH_2C(CH3)_2CH_2CO_2$ | $(C_2H_4O)_{6.18}C_{22}H_{45}$-n |
| AII-41 | $COC_2F_4CO_2$ | $(C_2H_4O)_{6.18}C_{22}H_{45}$-n |
| AII-43 | $1.2\text{-}COC_6F_4CO_2$ | $(C_2H_4O)_{6.18}C_{22}H_{45}$-n |
| AII-44 | $COCH_2OCH_2CO_2$ | $(C_2H_4O)_{6.18}C_{22}H_{45}$-n |
| AII-46 | $COCH_2OCH_2CO_2$ | $(C_2H_4O)_4COC_{21}H_{43}$-n |
| AII-47 | $COC_2H_4CO_2$ | $(C_2H_4O)_{6.5}C_{22}H_{45}$-n |
| AII-48 | $COC_2H_4CO_2$ | $(C_2H_4O)_{4.9}C_{22}H_{45}$-n |
| AII-49 | $COC_2H_4CO_2$ | $(C_2H_4O)_{6.39}CH_2CH(C_7H_{15}$-n$)C_9H_{19}$-n |
| AII-50 | $COC_2H_4CO_2$ | $(C_2H_4O)_{6.2}CONHC_{18}H_{37}$-n |
| AII-51 | $COC(CH_3)_2CO_2$ | $(C_2H_4O)_{6.5}C_{22}H_{45}$-n |

-continued

| | | |
|---|---|---|
| AII-52 | $COC(CH_3)_2CO_2$ | $(C_2H_4O)_{6.5}CH(C_6H_{13}-n)C_9H_{19}-n$ |
| AII-53 | $COC(CH_3)_2CO_2$ | $(C_2H_4O)_4COC_{21}H_{43}-n$ |
| AII-54 | $COCH=CHCO_2$ | $(C_2H_4O)_{6.5}C_{22}H_{45}-n$ |
| AII-55 | $COCH=CHCO_2$ | $(C_2H_4O)_{6.5}C_{18}H_{37}-n$ |
| AII-56 | $COCH=CHCO_2$ | $(C_2H_4O)_4COC_{21}H_{43}-n$ |
| AII-57 | $COCH=CHCO_2$ | $(C_2H_4O)_{6.5}C_{22}H_{45}-n$ |
| AII-59 | $COCH_2NCH_3CO_2$ | $(C_2H_4O)_{6.5}C_{22}H_{45}-n$ |
| AII-60 | $CONHC_6H_{12}NHCO_2$ | $(C_2H_4O)_{6.5}C_{22}H_{45}-n$ |
| AII-61 | $CONHC_6H_{12}NHCO_2$ | $(C_2H_4O)_{6.55}C_{18}H_{37}-n$ |
| AII-62 | $CONHC_6H_{12}NHCO_2$ | $(C_2H_4O)_{6.5}C_{26}H_{53}-n$ |
| AII-63 | $CONHC_6H_{12}NHCO_2$ | $(C_2H_4O)_{6.5}CH_2CH(C_6H_{13}-n)C_9H_{19}-n$ |
| AII-64 | $CONHC_6H_{12}NHCO_2$ | $(C_2H_4O)_4COC_{21}H_{43}-n$ |
| AII-65 | $COC_2H_4CO_2$ | A: $(C_2H_4O)_{6.5}C_{22}H_{45}-n$<br>B: $(C_2H_4O)_{6.39}CH_2CH\{C_2H_4CH(CH_3)C_3H_7-n\}C_4H_8CH(CH_3)C_3H_7-n$<br>A:B = 0:100 |
| AII-66 | $COC_2H_4CO_2$ | A: $(C_2H_4O)_{6.5}C_{22}H_{45}-n$<br>B: $(C_2H_4O)_{6.39}CH_2CH\{C_2H_4CH(CH_3)C_3H_7-n\}C_4H_8CH(CH_3)C_3H_7-n$<br>A:B = 99:1 |
| AII-67 | $COC_2H_4CO_2$ | A: $(C_2H_4O)_{6.5}C_{22}H_{45}-n$<br>B: $(C_2H_4O)_{6.39}CH_2CH\{C_2H_4CH(CH_3)C_3H_7-n\}C_4H_8CH(CH_3)C_3H_7-n$<br>A:B = 95:5 |
| AII-68 | $COC_2H_4CO_2$ | A: $(C_2H_4O)_{6.5}C_{22}H_{45}-n$<br>B: $(C_2H_4O)_{6.39}CH_2CH\{C_2H_4CH(CH_3)C_3H_7-n\}C_4H_8CH(CH_3)C_3H_7-n$<br>A:B = 90:10 |
| AII-69 | $COC_2H_4CO_2$ | A: $(C_2H_4O)_{6.5}C_{22}H_{45}-n$<br>B: $(C_2H_4O)_{6.39}CH_2CH\{C_2H_4CH(CH_3)C_3H_7-n\}C_4H_8CH(CH_3)C_3H_7-n$<br>A:B = 80:20 |
| AII-70 | $CONHCO_2$ | $(C_2H_4O)_{6.5}C_{22}H_{45}-n$ |
| AII-71 | $CONHSO_3$ | $(C_2H_4O)_{6.5}C_{22}H_{45}-n$ |
| AII-72 | $SO2NHCO_2$ | $(C_2H_4O)_{6.5}C_{22}H_{45}-n$ |
| AII-74 | $COCO_2$ | $(C_2H_4O)_{6.5}C_{22}H_{45}-n$ |
| AII-75 | $COC_2H_4CO_2$ | $(C_2H_4O)_{10.3}C_8H_{17}-n$ |
| AII-76 | $COC_2H_4CO_2$ | $(C_2H_4O)_{19.7}C_8H_{17}-n$ |
| AII-77 | $COC_2H_4CO_2$ | $(C_2H_4O)_{15.2}C_8H_{17}-n$ |
| AII-78 | $COCH_2CO_2$ | $(C_2H_4O)_{15.2}C_8H_{17}-n$ |
| AII-79 | $CONHCO_2$ | $(C_2H_4O)_{15.2}CH_2CF_2O(C_2F_4O)_2C_2F_5-n$ |
| AII-80 | $CONHSO_3$ | $(C_2H_4O)_{15.2}CH_2CF_2O(C_2F_4O)_2C_2F_5-n$ |
| AII-81 | $SO2NHCO_2$ | $(C_2H_4O)_{15.2}CH_2CF_2O(C_2F_4O)_2C_2F_5-n$ |
| AII-83 | $COCO_2$ | $(C_2H_4O)_{15.2}CH_2CF_2O(C_2F_4O)_2C_2F_5-n$ |
| AII-84 | $COC_2H_4CO_2$ | $(C_2H_4O)_{10.3}(SiMe_2O)_4SiMe_3-n$ |
| AII-85 | $COCH_2CO_2$ | $(C_2H_4O)_{10.3}(SiMe_2O)_4SiMe_3-n$ |
| AII-86 | $CONHCO_2$ | $(C_2H_4O)_{10.3}(SiMe_2O)_4SiMe_3-n$ |
| AII-87 | $CONHSO_3$ | $(C_2H_4O)_{10.3}(SiMe_2O)_4SiMe_3-n$ |
| AII-88 | $COC_2H_4CO_2$ | $(C_2H_4O)_{10.0}C_{18}H_{37}-n$ |
| AII-89 | $COC_2H_4CO_2$ | $(C_2H_4O)_{10.0}C_{12}H_{25}-n$ |
| AII-90 | $COC_2H_4CO_2$ | $(C_2H_4O)_{10.0}C_{22}H_{45}-n$ |

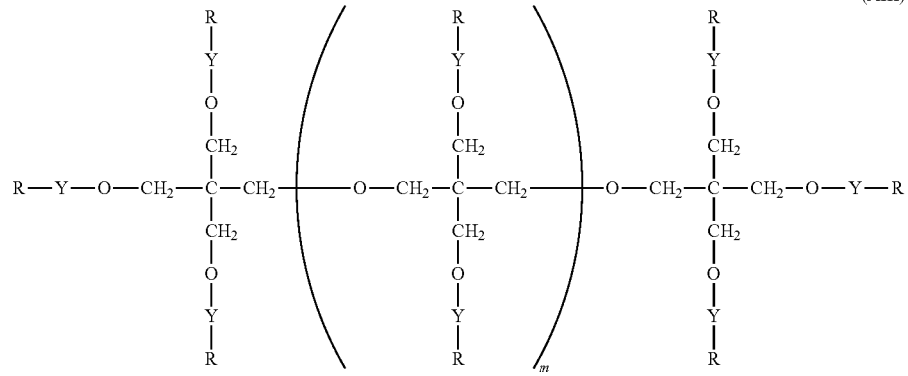

(AIII)

| Compound No. | M | Y | R |
|---|---|---|---|
| AIII-1 | 0 | $COC_2H_4CO_2$ | $(C_2H_4O)_{6.5}C_{22}H_{45}-n$ |
| AIII-2 | 1 | $COC_2H_4CO_2$ | $(C_2H_4O)_{6.5}C_{22}H_{45}-n$ |
| AIII-3 | 2 | $COC_2H_4CO_2$ | $(C_2H_4O)_{6.5}C_{22}H_{45}-n$ |
| AIII-4 | 3 | $COC_2H_4CO_2$ | $(C_2H_4O)_{6.5}C_{22}H_{45}-n$ |
| AIII-5 | 0 | $COC_2H_4CO_2$ | $(C_2H_4O)_4COC_{21}H_{43}-n$ |

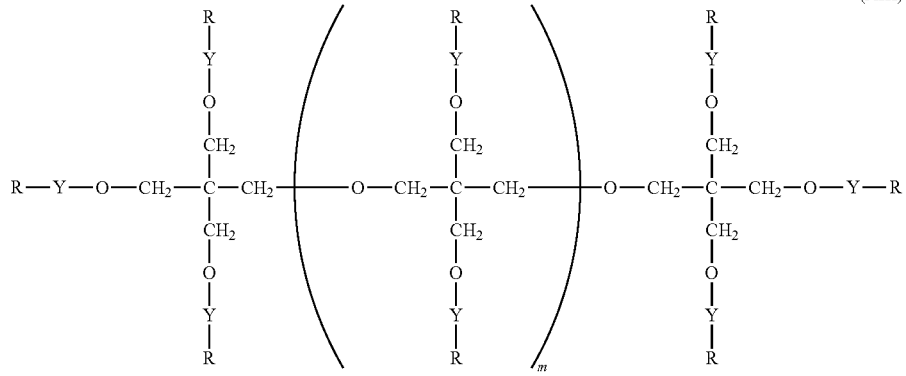

(AIII)

| Compound No. | M | Y | R |
|---|---|---|---|
| AIII-6 | 0 | $COC_2H_4CO_2$ | A: $(C_2H_4O)_{6.5}C_{22}H_{45}$-n<br>B: $(C_2H_4O)_{6.5}CH\{C_2H_4CH(CH_3)C_3H_7\text{-n}\}C_4H_8CH(CH_3)C_3H_7$-n<br>A:B = 95:5 |
| AIII-7 | 2 | $COCH_2OCH_2CO_2$ | $(C_2H_4O)_{6.5}C_{22}H_{45}$-n |
| AIII-8 | 0 | $CONHC_6H_{12}NHCO_2$ | $(C_2H_4O)_{6.5}C_{22}H_{45}$-n |
| AIII-9 | 3 | $CONHC_6H_{12}NHCO_2$ | $(C_2H_4O)_{6.5}C_{20}H_{41}$-n |
| AIII-10 | 1 | $CONHC_6H_{12}NHCO_2$ | $(C_2H_4O)_{6.5}C_{18}H_{37}$-n |
| AIII-11 | 1 | $CONHC_6H_{12}NHCO_2$ | $(C_2H_4O)_4C_{18}H_{37}$-n |
| AIII-12 | 2 | $CONHC_6H_{12}NHCO_2$ | $(C_2H_4O)_{6.5}C_{16}H_{33}$-n |
| AIII-13 | 2 | $CONHC_6H_{12}NHCO_2$ | $(C_2H_4O)_{6.5}C_{14}H_{29}$-n |
| AIII-14 | 3 | $CONHC_6H_{12}NHCO_2$ | $(C_2H_4O)_4C_{14}H_{29}$-n |
| AIII-15 | 3 | $CONHC_6H_{12}NHCO_2$ | $(C_2H_4O)_{6.5}C_{12}H_{25}$-n |
| AIII-16 | 3 | $COCH_2CO_2$ | $(C_2H_4O)_{6.5}C_{22}H_{45}$-n |
| AIII-17 | 3 | $CONHCO_2$ | $(C_2H_4O)_{6.5}C_{22}H_{45}$-n |
| AIII-18 | 3 | $CONHSO_3$ | $(C_2H_4O)_{6.5}C_{22}H_{45}$-n |
| AIII-19 | 3 | $SO2NHCO_2$ | $(C_2H_4O)_{6.5}C_{22}H_{45}$-n |
| AIII-21 | 3 | $COCO_2$ | $(C_2H_4O)_{6.5}C_{22}H_{45}$-n |
| AIII-22 | 3 | $COC_2H_4CO_2$ | $(C_2H_4O)_{10.3}C_{22}H_{45}$-n |
| AIII-23 | 3 | $COC_2H_4CO_2$ | $(C_2H_4O)_{19.7}C_{22}H_{45}$-n |
| AIII-24 | 3 | $COC_2H_4CO_2$ | $(C_2H_4O)_{15.2}C_{22}H_{45}$-n |
| AIII-25 | 3 | $COC_2H_4CO_2$ | $(C_2H_4O)_{10.3}C_8H_{17}$-n |
| AIII-26 | 3 | $COC_2H_4CO_2$ | $(C_2H_4O)_{19.7}C_8H_{17}$-n |
| AIII-27 | 3 | $COC_2H_4CO_2$ | $(C_2H_4O)_{15.2}C_8H_{17}$-n |
| AIII-28 | 3 | $COCH_2CO_2$ | $(C_2H_4O)_{15.2}C_8H_{17}$-n |
| AIII-29 | 3 | $CONHCO_2$ | $(C_2H_4O)_{15.2}CH_2CF_2O(C_2F_4O)_2C_2F_5$-n |
| AIII-30 | 3 | $CONHSO_3$ | $(C_2H_4O)_{15.2}CH_2CF_2O(C_2F_4O)_2C_2F_5$-n |
| AIII-31 | 3 | $SO2NHCO_2$ | $(C_2H_4O)_{15.2}CH_2CF_2O(C_2F_4O)_2C_2F_5$-n |
| AIII-33 | 3 | $COCO_2$ | $(C_2H_4O)_{15.2}CH_2CF_2O(C_2F_4O)_2C_2F_5$-n |
| AIII-34 | 3 | $COC_2H_4CO_2$ | $(C_2H_4O)_{10.3}(SiMe_2O)_4SiMe_3$-n |
| AIII-35 | 3 | $COCH_2CO_2$ | $(C_2H_4O)_{10.3}(SiMe_2O)_4SiMe_3$-n |
| AIII-36 | 3 | $CONHCO_2$ | $(C_2H_4O)_{10.3}(SiMe_2O)_4SiMe_3$-n |
| AIII-37 | 3 | $CONHSO_3$ | $(C_2H_4O)_{10.3}(SiMe_2O)_4SiMe_3$-n |

The compounds represented by the foregoing formulae (Z) can be produced by utilizing various organic synthesis reactions. For example, in the formula (Z), the compound in which A is a group represented by any of the formulae (AI) to (AIII) is basically formed through connection between a polyhydric alcohol such as glycerol, pentaerythritol, etc. and a side chain structure, but in general, an esterification reaction is frequently adopted. For example, the compound can be produced by a condensation reaction between a polyhydric alcohol and an acid chloride of a side chain carboxylic acid, an isocyanate having a side chain structure or an alkyl halide having a side chain structure, or a combination of various reactions of open-ring type esterification of a polyhydric alcohol and succinic anhydride or Meldrum's acid to form a carboxylic acid and esterification of an acid chloride thereof and an alcohol having a side chain structure, or the like. Moreover, the side chain structure portion can be easily produced by using a long-chain alkyl alcohol or an alcohol obtained by adding an ethylene oxide gas to a carboxylic acid, or further using succinic acid, Meldrum's acid or a halocarboxylic acid.

3. Properties of Compound of the Invention

When the compound of the foregoing formula (Z) is dispersed in an oily medium, it forms a coating film in the process in which it is gradually segregated at a high load under a high pressure in a high shear field due to a characteristic feature on the common chemical structure and made high in a concentration, and as compared with the conventional raw materials, it exhibits relatively low friction properties in an elastic fluid lubrication region because of a low viscosity-pressure modulus (low α). In addition, for the same reason (low α), it may be conjectured that such a compound has a wide pressure range for keeping a visco-elastic film and can be prevented from occurrence of the contact with a sliding surface, and as a result, wear resistance is realized.

As for this phenomenon, the present inventor spectrally observed a neighborhood of a point-contacting portion of an instrument named a point contact EHL evaluation apparatus for evaluating an elastic fluid lubrication region in the field of tribology and succeeded in quantitatively grasping a change of material concentration at a high load in a high shear field. Specifically, the observation was carried out in the following manner. First of all, the foregoing compound is dispersed in an oily medium to prepare a sample. Separately, a rotating steel ball is placed on a diamond (hard plane) plate while making its rotation axis parallel, and a load is applied to the axis, thereby bringing them into press contact with each other. The prepared sample is fed and flown in a gap between the rotating steel ball and the diamond plate and its neighborhood.

Though a Newtonian ring which is an optical interference pattern is formed in a portion where the steel ball comes into point contact with the diamond plate, by irradiating infrared rays from the opposite side to the steel ball via the diamond plate and reflecting them on the steel ball, an IR spectrum of a thin film of the sample in the vicinity of the Newtonian ring can be measured. This method is an analysis method of a minute portion in the tribology field described in Junichi ISHIKAWA, Hidetaka NANAO, Ichiro MINAMI and Shigeyuki MORI, *Preprint of the International Tribology Conference* (Tottori, 2004-11), page 243 and is not special. However, according to this method, by changing a rotation speed of the steel ball, a load to the rotation axis and a temperature of the sample, the behavior under various elastic fluid lubrication conditions can be observed on the spot, and this method is an effective method.

When a mineral oil or a poly-α-olefin is used as the oily medium which is used for the preparation of a sample used for the measurement, since such a compound is a hydrocarbon, it is free from characteristic absorption other than C—C and C—H. In consequence, when the foregoing compound has a functional group exhibiting a distinct high-intensity characteristic absorption band, such as a carbonyl group of an ester bond, a cyano group, an ethynyl group, a perfluoroalkyl group, a siloxane group, etc., a change in the concentration can be quantitatively detected from the intensity of the characteristic absorption band.

As a result of observation using the foregoing apparatus, it was noted that in a so-called Hertzian area under a high pressure in a high shear field, where a Newtonian ring is formed, the foregoing compound is gradually segregated in a form of a candle flame formed by partition of a flow of the sample in, for example, a region of from 20 to 400 μm backward. In many cases, the concentration becomes substantially constant for about 5 minutes to 2 hours under a condition at a measurement temperature of 40° C. at a linear velocity of 0.15 m/sec under a Hertzian pressure of 0.3 GPa, an aspect of which is, however, different depending upon a condition such as a temperature, etc.

The foregoing point contact EHL evaluation apparatus is a model of the Hertzian contact area under a high-pressure and high-shear condition, namely a true contact site, and the actual friction contact area is an area where such true contact areas are crowded. Therefore, it may be considered that the composition of the invention containing the foregoing compound in the oily medium accumulates the foregoing compound in the vicinity of a number of true contact areas of such a friction contact area.

In consequence, the foregoing high-viscosity compound is segregated in a sliding part by the oily medium, and a smooth film is formed by a high shear force, whereby its gap becomes narrower than the usual. Therefore, such a low-viscosity oily medium is formed into a thinner film, thereby contributing to low friction of fluid lubrication, and in a fluid lubrication region, a driving machine thereof drives with high efficiency from the energy standpoint. And in a high-load and high-pressure field, it is probable that the foregoing compound is gradually accumulated before the low-viscosity oily medium is broken from the elasto-plastic body film, and therefore, in the case where the viscosity-pressure modulus α of the foregoing compound having been dispersed in the low-viscosity oily medium is small, the viscosity becomes relatively low, and in the contact site, a low coefficient of friction is revealed by a low-viscosity elastic fluid lubricating film made of the subject compound. Under such a high-load condition, the contact area is increased due to an elastic strain of the interface raw material, and a pressure in that portion is lowered. Therefore, a much more mild condition is realized; and even under a condition under which current lubricating oils already come into a boundary lubrication region, a favorable lubrication region where the both interfaces do not substantially come into contact with each other due to the low-viscosity elastic fluid lubricating film of the foregoing compound is kept. As a result, fuel saving is achieved.

Recent fuel-saving type engine oils containing a molybdenum based organometallic complex exhibit low viscosity such that a viscosity at 40° C. is not more than 30 mPa·s and are marketed as a multi-grade low-viscosity oil such as 0W-20 or the like. However, as described previously, in the composition of the invention, in view of the fact that an elastic fluid lubricating film is formed before the low-viscosity based oil is broken, the foregoing compound is able to reveal the same effects of low friction and wear resistance under a high-pressure and high-shear condition at a high temperature. Moreover, substantial low viscosity is revealed by the elastic fluid film even under such a severe condition, and the low-viscosity base oil preferentially functions under a mild condition; and therefore, an increase of the viscosity at middle to low temperatures to be caused due to a viscosity index improver as in current lubricants does not occur.

Moreover, since the composition of the invention does not basically utilize a reaction with the interface, the film forming properties thereof are not restricted by the material quality of the interface. In addition, since the foregoing compound is basically strong against heat and chemically stable, it is relatively conspicuously high in durability. Moreover, the friction portion disappears under a high-load condition, and when the temperature is high, the compound of the invention is again dispersed in the oily medium, whereby the total amount is always kept. When needed, a necessary amount of the compound is accumulated to reveal low friction, and when not needed, the compound is again dispersed; and thus, the composition of the invention is an extremely intelligent lubricant composition.

On the other hand, in the case where the foregoing compound exhibits high α, the composition effectively functions as a traction oil which is used in a site of, for example, transmitting a power by friction of a clutch, etc. In conventional high-function traction oils, hydrocarbons having an incorruptible structure, all of which have a high viscosity-pressure modulus, have been used; however, a defect thereof resides in a point that an atmospheric viscosity of the oil itself must become relatively high. This matter decreases a driving efficiency in a normal state. However, a composition in which a raw material having a high viscosity-pressure modulus among the foregoing compounds is dispersed in a low-viscosity oily medium enables one to make both fuel consumption efficiency and effective transmission of a power compatible with each other. The low-viscosity oily medium occupying the majority of the transmission oil is able to effectively reduce a friction loss due to viscosity in a region other than a driving power transmitting portion. Since the material capable of revealing a high coefficient of friction is accumulated only in a contacting portion, it is possible to reveal various combinations of an oily medium with physical properties of the compound of the invention, and it is possible to inexpensively provide a combination satisfying many requirements of a transmission.

3.-1 Viscosity-Pressure Modulus

The smaller the viscosity-pressure modulus of the compound represented by the foregoing formula (I), the smaller the viscosity under a high pressure is relatively. The viscosity-pressure modulus of the foregoing compound at 40° C. is preferably not more than 20 $GPa^{-1}$, more preferably not more than 15 $GPa^{-1}$, and especially preferably not more than 10 $GPa^{-1}$. Though it is preferable that the viscosity-pressure modulus is small as far as possible, it has been elucidated that the viscosity-pressure modulus is correlative to the free volume of the molecule, and it may be conjectured that a lower limit value of the viscosity-pressure modulus of the organic compound under the foregoing condition is about 5 $GPa^{-1}$.

3.-2 Elementary Formulation:

The compound of the invention is preferably constituted of only carbon, hydrogen and oxygen. In general, the current lubricating oils contain phosphorus, sulfur and a heavy metal. In a lubricating oil to be used for a 2-stroke engine of combusting the lubricating oil together with a fuel, though it does not contain phosphorus and a heavy metal while taking into consideration the environmental load, it contains sulfur in an amount of about a half of a lubricating oil to be used for a 4-stroke engine. That is, in the current lubricating technologies, though it may be conjectured that the formation of a boundary lubricating film made of sulfur is essential at a minimum. In view of the fact that a sulfur element is contained, a load to a catalyst for exhaust gas cleaning is very large. In this catalyst for exhaust gas cleaning, though platinum and nickel are used, a poisoning action of phosphorus or sulfur is a serious problem. From this point of issue, a merit to be brought due to the fact that elements constituting a composition of the lubricating oil are composed of only carbon, hydrogen, oxygen and nitrogen is very large. In addition, the fact that the composition is composed of only carbon, hydrogen and oxygen is optimal for lubricating oils of industrial machines, in particular food manufacturing-related devices. According to the current technology, an elementary composition taking into consideration the environment while scarifying the coefficient of friction is adopted. This is also a very preferable technology for a lubricating oil for cutting or working a metal requiring a large amount of water for cooling. In many cases, the lubricating oil inevitably floats or vaporizes in the air as a mist, and a treatment waste fluid is discharged into the natural system. Therefore, in order to make both the lubricating properties and the environmental protection compatible with each other, it is very preferable to substitute the current lubricating oils with the composition of the invention which is constituted of only carbon, hydrogen and oxygen.

And not only lubricant oils but also any materials used in various applications are required to be an environmental harmony-type material, and the compound of the invention is fit for the purpose.

3.-3. Liquid Crystallinity:

The compound of the invention may be a liquid crystal compounds. From the viewpoint of lubricating performance, it is preferable that the compound of the invention exhibits liquid crystallinity. This is because in view of the fact that the compound reveals liquid crystallinity, the molecule is oriented in the sliding portion, and a lower coefficient of friction is revealed due to an effect of its anisotropic low viscosity (see, for example, Ken KAWATA and Nobuyoshi OHNO, *Fujifilm Research and Development* (No. 51-2006, pp. 80 to 85).

As for the liquid crystallinity, the compound of the invention may singly reveal thermotropic liquid crystallinity, or it may reveal thermotropic liquid crystallinity together with the oily medium.

4. Applications of Compound of the Invention

The compound of the invention can be used in various applications. One example is a lubricant. The compound of the invention can be used alone as a lubricant, or the embodiments of dispersion compositions or the like, of which the compound of the invention is dispersed and/or dissolved in an oily or aqueous medium, can be used as a lubricant. For example, it is fed between the two sliding surfaces and can be used for reducing the friction. The compound of the invention or the composition containing it is able to form a film on the sliding surface.

EXAMPLES

The invention is described in more detail with reference to the following Examples. In the following Examples, the amount of the material, reagent and substance used, their ratio, the operation with them and the like may be suitably modified or changed not overstepping the spirit and the scope of the invention. Accordingly, the scope of the invention should not be limited to the following Examples.

1. Synthesis Examples of Illustrative Compounds 1-1. Synthesis Example of Illustrative Compound AII-2

Synthesis of 1-docosanyl methanesulfonate 247.4 g of behenyl alcohol (1-docosanol) was dissolved in 640 mL of tetrahydrofuran, 116.1 mL of methanesulfonyl chloride was gradually added, and 64.7 mL of triethylamine was then added dropwise under ice cooling over 30 minutes. After stirring for one hour, the mixture was heated at 40° C. and further stirred for 30 minutes. The reaction mixture was poured into 3.5 L of ice water, and the resulting mixture was ultrasonically dispersed for 15 minutes and further stirred at room temperature for 4 hours. The dispersion was filtered under reduced pressure, and a crystal was washed with 2 L of water. The resulting white crystal was stirred in 1.5 L of acetonitrile for one hour, filtered under reduced pressure and then washed with 0.5 L of acetonitrile. The resulting crystal was dried under reduced pressure to obtain 303.4 g of a white crystal.

Synthesis of tetraethylene glycol mono-1-docosanyl ether 80.4 g of 1-docosanyl methanesulfonate was added to 207 mL of tetraethylene glycol, and the mixture was heated at 110° C. 40.0 g of t-butoxypotassium was gradually added over 2 hours. The mixture was further stirred for 3 hours, and after cooling, the reaction mixture was poured into 3 L of ice water, to which was then added 2 L of ethyl acetate, the mixture was stirred, and 22.2 g of an insoluble matter was filtered. An ethyl acetate phase was extracted and separated from the filtrate, after concentration under reduced pressure, 0.5 L of acetonitrile was added, and the mixture was stirred under ice cooling for one hour. The reaction mixture was filtered under reduced pressure and washed with 0.2 L of cold acetonitrile to obtain 81.6 g of a white crystal.

Synthesis of 3-(1-docosanyl tetraethyleneoxycarbonyl)propionic acid 25.0 g of tetraethylene glycol mono-1-docosanyl ether was dissolved in 160 mL of toluene, to which were then added 7.5 g of succinic anhydride and two drops of concentrated sulfuric acid, and the mixture was heated at 125° C. for 8 hours. After cooling, 0.3 L of acetonitrile was added, and the mixture was stirred under ice cooling for one hour and then filtered under reduced pressure. The reaction mixture was washed with 100 mL of cold acetonitrile and then dried under reduced pressure to obtain 23.3 g of a white crystal.

Synthesis of Illustrative Compound AII-2

5.0 g of 3-(1-docosanyl tetraethyleneoxycarbonyl)propionic acid was dissolved in 20 mL of toluene, two drops of dimethylformamide and 2 mL of thienyl chloride were then added thereto. After 5 minutes, the mixture was heated at 80° C. and further stirred for 2 hours, and after cooling, toluene and excessive thienyl chloride were distilled off under reduced pressure. 15 mL of toluene and 283 mg of pentaerythritol were added thereto, and 5 mL of pyridine was then gradually added. After heating at 80° C. for 8 hours, the reaction mixture was cooled, 200 mL of methanol was poured thereinto, and the mixture was stirred for 2 hours. The reaction mixture was filtered under reduced pressure to obtain 4.8 g of a white crystal.

1-2. Synthesis Example of Illustrative Compound AII-5

Illustrative Compound AII-5 was synthesized in the same manner, except for replacing 1-docosanol as the starting raw material of Illustrative Compound II-2 with 1-stearyl alcohol.

1-3. Synthesis Example of Illustrative Compound AII-8

Illustrative Compound AII-8 was synthesized in the same manner, except for replacing 1-docosanol as the starting raw material of Illustrative Compound AII-2 with 1-tetradecanol.

1-4. Synthesis Example of Illustrative Compound AII-1

Synthesis of 3-(1-docosanyl polyethyleneoxycarbonyl)propionic acid 25.6 g of polyethylene glycol mono-1-docosanyl ether (manufactured by Takemoto Oil & Fat Co., Ltd.; average degree of polymerization of ethyleneoxy group: 6.65) was dissolved in 160 mL of toluene, to which were then added 8.0 g of succinic anhydride and two drops of concentrated sulfuric acid, and the mixture was heated at 125° C. for 8 hours. After cooling, 0.3 L of acetonitrile was added, and the mixture was stirred under ice cooling for one hour and then filtered under reduced pressure. The reaction mixture was washed with 100 mL of cold acetonitrile and then dried under reduced pressure to obtain 22.3 g of a white crystal.

Synthesis of Illustrative Compound AII-1

5.18 g of 3-(1-docosanyl polyethyleneoxycarbonyl)propionic acid was dissolved in 10 mL of toluene, and two drops of dimethylformamide and 2 mL of thienyl chloride were then added thereto. After 5 minutes, the mixture was heated at 80° C. and further stirred for 2 hours, and after cooling, toluene and excessive thienyl chloride were distilled off under reduced pressure. 14 mL of toluene and 245 mg of pentaerythritol were added thereto, and 6 mL of pyridine was then added thereto. After heating at 80° C. for 8 hours, the reaction mixture was cooled, 200 mL of methanol was poured thereinto, and the mixture was stirred for 2 hours. The reaction mixture was filtered under reduced pressure to obtain 4.69 g of a white crystal.

1-5. Synthesis Example of Illustrative Compound AII-17

Illustrative Compound AII-17 was synthesized in the same manner, except for changing the average degree of polymerization of 6.65 of polyethylene glycol mono-1-dosanyl ether as the starting raw material of Illustrative Compound AII-1 to an average degree of polymerization of 10.30.

1-6. Synthesis Example of Illustrative Compound AII-18

Illustrative Compound AII-18 was synthesized in the same manner, except for changing the average degree of polymerization of 6.65 of polyethylene glycol mono-1-dosanyl ether as the starting raw material of Illustrative Compound AII-1 to an average degree of polymerization of 19.0.

1-7. Synthesis Example of Illustrative Compound AII-33

Illustrative Compound AII-33 was synthesized in the same manner, except for replacing succinic anhydride used in Illustrative Compound AII-1 with Meldrum's acid.

1-8. Synthesis Example of Illustrative Compound AII-34

Illustrative Compound AII-34 was synthesized in the same manner, except for replacing succinic anhydride used in Illustrative Compound AII-1 with glutaric anhydride.

1-9. Synthesis Example of Illustrative Compound AII-36

Illustrative Compound AII-36 was synthesized in the same manner, except for replacing succinic anhydride used in Illustrative Compound AII-1 with maleic anhydride.

1-10. Synthesis Example of Illustrative Compound AII-37

Illustrative Compound AII-37 was synthesized in the same manner, except for replacing succinic anhydride used in Illustrative Compound AII-1 with diglycolic anhydride.

1-11. Synthesis Example of Illustrative Compound AII-38

Illustrative Compound AII-38 was synthesized in the same manner, except for replacing succinic anhydride used in Illustrative Compound AII-1 with phthalic anhydride.

1-12. Synthesis Example of Illustrative Compound AII-40

Illustrative Compound AII-40 was synthesized in the same manner, except for replacing succinic anhydride used in Illustrative Compound AII-1 with 3,3-dimethylglutaric anhydride.

Various illustrative compounds were prepared in the similar manner as the above. Regarding some of them, their NMR spectra data, IR data and melting point are shown below.

Illustrative Compound AII-1:
$^1$H NMR (400 MHz, CDCl$_3$): δ4.24 (8H, t), 4.13 (8H, s), 3.65 (64H, m), 3.44 (8H, t), 2.64 (16H, dd), 1.58 (16H, t), 1.25 (160H, br), 0.88 (12H, t).
IR data (neat) cm$^{-1}$: 2924 (s), 2853 (s), 1739 (s), 1465 (s), 1350 (s), 1146 (s), 720 (m).
Melting point: 63.5-64.0 degrees Celsius.

Illustrative Compound AII-2:
$^1$H NMR (300 MHz, CDCl$_3$): δ4.24 (8H, t), 4.13 (8H, s), 3.65 (64H, m), 3.44 (8H, t), 2.65 (12H, br), 1.57 (8H, t), 1.25 (160H, br), 0.88 (12H, t).
IR data (neat) cm$^{-1}$: 2927 (s), 2854 (s), 1741 (s), 1464 (s), 1350 (m), 1146 (s), 720 (w).
Melting point: 64.7-65.2 degrees Celsius Illustrative Compound AII-3:
$^1$H NMR (400 MHz, CDCl$_3$): δ4.24 (8H, t), 4.13 (8H, s), 3.65 (72H, m), 3.44 (8H, t), 2.64 (16H, m), 1.57 (16H, t), 1.26 (144H, br), 0.88 (12H, t).
IR data (neat) cm$^{-1}$: (neat): 2924 (s), 2852 (s), 1738 (s), 1465 (s), 1350 (s), 1140 (b), 858 (m), 720 (m).
Melting point: 55.1-55.6 degrees Celsius Illustrative Compound AII-4:
$^1$H NMR (400 MHz, CDCl$_3$): δ4.24 (8H, t), 4.13 (8H, s), 3.65 (64H, m), 3.44 (8H, t), 2.63 (16H, m), 1.57 (8H, t), 1.25 (128H, br), 0.88 (12H, t).
IR data (neat) cm$^{-1}$: 2932 (s), 2859 (s), 1746 (s), 1465 (s), 1350 (s), 1156 (b), 856 (m), 720 (w).
Melting point: 46.0-47.0 degrees Celsius Illustrative Compound AII-5:
$^1$H NMR (400 MHz, CDCl$_3$): δ4.24 (8H, t), 4.13 (8H, s), 3.65 (64H, m), 3.44 (8H, t), 2.64 (16H, s), 1.57 (16H, t), 1.25 (120H, br), 0.88 (12H, t).
IR data (neat) cm$^{-1}$: 2924 (s), 2853 (s), 1740 (s), 1464 (s), 1350 (s), 1144 (s), 718 (m).
Melting point: 47.0-47.8 degrees Celsius Illustrative Compound AII-6:
$^1$H NMR (300 MHz, CDCl$_3$): δ4.24 (8H, t), 4.13 (8H, s), 3.65 (80H, m), 3.44 (8H, t), 2.64 (16H, d), 1.57 (16H, br), 1.25 (120H, br), 0.88 (12H, t).
IR data (neat) cm$^{-1}$: 2920 (s), 2852 (s), 1737 (s), 1458 (s), 1350 (s), 1105 (b), 862 (m), 719 (m).
Melting point: 35.3-35.8 degrees Celsius Illustrative Compound AII-7:
$^1$H NMR (300 MHz, CDCl$_3$): δ4.24 (8H, br), 4.13 (8H, s), 3.65 (80H, m), 3.44 (8H, t), 2.64 (16H, s), 1.57 (8H, br), 1.26 (96H, br), 0.88 (12H, t).
IR data (neat) cm$^{-1}$: 2925 (s), 2854 (s), 1740 (s), 1465 (m), 1350 (m), 1253 (s), 1147 (s).
Melting point: oil at a room temperature Illustrative Compound AII-8:
$^1$H NMR (300 MHz, CDCl$_3$): δ4.24 (8H, t), 4.13 (8H, s), 3.65 (60H, m), 3.44 (8H, t), 2.64 (16H, s), 1.59 (40H, br), 1.26 (96H, m), 0.88 (12H, t).
IR data (neat) cm$^{-1}$: 2927 (s), 2855 (s), 1740 (s), 1465 (m), 1350 (m), 1252 (s), 1152 (s), 1038 (m), 859 (w).
Melting point: 39.5-40.5 degrees Celsius Illustrative Compound AII-14:
$^1$H NMR (300 MHz, CDCl$_3$): δ4.24 (8H, t), 4.13 (8H, s), 3.65 (64H, m), 3.44 (8H, t), 2.64 (16H, m), 1.57 (8H, t), 1.25 (160H, br), 0.88 (12H, t).
IR data (neat) cm$^{-1}$: 2928 (s), 2854 (s), 1742 (s), 1465 (m), 1351 (s), 1250 (s), 1150 (s), 720 (w).
Melting point: 63.6-64.4 degrees Celsius Illustrative Compound AII-15:
$^1$H NMR (400 MHz, CDCl$_3$): δ4.24 (8H, t), 4.13 (8H, s), 3.65 (104H, m), 3.44 (8H, t), 2.64 (16H, m), 1.57 (8H, t), 1.25 (168H, br), 0.88 (12H, t).
IR data (neat) cm$^{-1}$: 2925 (s), 2853 (s), 1740 (s), 1465 (s), 1350 (s), 1147 (b), 865 (m), 720 (m).
Melting point: 61.9-62.9 degrees Celsius Illustrative Compound AII-16:
$^1$H NMR (300 MHz, CDCl$_3$): δ4.24 (8H, t), 4.13 (8H, s), 3.65 (120H, m), 3.44 (8H, t), 2.64 (16H, s), 1.57 (8H, br), 1.25 (160H, br), 0.88 (12H, t).
IR data (neat) cm$^{-1}$: 2925 (s), 2854 (s), 2361 (w), 1740 (s), 1558 (w), 1457 (w), 1250 (s), 1146 (b).
Melting point: 59.3-60.3 degrees Celsius Illustrative Compound AII-17:
$^1$H NMR (400 MHz, CDCl$_3$): δ4.23 (8H, t), 4.13 (8H, s), 3.64 (144H, m), 3.57 (8H, m), 3.44 (8H, t), 2.64 (16H, m), 1.57 (8H, t), 1.25 (160H, br), 0.88 (12H, t).
IR data (neat) cm$^{-1}$: 2925 (s), 2854 (s), 1741 (s), 1465 (m), 1351 (w), 1144 (s).
Melting point: 55.6-56.3 degrees Celsius Illustrative Compound AII-18:
$^1$H NMR (300 MHz, CDCl$_3$): δ4.24 (8H, t), 4.13 (8H, s), 3.64 (288H, m), 3.44 (8H, t), 2.64 (16H, m), 1.59 (32H, br), 1.25 (160H, br), 0.88 (12H, t).
IR data (neat) cm$^{-1}$: 2924 (s), 2854 (s), 1738 (s), 1459 (s), 1349 (s), 1250 (s), 1109 (b), 857 (m).
Melting point: 43.8-47.1 degrees Celsius Illustrative Compound AII-19:
$^1$H NMR (300 MHz, CDCl$_3$): δ4.24 (8H, t), 4.13 (8H, s), 3.64 (424H, m), 3.44 (16H, t), 2.64 (16H, m), 1.59 (40H, br), 1.25 (160H, br), 0.88 (12H, t).
IR data (neat) cm$^{-1}$: 2925 (s), 2856 (s), 1739 (s), 1460 (m), 1350 (s), 1296 (s), 1251 (s), 1119 (b), 946 (m), 857 (m).
Melting point: 46.4-47.4 degrees Celsius Illustrative Compound AII-33:
$^1$H NMR (400 MHz, CDCl$_3$): δ4.30 (8H, t), 4.21 (8H, s), 3.65 (72H, m), 3.45 (16H, m), 3.24 (8H, t), 1.57 (8H, t), 1.25 (160H, br), 0.88 (12H, t).
IR data (neat) cm$^{-1}$: 3481 (b), 2924 (s), 2853 (s), 1739 (s), 1648 (m), 1559 (w), 1465 (s), 1266 (b), 1129 (b), 1041 (s), 720 (m).
Melting point: 65.5-66.5 degrees Celsius Illustrative Compound AII-34:
$^1$H NMR (400 MHz, CDCl$_3$): δ4.23 (8H, m), 4.11 (8H, s), 3.65 (80H, m), 3.44 (8H, t), 2.41 (16H, t), 1.96 (8H, tt), 1.59 (8H, br), 1.25 (160H, br), 0.88 (12H, t).
IR data (neat) cm$^{-1}$: 3495 (b), 2930 (s), 2855 (s), 1740 (s), 1464 (s), 1351 (m), 1136 (s), 720 (w).
Melting point: 59.9-61.6 degrees Celsius Illustrative Compound AII-36:
$^1$H NMR (300 MHz, CDCl$_3$): δ6.88 (4H, d), 6.84 (4H, d), 4.33 (16H, m), 3.64 (64H, m), 3.44 (16H, t), 1.57 (8H, br), 1.25 (160H, br), 0.88 (12H, t).
IR data (neat) cm$^{-1}$: 2923 (s), 2853 (s), 1728 (s), 1465 (s), 1351 (m), 1292 (s), 1254 (s), 1146 (s), 769 (s), 720 (m).
Melting point: 60.2-61.5 degrees Celsius Illustrative Compound AII-37:

$^1$H NMR (300 MHz, CDCl$_3$): δ4.32 (8H, t), 4.27 (16H, s), 4.23 (8H, s), 3.72 (8H, m), 3.65 (80H, m), 3.44 (8H, t), 1.57 (8H, br), 1.25 (160H, br), 0.88 (12H, t).

IR data (neat) cm$^{-1}$: 2926 (s), 2854 (s), 1758 (s), 1465 (s), 1351 (m), 1204 (s), 1138 (s), 720 (m).

Melting point: 60.6-63.8 degrees Celsius

Illustrative Compound AII-38:

$^1$H NMR (300 MHz, CDCl$_3$): δ7.74 (8H, m), 7.54 (8H, m), 4.46 (8H, t), 3.91 (8H, s), 3.80 (8H, t), 3.64 (80H, m), 3.44 (8H, t), 1.64 (16H, br), 1.25 (152H, m), 0.88 (12H, t).

IR data (neat) cm$^{-1}$: 2925 (s), 2854 (s), 1733 (s), 1465 (w), 1287 (s), 1122 (s), 743 (w).

Melting point: 64.7-65.7 degrees Celsius

Illustrative Compound AII-40:

$^1$H NMR (400 MHz, CDCl$_3$): δ4.22 (8H, m), 4.09 (8H, s), 3.64 (72H, m), 3.44 (8H, t), 2.43 (8H, t), 1.56 (8H, br), 1.25 (160H, m), 1.09 (24H, s), 0.88 (12H, t)

IR data (neat) cm$^{-1}$: 2924 (s), 2853 (s), 1737 (m), 1465 (m), 1287 (m), 1123 (s).

Melting point: 53.1-53.7 degrees Celsius

Illustrative Compound AII-41:

$^1$H NMR (300 MHz, CDCl$_3$): δ4.50 (8H, s), 4.35 (8H, t), 3.67 (96H, m), 3.48 (8H, m), 1.58 (8H, br), 1.25 (160H, m), 0.88 (12H, t).

IR data (neat) cm$^{-1}$: 2927 (s), 2855 (s), 1780 (s), 1465 (m), 1246 (m), 1178 (s), 942 (m).

Melting point: 56.2-57.0 degrees Celsius

Illustrative Compound AII-43:

$^1$H NMR (300 MHz, CDCl$_3$): δ4.52 (8H, s), 4.46 (8H, t), 3.77 (8H, t), 3.64 (64H, m), 3.44 (8H, t), 1.74 (16H, br), 1.56 (8H, t), 1.25 (160H, m), 0.88 (12H, t).

IR data (neat) cm$^{-1}$: 2925 (s), 2853 (s), 1747 (m), 1631 (m), 1519 (s), 1479 (s), 1396 (s), 1323 (s), 1214 (b), 1119 (s), 721 (m).

Melting point: 55.4-56.4 degrees Celsius

Illustrative Compound AII-65:

$^1$H NMR (400 MHz, CDCl$_3$): δ4.24 (8H, t), 4.14 (8H, s), 3.64 (88H, m), 3.56 (8H, t), 3.32 (8H, d), 2.64 (16H, d), 1.59 (40H, br), 1.26 (84H, br), 0.85 (76H, m), 0.75 (12H, t).

IR data (neat) cm$^{-1}$: 2955 (s), 2926 (s), 2858 (s), 1737 (s), 1460 (s), 1378 (s), 1349 (s), 1248 (s), 1105 (s), 1038 (s), 861 (m).

Melting point: oil at a room temperature

Illustrative Compound AII-88:

$^1$H NMR (400 MHz, CDCl$_3$): δ4.24 (8H, t), 4.14 (8H, s), 3.64 (88H, m), 3.56 (8H, t), 3.32 (8H, d), 2.64 (16H, d), 1.59 (40H, br), 1.26 (84H, br), 0.85 (76H, m), 0.75 (12H, t).

IR data (neat) cm$^{-1}$: 2955 (s), 2926 (s), 2858 (s), 1737 (s), 1460 (s), 1378 (s), 1349 (s), 1248 (s), 1105 (s), 1038 (s), 861 (m).

Melting point: oil at a room temperature

Illustrative Compound AII-89:

$^1$H NMR (400 MHz, CDCl$_3$): δ4.24 (8H, t), 4.14 (8H, s), 3.64 (88H, m), 3.56 (8H, t), 3.32 (8H, d), 2.64 (16H, d), 1.59 (40H, br), 1.26 (84H, br), 0.85 (76H, m), 0.75 (12H, t).

IR data (neat) cm$^{-1}$: 2955 (s), 2926 (s), 2858 (s), 1737 (s), 1460 (s), 1378 (s), 1349 (s), 1248 (s), 1105 (s), 1038 (s), 861 (m).

Melting point: oil at a room temperature

Illustrative Compound AII-90:

$^1$H NMR (400 MHz, CDCl$_3$): δ4.24 (8H, t), 4.14 (8H, s), 3.64 (88H, m), 3.56 (8H, t), 3.32 (8H, d), 2.64 (16H, d), 1.59 (40H, br), 1.26 (84H, br), 0.85 (76H, m), 0.75 (12H, t).

IR data (neat) cm$^{-1}$: 2955 (s), 2926 (s), 2858 (s), 1737 (s), 1460 (s), 1378 (s), 1349 (s), 1248 (s), 1105 (s), 1038 (s), 861 (m).

Melting point: oil at a room temperature

2. Test Example 1

Evaluation of Compound

As for the Illustrative Compounds and Comparative Compounds, a lubricating characteristic was evaluated using Optimol's reciprocating friction and wear tester (SRV) under the following condition.

Evaluation and Measurement Methods by Reciprocating (SRV) Friction and Wear Test:

A coefficient of friction was evaluated using a reciprocating (SRV) friction and wear tester under the following test condition.

Test piece (friction material): SUJ-2

Plate: 24 mm in diameter×7 mm in thickness, surface roughness: 0.45 to 0.65 μm

Cylinder: 15 mm in diameter×22 mm in width, surface roughness: up to 0.05 μm

Temperature: 30 to 150° C.

Load: 50 N, 75 N, 100 N, 200 N and 400 N

Amplitude: 1.5 mm

Frequency: 50 Hz

Time change pattern of temperature and load

The temperature was initially set up at 90° C., and after keeping for a certain period of time, it was dropped to the neighborhood of a melting point of each raw material by 10° C. at intervals of ten minutes. Thereafter, the temperature was similarly increased to 150° C. and further dropped to 50° C.

The pressure (load) was changed in a manner of 50 N→75 N→100 N→200 N→400 N→50 N at intervals of one minute twice at 90° C. and once at 120° C. and 150° C., respectively.

The illustrative compounds used for the evaluation are AII-1, 2, 17, 18 and 65. Moreover, as the comparative compounds, alkyleneoxy group-free pentaerythritol tetrastearate $(C(CH_2OCOC_{17}H_{35}\text{-n})_4$: Comparative Compound C-1) and $C\{CH_2O(C_2H_4O)_{6.5}C_{22}H_{45}\text{-n}\}_2$ (Comparative Compound C-2), the both of which are a compound generally used as a lubricant, were used, respectively.

The measurement results are shown in FIGS. 1 to 4.

On review of the measurement results shown in FIGS. 1 to 4, it can be understood that Illustrative Compounds AII-1, AII-2, AII-17, AII-18 and AII-65 are conspicuously small in the coefficient of friction as compared with Comparative Compounds C-1 and C-2.

It is noted that in all of Illustrative Compounds AII-1, AII-2, AII-17, AII-18 and AII-65 of the formula (Z), the coefficient of friction abruptly increases in the vicinity of the melting point at the time of first temperature drop. It may be conjectured that this is an increase of the coefficient of friction to be caused due to an abrupt increase of the viscosity getting close to the melting point. Moreover, it may be considered that in view of the fact that the coefficient of friction does not depend upon a change of the viscosity so much in the subsequent temperature increase and temperature drop processes, the material is in a fluid lubricating state in a low temperature region in the vicinity of the melting point, whereas it is an elastic fluid lubrication region at a temperature higher than that temperature.

On the other hand, in all of Comparative Compounds C-1 and C-2, the melting point is not higher than 60° C., an increase of the coefficient of friction is seen in the vicinity thereof, and the coefficient of friction is not influenced by a change of the temperature at a temperature higher than that temperature. It may be considered that these compounds undergo frictional sliding in a region of from fluid lubrication to elastic fluid lubrication similarly to the foregoing illustrative compounds.

In Illustrative Compound AII-65 having the lowest viscosity among these compounds, it can be understood that the coefficient of friction exhibits distinct positive temperature dependency, and it may be considered from the Stribeck curve that it is suggested that AII-65 relatively contributes to mixed lubrication.

Since all of other compounds than Illustrative Compound AII-65 exhibit a similar melting point, it is safe to consider that the viscosity of these compounds is also similar. So, in view of the fact that the coefficients of friction of Illustrative Compounds AII-1, AII-2, AII-17, AII-18 and AII-65 are conspicuously different from the coefficients of friction of Comparative Compounds C-1 and C-2, it may be considered from the Barus equation: $\eta=\eta_0 \exp(\alpha P)$, which expresses the pressure dependency of viscosity, there is a significant difference in the viscosity $\eta$ under a high pressure P in an elastic fluid lubrication region, namely a viscosity-pressure modulus $\alpha$. This is one of the characteristic features of the group of compounds of the invention.

Moreover, results obtained by evaluating a wear depth of the sliding part of the test piece after the frictional sliding test of each of the compounds using a laser microscope are shown below.

TABLE 1

| Compound No. | Wear Depth [μm] |
|---|---|
| Illustrative Compound AII-1 | 0.07 |
| Illustrative Compound AII-2 | 0.05 |
| Illustrative Compound AII-17 | 0.03 |
| Illustrative Compound AII-18 | 0.02 |
| Illustrative Compound AII-65 | 0.08 |
| Compound C-1 for comparative Example | 0.25 |
| Compound C-2 for comparative Example | 0.32 |

The following can be understood from the results shown in the table.

When the illustrative compounds of the formula (Z) were utilized, the wear depth was extremely shallow, and a sliding scar itself was not substantially observed. On the other hand, when the comparative compounds were utilized, a distinct sliding scar was observed in all of the cases. That is, as for the wear depth, there was generated a distinct difference between the illustrative compounds and the comparative compounds.

3. Test Example 2

Evaluation of Oily Medium Dispersion Composition

As for the compositions of the invention and the comparative compositions, a lubricating characteristic was evaluated using Optimol's reciprocating friction and wear tester (SRV) under the following condition.
Evaluation and Measurement Methods by Reciprocating (SRV) Friction and Wear Test:
A coefficient of friction and wear resistance were evaluated using a reciprocating (SRV) friction and wear tester, and a friction and wear test was carried out under the following test condition.
Lubricant composition:
SUPER OIL N-32 (manufactured by Nippon Oil Corporation) which is a mineral oil was used as an oily medium, to which was then added Illustrative Compound AII-1 in a concentration of 1.0% by mass; the mixture was heated to 70° C. to form a transparent solution; and after air cooling for 10 minutes, this composition was tested under the following condition. This composition became cloudy step-by-step at the time of air cooling.
Test piece (friction material): SUJ-2
Plate: 24 mm in diameter×7 mm in thickness, surface roughness: 0.45 to 0.65 μm
Cylinder: 15 mm in diameter×22 mm in width, surface roughness: up to 0.05 μm
Temperature: 25 to 110° C.
Load: 50 N, 75 N, 100 N, 200 N and 400 N
Amplitude: 1.5 mm
Frequency: 50 Hz
Test method:
About 60 mg of the sample composition was placed in a portion where the cylinder slid on the plate and subjected to frictional sliding according to the following steps, thereby evaluating a coefficient of friction at each temperature and each load, and the following steps were repeated until a substantially constant pattern was obtained. After the completion, a wear depth of the plate was evaluated by a laser microscope.

Similarly, SUPER OIL N-32 (manufactured by Nippon Oil Corporation) which is a mineral oil was used as an oily medium, to which was then added each of the following illustrative compounds in a concentration of 1.0% by mass in place of Illustrative Compound AII-1, thereby evaluating the dependency of the coefficient of friction on temperature, pressure and lapsing time. Among the test sample compositions, as for sample compositions prepared using each of Illustrative Compounds AII-1, 3, 4, 5, 6, 7, 8, 14, 16, 17, 18, 19, 33, 34, 36, 37, 38, 40, 41, 42, 43, 65, 88, 89 and 90, the results are shown in respective graphs shown in FIGS. 5 to 17.

Moreover, compositions were similarly prepared using, as a comparative compound, each of compounds which are a pentaerythritol derivative but do not contain a polyalkyleneoxy group, specifically Comparative Compound C-3 ($C(CH_2OCOC_2H_4CO_2C_{22}H_{45}-n)_4$) and Comparative Compound C-6 ($C(CH_2OCOC_{17}H_{35}-n)_4$) and tested. The rest results are shown in a graph shown in FIG. 18.

Moreover, as a referential example, only SUPER OIL N-32 used as an oily medium, which is a mineral oil, was similarly tested. The results are shown in a graph shown in FIG. 19.

As shown in FIG. 5, it can be understood that the sample prepared utilizing Illustrative Compound AII-1 exhibits a low friction of friction such that the coefficient of friction at 25° C. is not more than 0.05. As shown in FIG. 1, since Illustrative Compound AII-1 is singly a crystal having a melting point of from 63.5 to 64.0° C., its coefficient of friction of SRV at 25° C. was 0.3 or more because of its high viscosity. Moreover, as shown in FIG. 19, SUPER OIL N-32 used as an oily medium, which is a mineral oil, singly exhibits a coefficient of friction at 25° C. of 0.07 or more. From this fact, it may be considered that in a state where Illustrative Compound AII-1 is dispersed in a concentration of 1.0% by mass in SUPER OIL N-32, the both do not work singly but mutually work as some kind of interaction, thereby revealing this small coefficient of friction.

In general, if a low-viscosity fluid and a high-viscosity fluid are present in the vicinity of an interface and produce a high shear field, the matter that the high-viscosity fluid forms a smooth coating film by shear in the vicinity of the harder interface, and the low-viscosity fluid is interposed in a gap between the both interfaces, thereby revealing a lower coefficient of friction conforms with the reason of lubrication, and it is suggested that such a phenomenon occurs.

In the sample containing Illustrative Compound AII-1, the coefficient of friction abruptly increases to 0.09 with an increase of the temperature, and that coefficient of friction is kept in the range of from 60 to 110° C. without utterly depending upon the temperature. It may be supposed that this is caused due to the fact that this lubrication state resides in elastic fluid lubrication but not boundary lubrication. This is because as shown in FIG. 19, the coefficient of friction of SUPER OIL N-32 which is a fluid with lower viscosity exhibits distinct positive temperature dependency, and it is strongly suggested that SUPER OIL N-32 slides in a mixed lubrication region; and therefore, it is hardly considered that SUPER OIL N-32 abruptly comes into the boundary lubrication in a field where a fluid with higher viscosity coexists.

As shown in FIGS. 5 to 17, as for the samples prepared utilizing other illustrative compounds, the same behavior as that in Illustrative Compound AII-1 was observed.

On the other hand, it can be understood that all of the compositions prepared utilizing Comparative Compounds C-3 and C-6, respectively are high in the coefficient of friction as compared by the compositions prepared utilizing each of the illustrative compounds.

A measurement value of a wear scar depth of the sliding part of each of the samples after the frictional sliding test is shown below. In this connection, Comparative Compound C-4 is $C\{CH_2O(C_2H_4O)_{6.5}C_{22}H_{45}\text{-n}\}_2$.

TABLE 2

| Material No. | Wear Depth [μm] |
|---|---|
| AI-1 | 0.33 |
| AI-2 | 0.25 |
| AI-3 | 0.23 |
| AI-4 | 0.14 |
| AI-5 | 0.13 |
| AI-6 | 0.28 |
| AI-7 | 0.45 |
| AI-8 | 0.22 |
| AI-12 | 0.18 |
| AI-15 | 0.09 |
| AI-22 | 0.34 |
| AI-26 | 0.28 |
| AI-30 | 0.41 |
| AI-32 | 0.33 |
| AI-34 | 0.25 |
| AI-55 | 0.24 |
| AI-58 | 0.14 |
| AI-68 | 0.53 |
| AI-71 | 0.15 |
| AI-76 | 0.20 |
| AII-1 | 0.08 |
| AII-2 | 0.13 |
| AII-3 | 0.13 |
| AII-4 | 0.09 |
| AII-5 | 0.07 |
| AII-6 | 0.08 |
| AII-7 | 0.14 |
| AII-8 | 0.07 |
| AII-15 | 0.25 |
| AII-16 | 0.14 |
| AII-17 | 0.06 |
| AII-18 | 0.07 |
| AII-19 | 0.12 |
| AII-21 | 0.21 |
| AII-23 | 0.09 |
| AII-24 | 0.16 |
| AII-33 | 0.11 |
| AII-34 | 0.13 |
| AII-35 | 0.23 |
| AII-36 | 0.22 |
| AII-37 | 0.12 |
| AII-38 | 0.11 |
| AII-39 | 0.07 |
| AII-40 | 0.11 |
| AII-41 | 0.13 |
| AII-42 | 0.10 |
| AII-43 | 0.19 |
| AII-48 | 0.14 |
| AII-49 | 0.32 |
| AII-50 | 0.22 |
| AII-54 | 0.23 |
| AII-57 | 0.24 |
| AII-59 | 0.33 |
| AII-60 | 0.23 |
| AII-64 | 0.22 |
| AII-65 | 0.14 |
| AIII-1 | 0.09 |
| AIII-2 | 0.09 |
| AIII-7 | 0.21 |
| Comparative Example C-3 | 0.69 |
| Comparative Example C-4 | 0.98 |
| Comparative Example C-6 | 1.23 |
| Mineral Oil (N-32) | 1.07 |

It can be understood that the samples of the Examples containing the compound of the invention are markedly shallow in the wear scar and excellent in the wear resistance as compared with those of the Comparative Examples.

In this connection, as compared with the wear scar depths of Test Example 1, the results of Test Example 2 generally exhibit large values. That appears to be very natural because in Test Example 2, the compound is used singly for the sample so that elastic fluid lubrication in an approximately thick film thickness is revealed, whereas in the present test example, only 1% by mass of the compound is contained in SUPER OIL N-32 as a low-viscosity oil. In addition, since the foregoing results include an example giving the same results as those obtained under the non-dilution condition of Test Example 1, it can be understood that the compositions of the Examples of the invention also have excellent properties regarding the wear resistance.

4. Test Example 3

Compositions were similarly prepared by using each of a commercially available poly-α-olefin (manufactured by Nippon Oil Corporation), a polyol ester (POE), a commercially available fluid and N-methylpyrrolidone as the oily medium in place of SUPER OIL N-32 which is a mineral oil and adding Illustrative Compound AII-4 in a concentration of 1.0% by mass thereto and then evaluated for the dependency of the coefficient of friction on temperature, pressure and lapsing time in the same manner as in Test Example 2. The results are shown in respective graphs shown in FIGS. 20 to 21.

From the results shown in FIGS. 20 to 21, it can be understood that even compositions prepared using any material as the oily medium exhibit a low coefficient of friction.

5. Test Example 4

A reciprocating (SRV) friction and wear test was carried out under the following condition. However, the evaluation was conducted on polyetheretherketone as a resin and aluminum oxide as a ceramic as other raw material than steel. A coefficient of friction and wear resistance were evaluated using a reciprocating (SRV) friction and wear tester, and a friction and wear test was carried out under the following test condition.

Preparation of Sample

SUPER OIL N-32 (manufactured by Nippon Oil Corporation) which is a mineral oil was used as a base oil, to which was then added Illustrative Compound AII-1 in a concentration of 1.0% by mass, and the mixture was heated to 70° C. to form a transparent solution, followed by air cooling for 10 minutes, thereby obtaining a dispersion composition for sample. This sample became cloudy step-by-step at the time of air cooling.

Test Condition:

The above-prepared sample was tested under the following condition.
  Test piece (friction material): SUJ-2
  Cylinder: 15 mm in diameter×22 mm in width, surface roughness: up to 0.05 μm
  Plate: 24 mm in diameter×7 mm in thickness, surface roughness: 0.45 to 0.65 μm
  Temperature: 30 to 180° C.
  Load: 50 N, 75 N, 100 N, 200 N and 400 N
  Amplitude: 1.5 mm
  Frequency: 50 Hz Test Method:

About 60 mg of the foregoing sample was placed in a portion where the cylinder slid on the plate and subjected to frictional sliding according to the following steps, thereby evaluating a coefficient of friction at each temperature and each load.

(1) A coefficient of friction with time is measured until a fluctuation of a value of the coefficient of friction at 30° C. under 50 N for 10 minutes becomes not more than 0.01.
(2) The sample is heated under 50 N by increasing the temperature from 30° C. to 110° C. at intervals of 10° C., thereby measuring a coefficient of friction at each temperature.
(3) The same is cooled to 30° C.
(4) (30 minutes after starting the cooling), a coefficient of friction is measured at 30° C. under 50 N, 75 N, 100 N, 200 N and 400 N, respectively.
(5) The sample is heated by increasing the temperature from 30° C. to 110° C. at intervals of 10° C., thereby measuring a coefficient of friction at each temperature.
However, a coefficient of friction is measured at each of 60° C. and 90° C. under 50 N, 75 N, 100 N, 200 N and 400 N, respectively.
(6) (3) to (6) are repeated until a difference of the coefficient of friction at 70° C. or higher from the last is not substantially found.
(7) The sample is cooled to 30° C.
(8) (30 minutes after starting the cooling), the temperature is increased from 30° C. to 180° C. at intervals of 10° C., thereby measuring a coefficient of friction at each temperature.
However, a coefficient of friction is measured at each of 60° C., 90° C., 120° C., 150° C. and 180° C. under 50 N, 75 N, 100 N, 200 N and 400 N, respectively.
(9) (5) and (6) are conducted, thereby finishing the operations.

The dependency of the coefficient of friction on temperature and pressure having become constant was evaluated with respect to each of a plate made of steel (SUJ-2), a plate obtained by forming a DLC thin film on steel by a CVD method, a plate made of polyetheretherketone and a plate made of aluminum oxide.

Plate 1: 24 mm in diameter×7 mm in thickness, material quality: diamond-like carbon, film thickness: 35 nm, surface roughness: not more than 0.01 μm
  Plate 2: 24 mm in diameter×7 mm in thickness, material quality: polyetheretherketone, surface roughness: up to than 0.05 μm
  Plate 3: 24 mm in diameter×7 mm in thickness, material quality: aluminum oxide, surface roughness: up to than 0.15 μm The results of the foregoing test are shown in FIG. 22. From the results shown in FIG. 22, it can be understood that the coefficient of friction increases in the order of DLC (diamond-like carbon)<PEEK<Fe (SUJ-2)<aluminum oxide at a low temperature. However, in this region, the film of Illustrative Compound AII-1 is much more hard, so that it may be conjectured that the mineral oil N-32 used as a base oil reveals fluid lubrication in a gap relative to the thin film of Illustrative Compound AII-1. If this conjecture is agreeable, it may be considered that this difference in the coefficient of friction is one reflecting the film thickness of the fluid film of the mineral oil N-32 to be caused by Illustrative Compound AII-1 existing on the interface, in its turn, the surface roughness of a base thereof. From a region where the temperature exceeds 100° C., a lowering of the coefficient of friction of each of the SUJ-2 and aluminum oxide plates is seen. However, in this region, Illustrative Compound AII-1 is in an elastic fluid lubrication region, and it may be conjectured that an influence of the surface roughness of the interface base is also revealed here together with the effect of elastic deformation. The diamond-like carbon coating film was separated on the way because the adhesion to steel was not sufficient. However, it is evident that all of the samples give a low coefficient of friction as compared with that obtained using the current lubrication technologies.

6. Test Example 5

As for a phenomenon in which Illustrative Compound AII-1 of the invention is segregated in the sliding part, the present inventor spectrally observed a neighborhood of a point-contacting portion of an instrument using a point contact EHL evaluation apparatus for evaluating an elastic fluid lubrication region in the technical field of tribology and succeeded in quantitatively grasping a change of material concentration at a high load in a high shear field. Specifically, the observation was carried out in the following manner.

Preparation of Sample

First of all, Illustrative Compound AII-1 was dispersed in an oily medium to prepare a sample. SUPER OIL N-32 (manufactured by Nippon Oil Corporation) which is a mineral oil was used as the oily medium, to which was then added Illustrative Compound AII-1 in a concentration of 1.0% by mass, and the mixture was heated to 70° C. to form a transparent solution, followed by air cooling for 10 minutes, thereby obtaining a dispersion composition for sample. Thereafter, this sample was tested under the following condition. In this connection, this sample became cloudy step-by-step at the time of air cooling.

Outline of Measurement Method:

FIG. 23 is a diagrammatic view of an apparatus used for this measurement. For micro FT-IR, MICRO20 connected to FT-IR400, manufactured by JASCO Corporation was used, and the apparatus was positioned such that the point-contacting portion of the point contact EHL evaluation apparatus was located in a working distance of a Cassegrain mirror thereof.

A rotating steel ball was placed on a diamond (hard plane) plate while making its rotation axis parallel, and a load was applied to the axis, thereby bringing them into press contact with each other. The prepared sample was fed and flown in a gap between the rotating steel ball and the diamond plate and its neighborhood.

Though a Newtonian ring which is an optical interference pattern is formed in a portion where the steel ball comes into point contact with the diamond plate, by irradiating infrared rays from the opposite side to the steel ball via the diamond plate and reflecting them on the steel ball, an IR spectrum of a thin film of the sample in the vicinity of the Newtonian ring can be measured. FIG. 24 shows a figure of the Newtonian ring formed by the point contact. A size of the Newtonian ring shown in FIG. 24 is about 200 μm, and a portion surrounded by a dotted line is an IR measurement light confined into a square of 160 μm.

When a mineral oil or a poly-α-olefin is used as the oily medium at the time of preparing a sample, since such a material is a hydrocarbon, there is no characteristic absorption other than those of C—C and C—H. In consequence, since Illustrative Compound AII-1 in the sample has a carbonyl group of an ester bond exhibiting a distinct high-intensity characteristic absorption band, a change of the concentration can be quantitatively detected from the intensity of the characteristic absorption band.

As a result of observation using the foregoing apparatus, it was noted that in a so-called Hertzian area under a high pressure in a high shear field, where a Newtonian ring is formed, Illustrative Compound II-1 was gradually segregated in a form of a candle flame formed by partition of a flow of the sample in, for example, a region of from 20 to 400 μm backward.

FIG. 25 is a figure showing a portion wherein a Newtonian ring is formed upon point contact, a portion where a sample flows thereinto, and right and left portions thereof.

FIG. 26 is an IR spectrum thereof. From the results shown in FIG. 26, it can be understood that a stretching vibration band of a carbonyl group at 1,750 cm$^{-1}$ and a stretching vibration band of ester C—O at 1,120 cm$^{-1}$ increase with time.

In many cases, the concentration becomes substantially constant for about 5 minutes to 2 hours under a condition at a measurement temperature of 40° C. at a linear velocity of 0.15 m/sec under a Hertzian pressure of 0.3 GPa, an aspect of which is, however, different depending upon a condition such as a temperature, etc.

FIG. 27 is a graph showing the temperature dependency of an absorbance. Obviously, it is noted that as a sample becomes close to a clearing point, namely a dispersion particle size of Illustrative Compound AII-1 becomes small, a segregation rate of Illustrative Compound AII-1 also becomes small, a segregation amount of which is not more than a measurement limit in this evaluation apparatus at a temperature of the clearing point or higher.

FIG. 28 is a graph showing a relation between a rotation speed of a steel ball, namely an amount at which a lubricating oil thereof is sent into a point-contacting portion and a segregation amount. As expected, it can be understood from this graph that the higher the rotation number, namely the larger the amount of a dispersion composition sample to be fed into the point-contacting portion, the more the segregation amount increases.

The foregoing point contact EHL evaluation apparatus is a model of the Hertzian contact area under a high-pressure and high-shear condition, namely a true contact site. The actual friction contact area is an area where such true contact areas are crowded. Therefore, it may be considered that in a sample containing Illustrative Compound AII-1 in the oily medium, the amount of the base oil with relatively low viscosity (oily medium) becomes small in the vicinity of a number of true contact areas of such a friction contact area, whereby the foregoing Illustrative Compound AII-1 is accumulated.

In consequence, even when the amount of Illustrative Compound AII-1 contained in the sample is small as about 1% by mass, and even under a condition under which there is a concern that originally, a compound is not accumulated at a high temperature, it can be expected that if the concentration of Illustrative Compound AII-1 is increased in the sliding portion, a low-viscosity effect is revealed under elastic fluid lubrication which is original to the subject compound even at the high temperature, as indicated by the frictional coefficient at the high temperature in an SRV evaluation apparatus.

7. Test Example 6

Performance Evaluation of Grease Composition:

Grease samples 1 to 5 each having a formulation shown in the following table were prepared using Illustrative Compounds AII-18, AI-64, AII-37, AI-71 and AIII-1, respectively. Moreover, comparative grease samples C1 to C4 each having a formulation shown in the following table were prepared, respectively.

A friction test was carried out, thereby measuring a coefficient of friction and a wear scar depth. In this connection, the coefficient of friction in the Examples was measured using a reciprocating friction tester (SRV friction and wear tester), and the friction test was carried out under the following test condition. The results of grease samples 1 to 5 of the Examples are shown in the following Table 3, and the results of the comparative grease samples C1 to C4 are shown in the following Table 4.

Test Condition:
The test condition was adopted by the ball-on-plate system.
Test piece (friction material): SUJ-2
Plate: ϕ24×6.9 mm
Ball: ϕ10 mm
Temperature: 70° C.
Load: 100 N
Aptitude: 1.0 mm
Frequency: 50 Hz
Test time: Measured 30 minutes after starting the test

TABLE 3

| | Grease Sample No. | | | | |
|---|---|---|---|---|---|
| | 1 | 2 | 3 | 4 | 5 |
| Compound of the Invention | AII-18 | AI-64 | AII-37 | AI-71 | AIII-1 |
| % by mass | 3 | 5 | 3 | 5 | 3 |
| Base Oil % by mass | | | | | |
| Mineral Oil *1 | 70 | 75 | 80 | — | — |
| Poly-α-olefin *2 | — | — | — | 82 | 82 |
| Thickener % by mass | | | | | |
| Lithium stearate | 27 | 20 | — | — | — |
| Urea *3 | — | — | 17 | 13 | 15 |
| Mixed consistency (40 degrees Celsius) | 288 | 265 | 274 | 251 | 299 |
| Friction Coefficient | 0.055 | 0.085 | 0.060 | 0.084 | 0.069 |
| Wear Depth (μm) | 0.35 | 0.58 | 0.53 | 0.71 | 0.56 |

*1 Viscosity 11 cst (100 degrees Celsius)
*2 Viscosity 12 cst (100 degrees Celsius)
*3 Product obtained by reacting 1 equivalent amount of diphenyl methane 4,4'-diisocyanate with 2 equivalent amounts of octadecyl amine.

TABLE 4

| | Grease Sample for Comparative Example No. | | | |
|---|---|---|---|---|
| | C1 | C2 | C3 | C4 |
| Compound of the Invention Base Oil % by mass | — | — | — | — |
| Mineral Oil *1 | 75 | — | 85 | — |
| Poly-α-olefin *2 | — | 75 | — | 85 |
| Thickener % by mass | | | | |
| Lithium stearate | 25 | 25 | — | — |
| Urea *3 | — | — | 15 | 15 |
| Mixed consistency (40 degrees Celsius) | 320 | 317 | 311 | 307 |
| Friction Coefficient | 0.127 | 0.135 | 0.132 | 0.145 |
| Wear Depth (μm) | 1.24 | 1.44 | 1.22 | 1.53 |

*1 Viscosity 11 cst (100 degrees Celsius)
*2 Viscosity 12 cst(100 degrees Celsius)
*3 Product obtained by reacting 1 equivalent amount of diphenyl methane 4,4'-diisocyanate with 2 equivalent amounts of octadecyl amine.

From the results shown in the foregoing tables, it can be understood that the grease composition samples of the Examples containing the compound of the invention conspicuously exhibit a friction reducing effect and a wear inhibiting effect.

Figure 1:
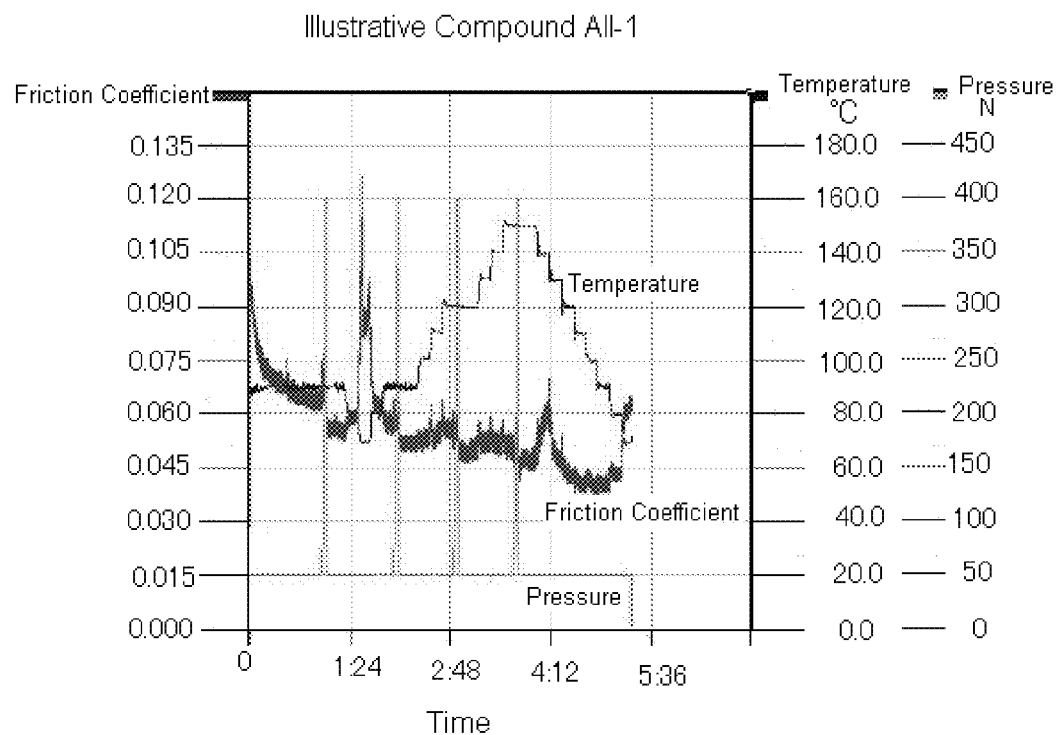
FIG. 1 is a graph showing the results of Test Example 1 of Illustrative Compounds AII-1 and AII-2.
Figure 1:
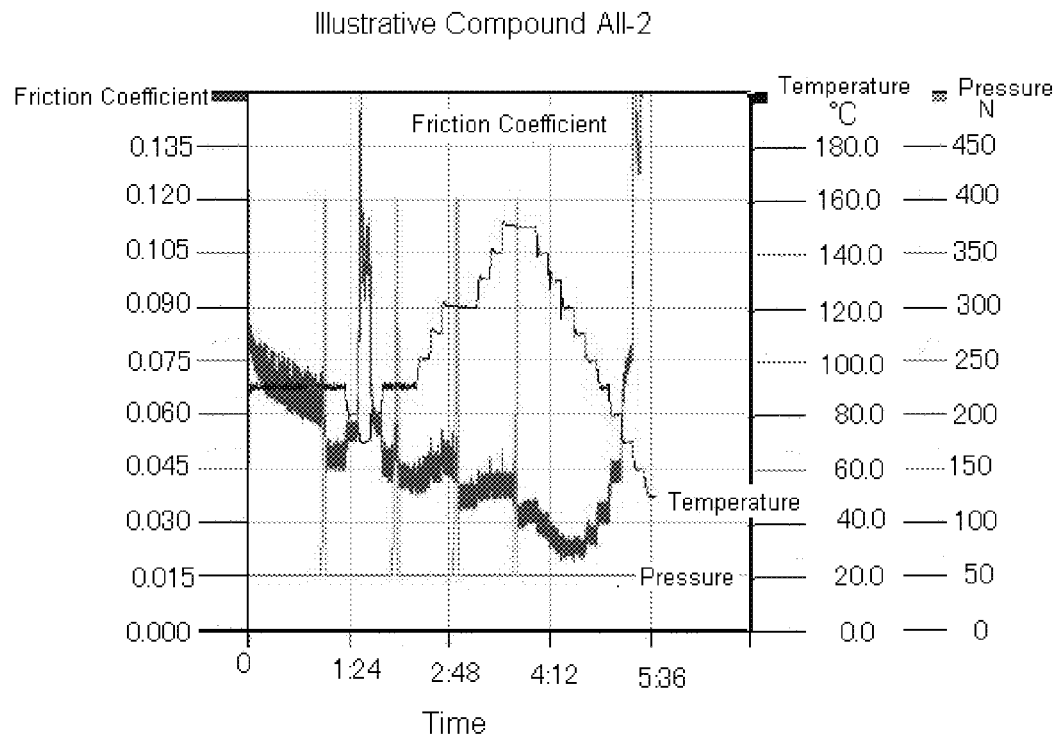
Figure 2:
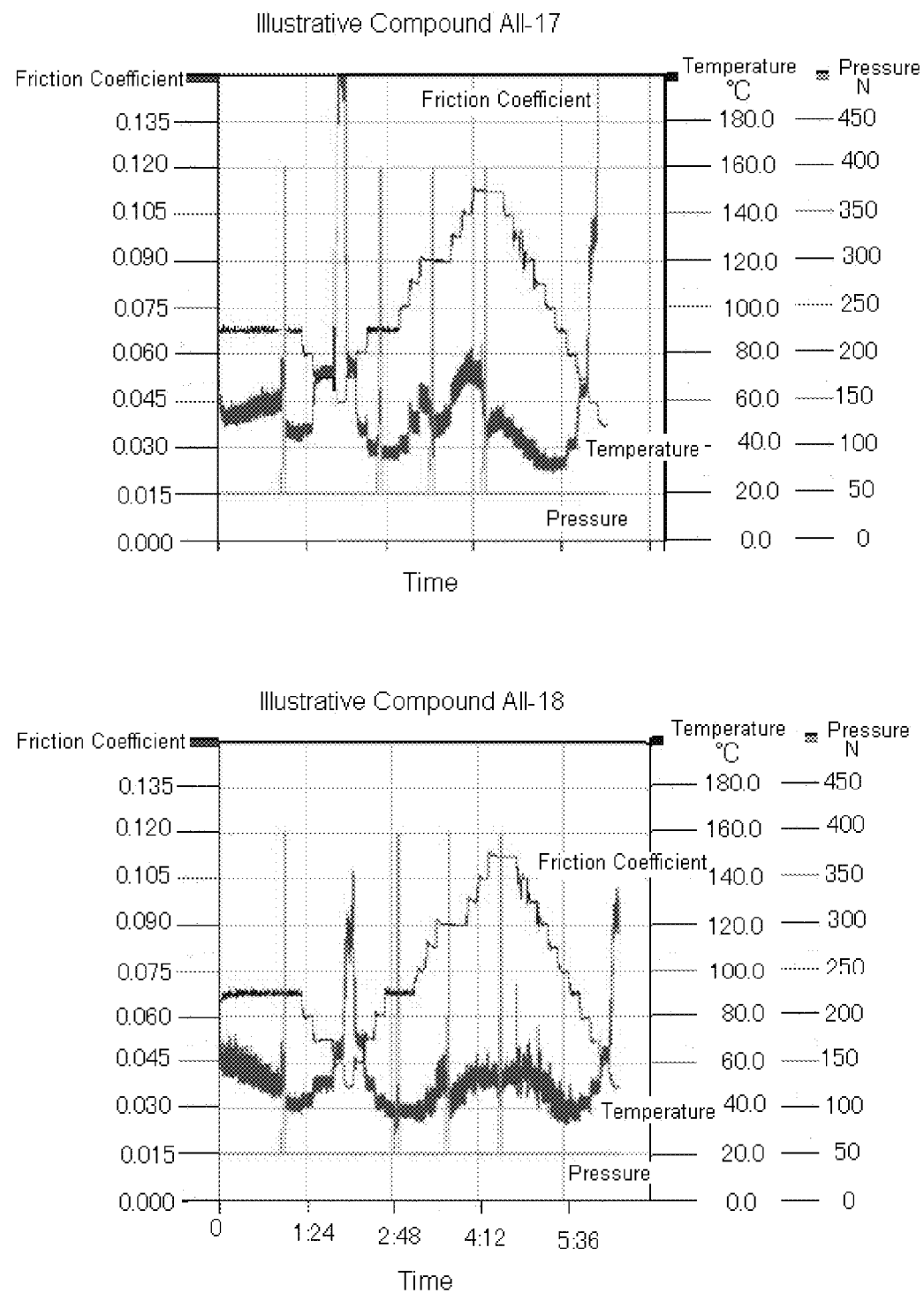
FIG. 2 is a graph showing the results of Test Example 1 of Illustrative Compounds AII-17 and AII-18.
Figure 3:
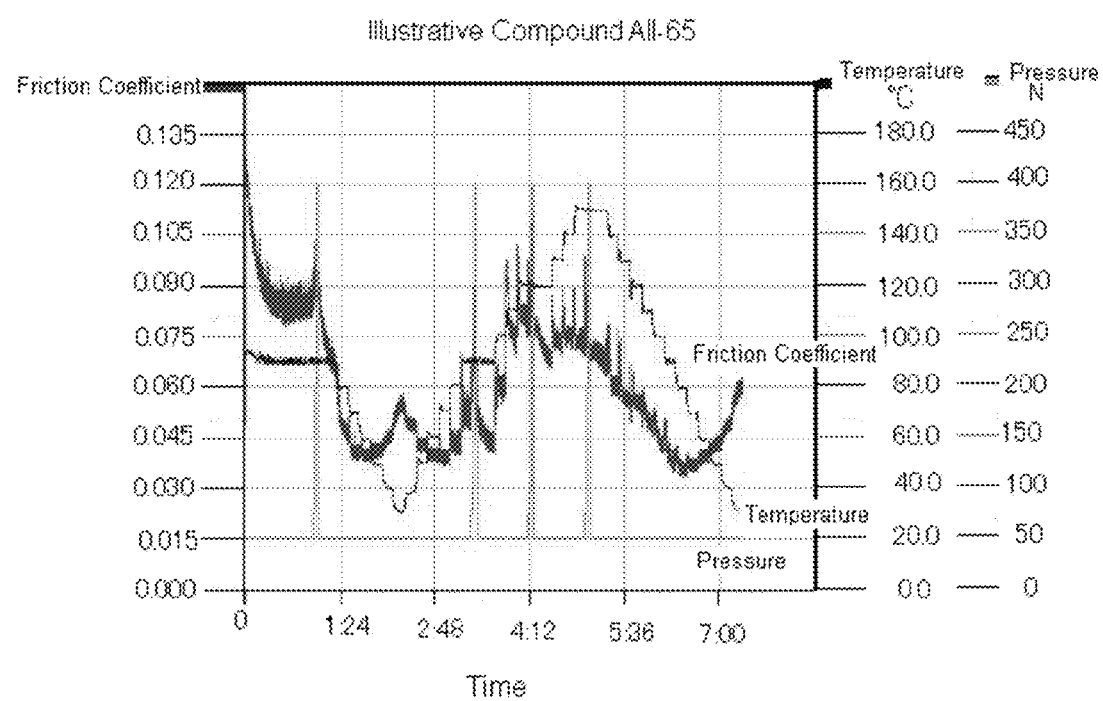
FIG. 3 is a graph showing the results of Test Example 1 of Illustrative Compounds AII-65.
Figure 4:
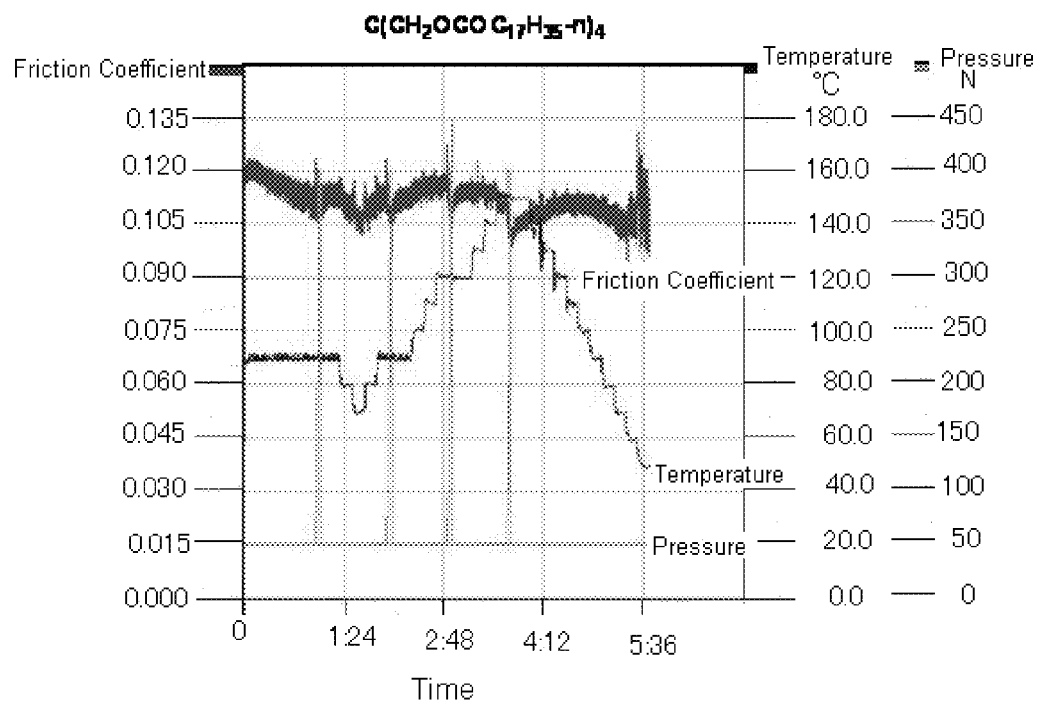
FIG. 4 is a graph showing the results of Test Example 1 of Comparative Compounds C-1 and C-2.
Figure 4:
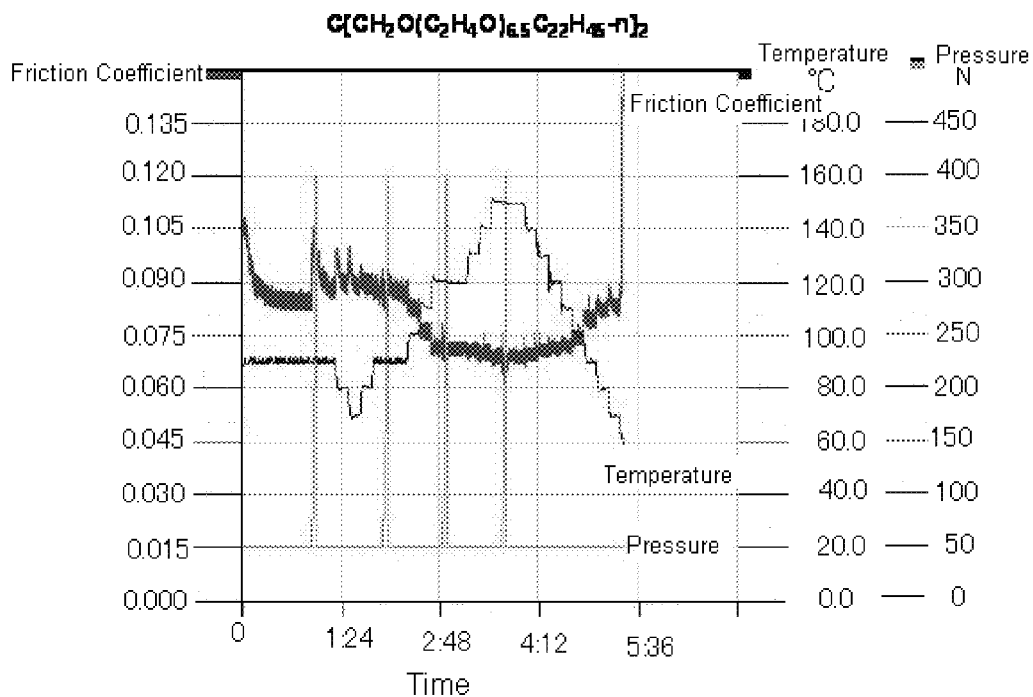
Figure 5:
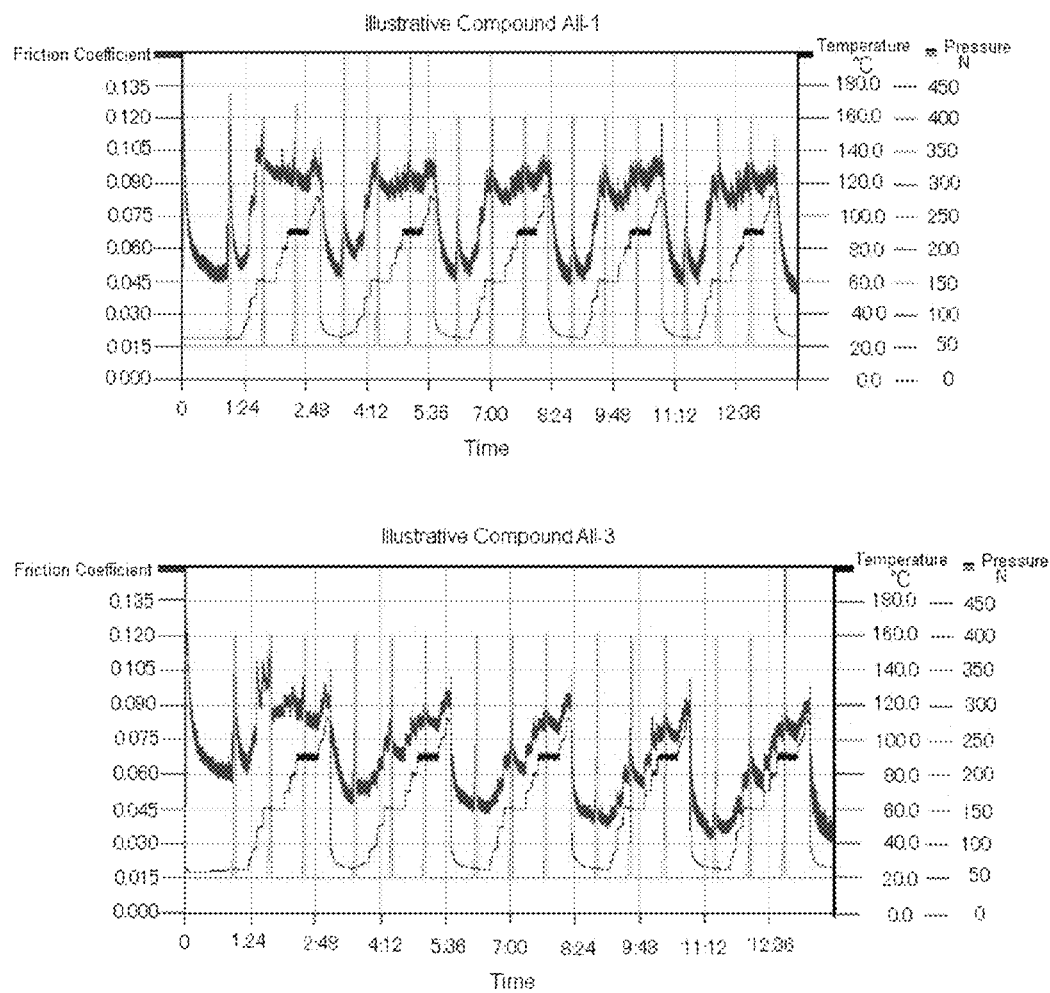
FIG. 5 is a graph showing the results of Test Example 2 of the compositions containing Illustrative Compounds AII-1 and AII-3, respectively.
Figure 6:
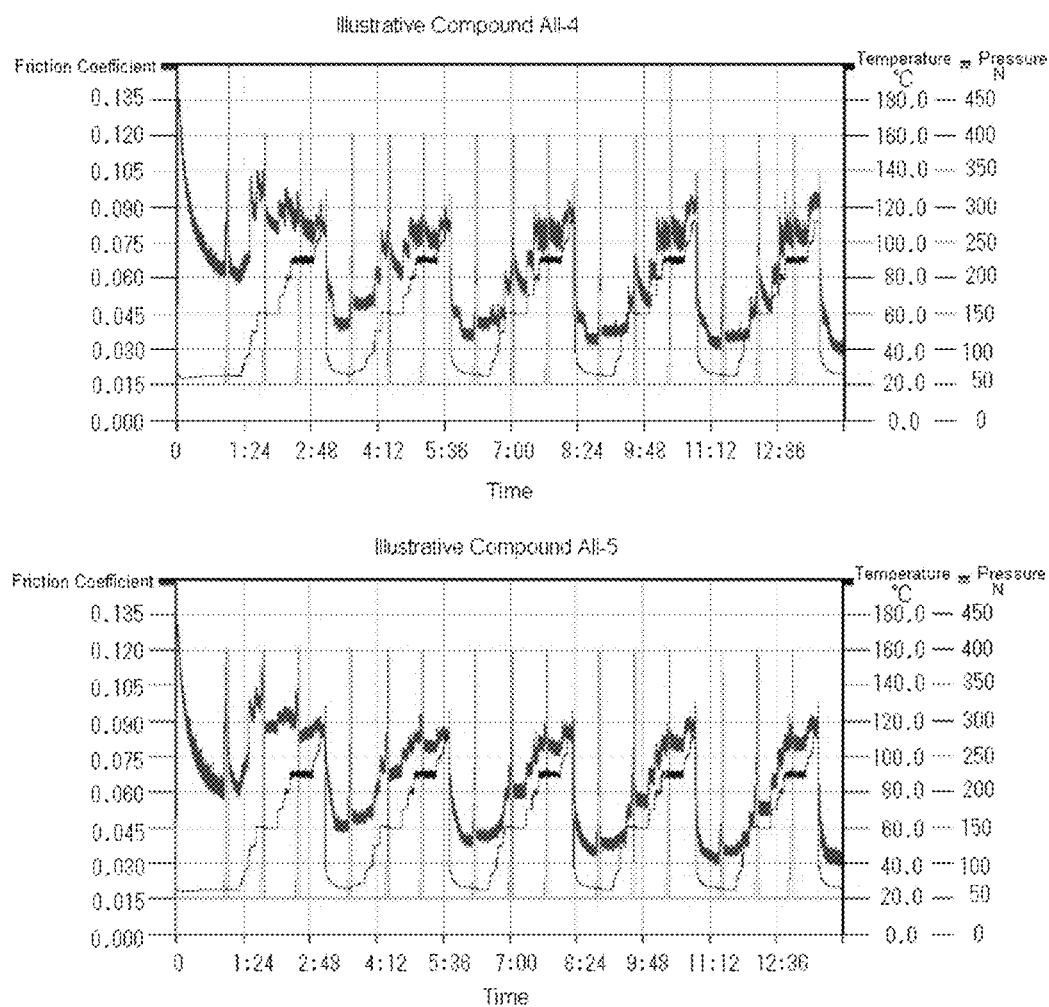
FIG. 6 is a graph showing the results of Test Example 2 of the compositions containing Illustrative Compounds AII-4 and AII-5, respectively.
Figure 7:
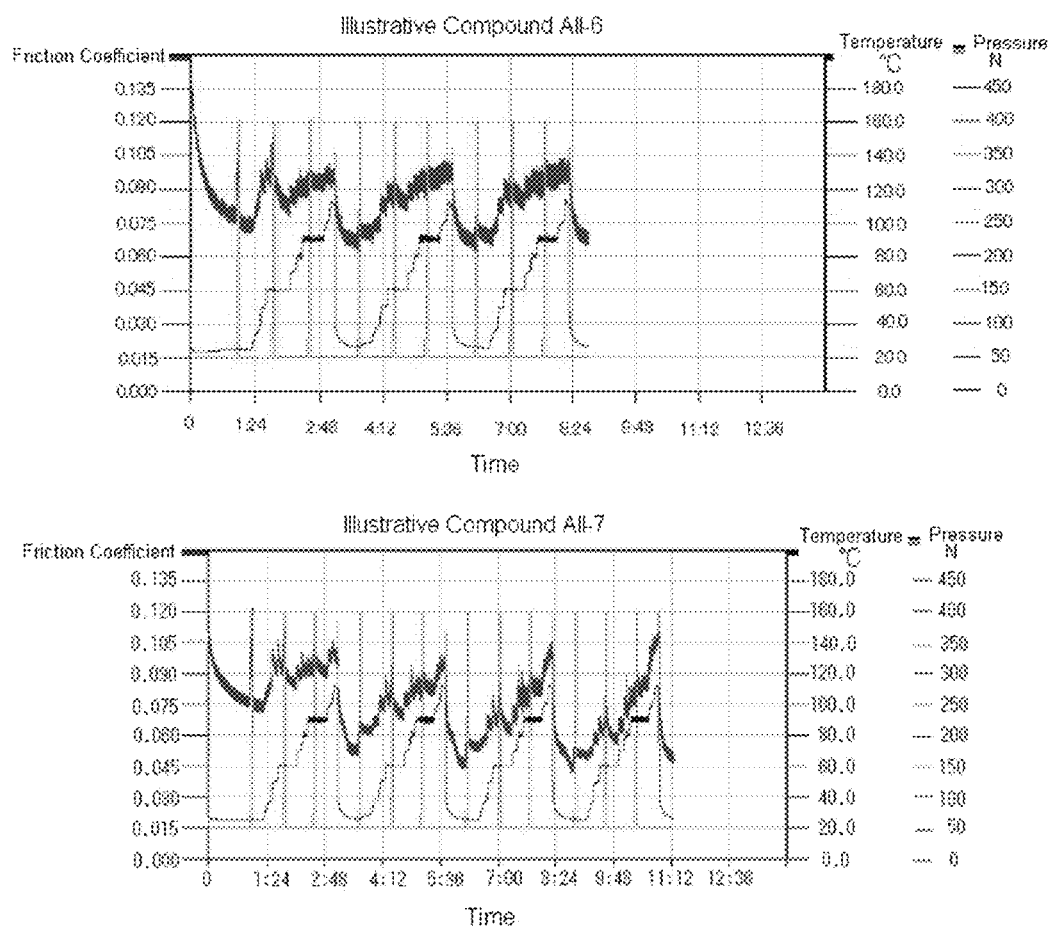
FIG. 7 is a graph showing the results of Test Example 2 of the compositions containing Illustrative Compounds AII-6 and AII-7, respectively.
Figure 8:
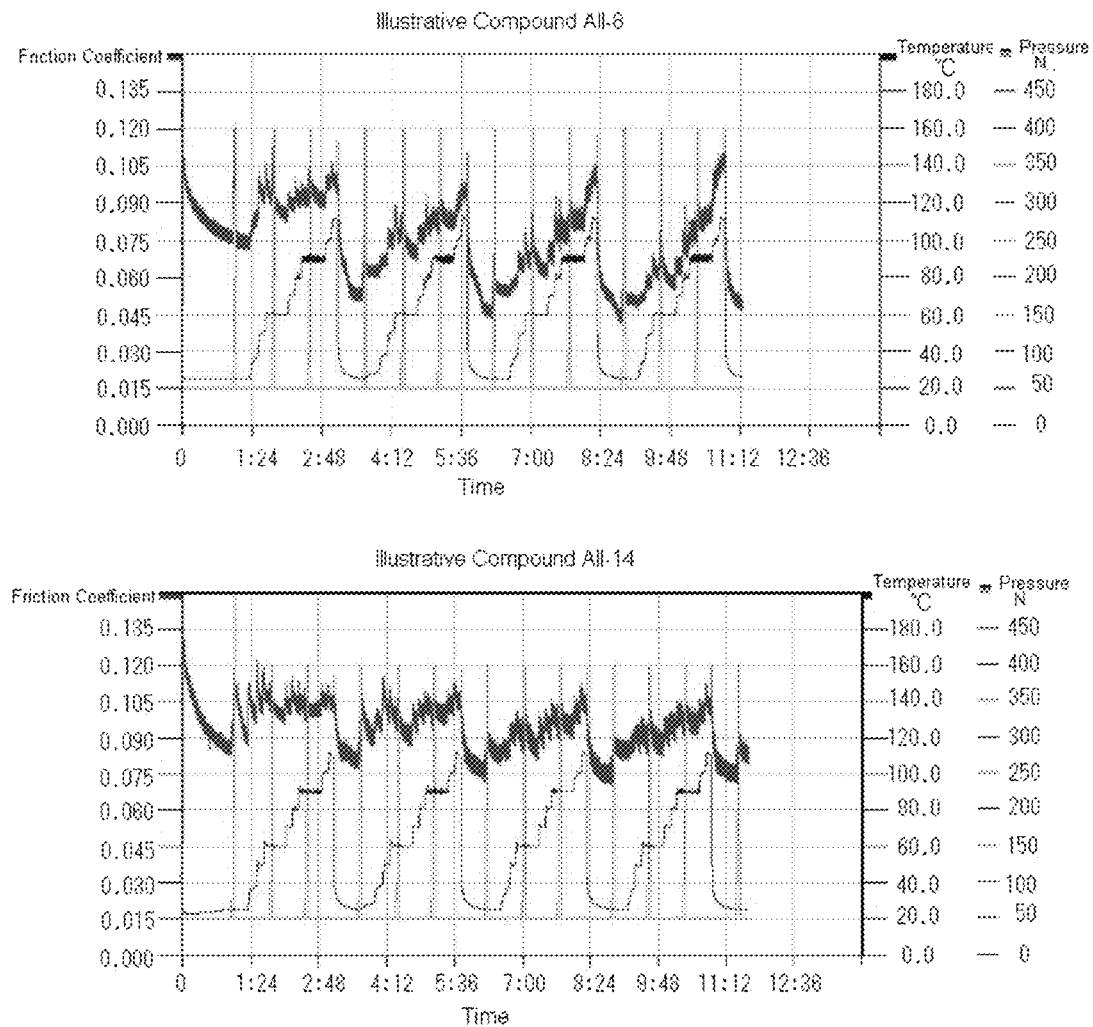
FIG. 8 is a graph showing the results of Test Example 2 of the compositions containing Illustrative Compounds AII-8 and AII-14, respectively.
Figure 9:
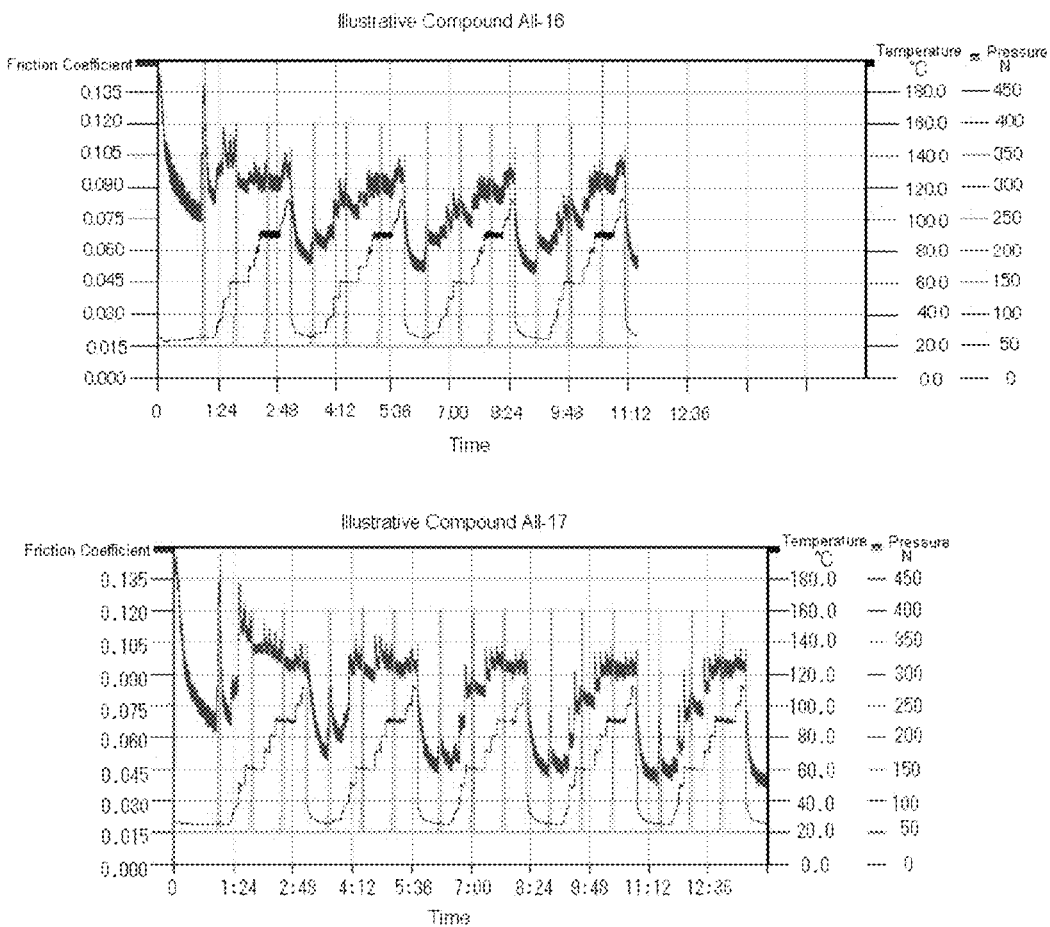
FIG. 9 is a graph showing the results of Test Example 2 of the compositions containing Illustrative Compounds AII-16 and AII-17, respectively.
Figure 10:
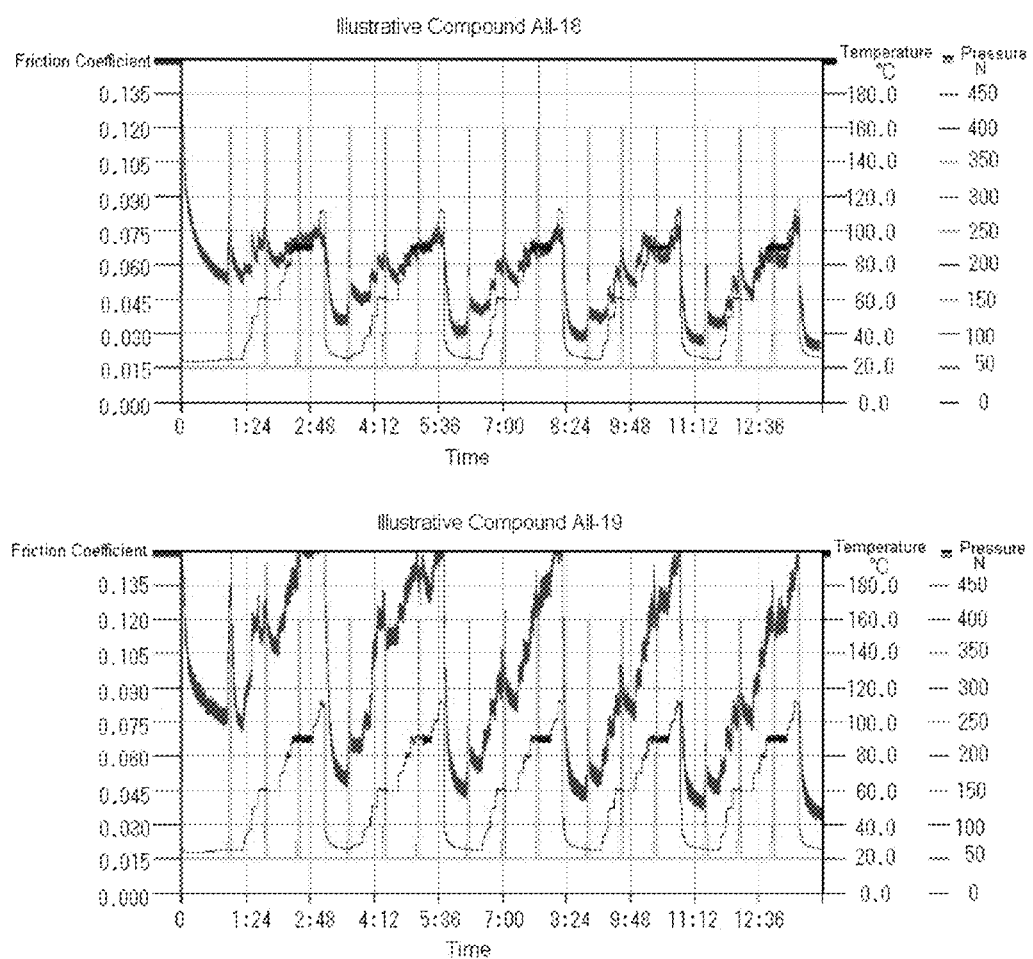
FIG. 10 is a graph showing the results of Test Example 2 of the compositions containing Illustrative Compounds AII-18 and AII-19, respectively.
Figure 11:
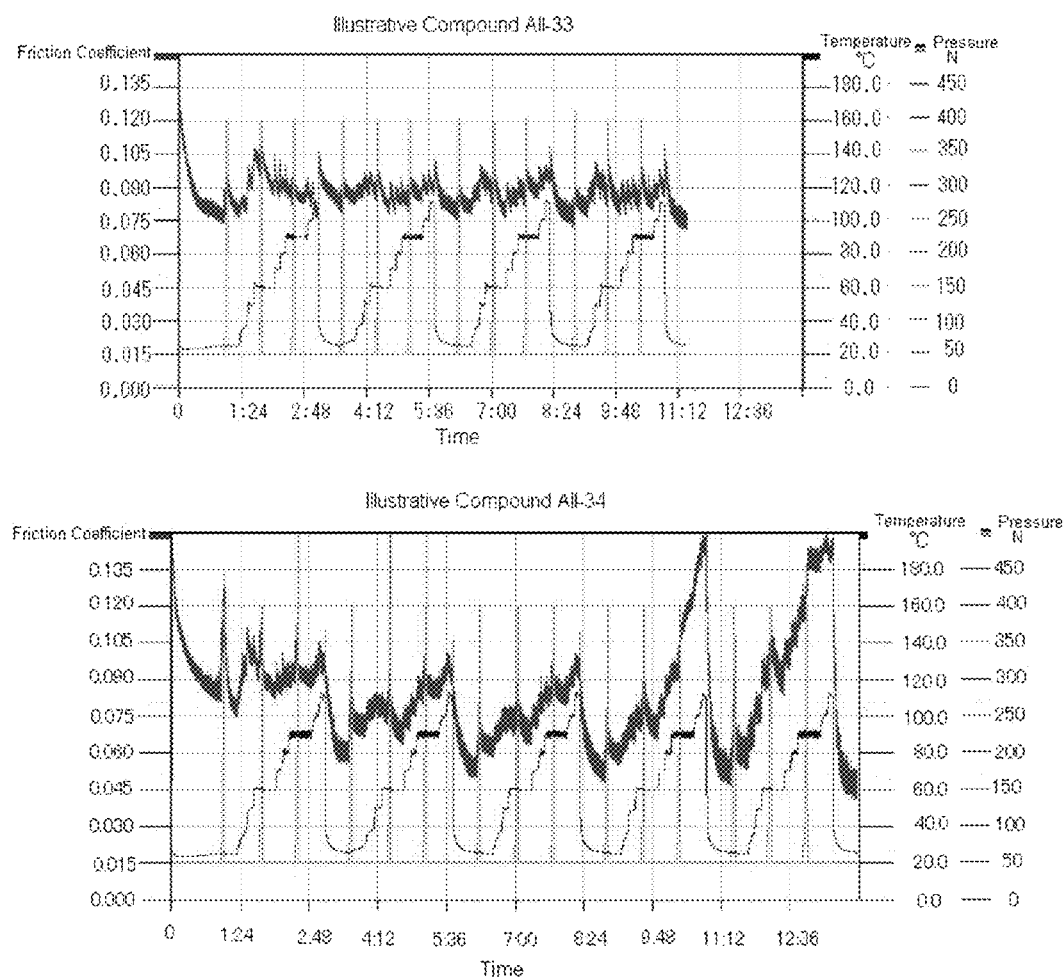
FIG. 11 is a graph showing the results of Test Example 2 of the compositions containing Illustrative Compounds AII-33 and AII-34, respectively.
Figure 12:
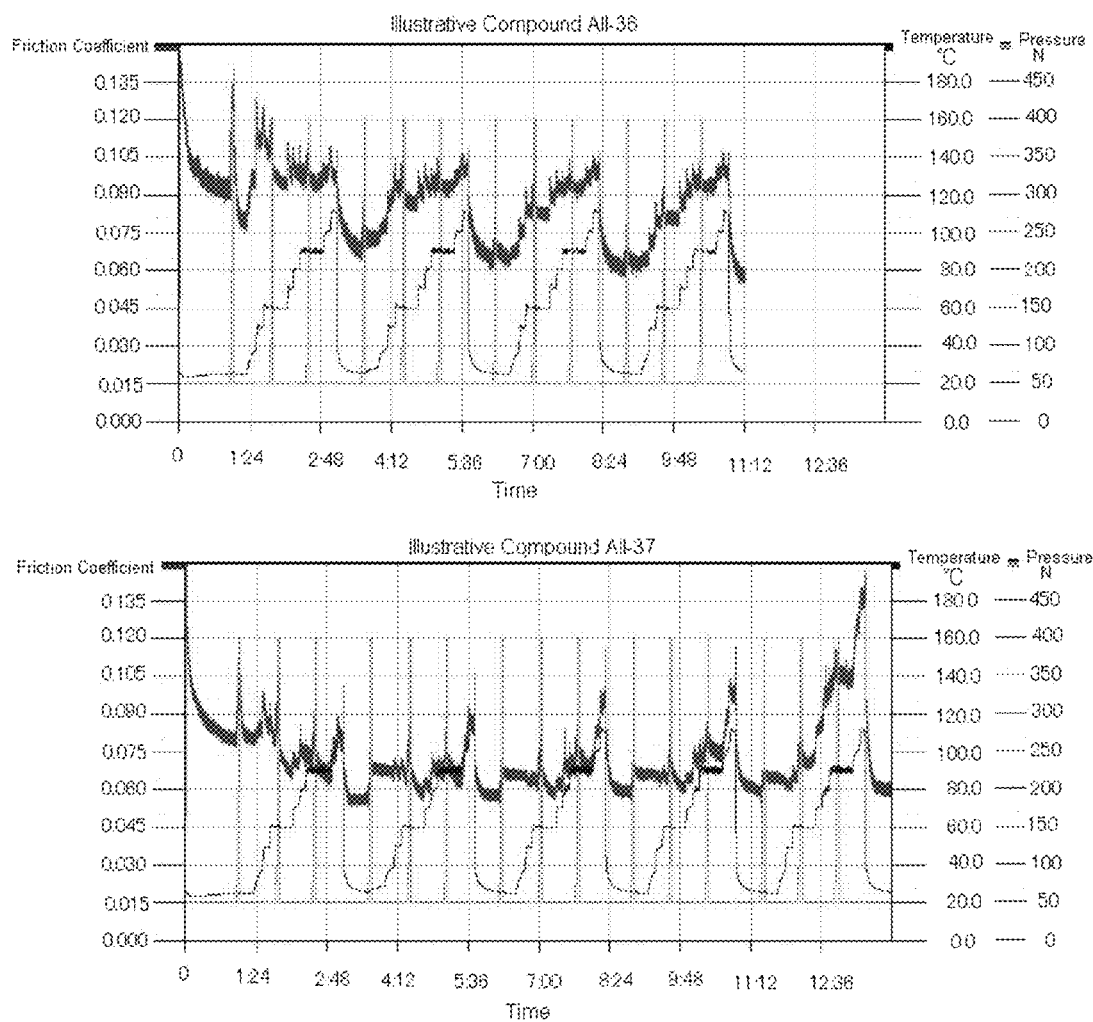
FIG. 12 is a graph showing the results of Test Example 2 of the compositions containing Illustrative Compounds AII-36 and AII-37, respectively.
Figure 13:
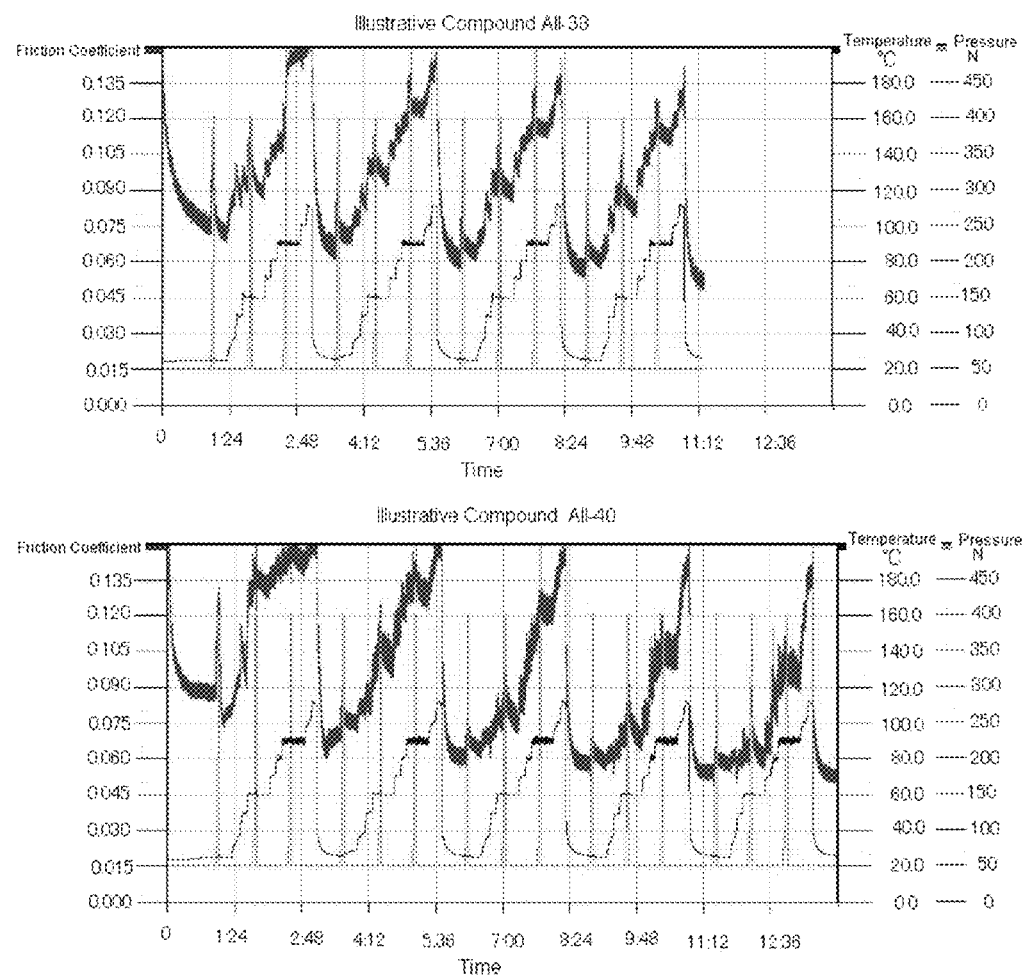
FIG. 13 is a graph showing the results of Test Example 2 of the compositions containing Illustrative Compounds AII-38 and AII-40, respectively.
Figure 14:
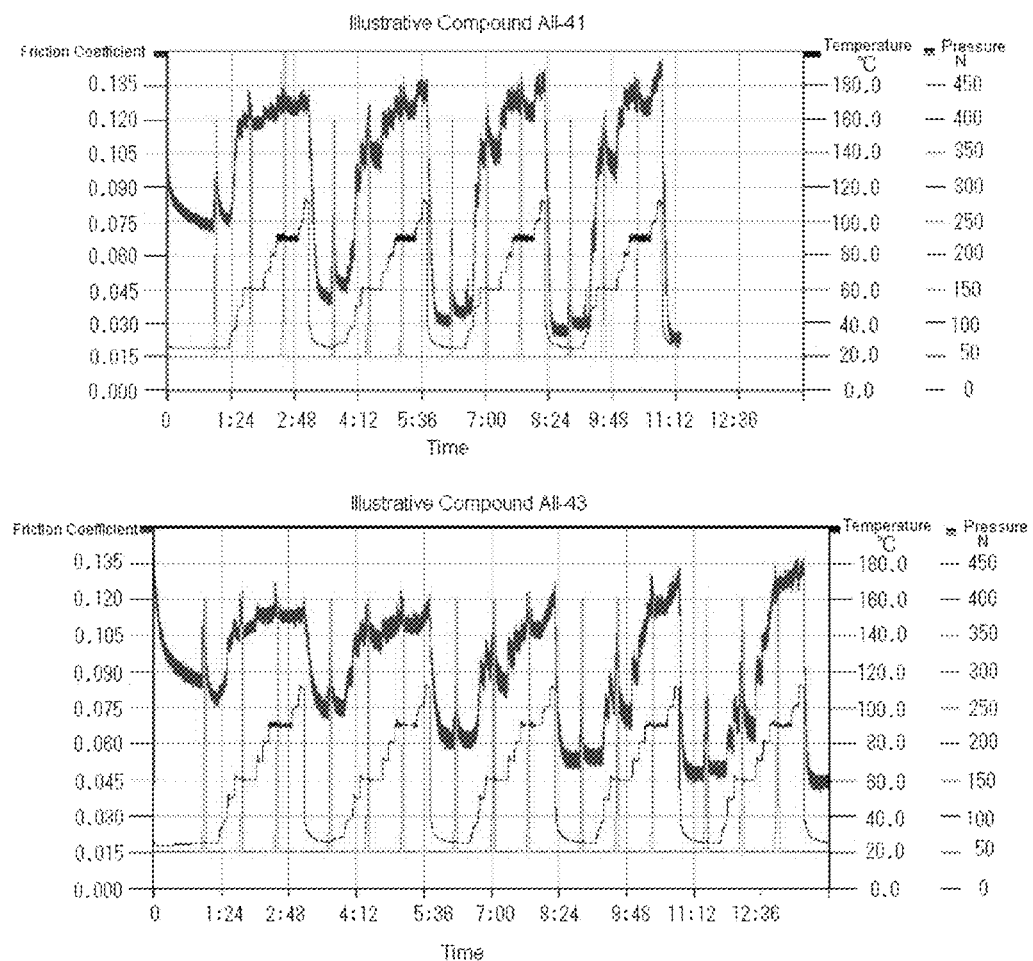
FIG. 14 is a graph showing the results of Test Example 2 of the compositions containing Illustrative Compounds AII-41 and AII-43, respectively.
Figure 15:
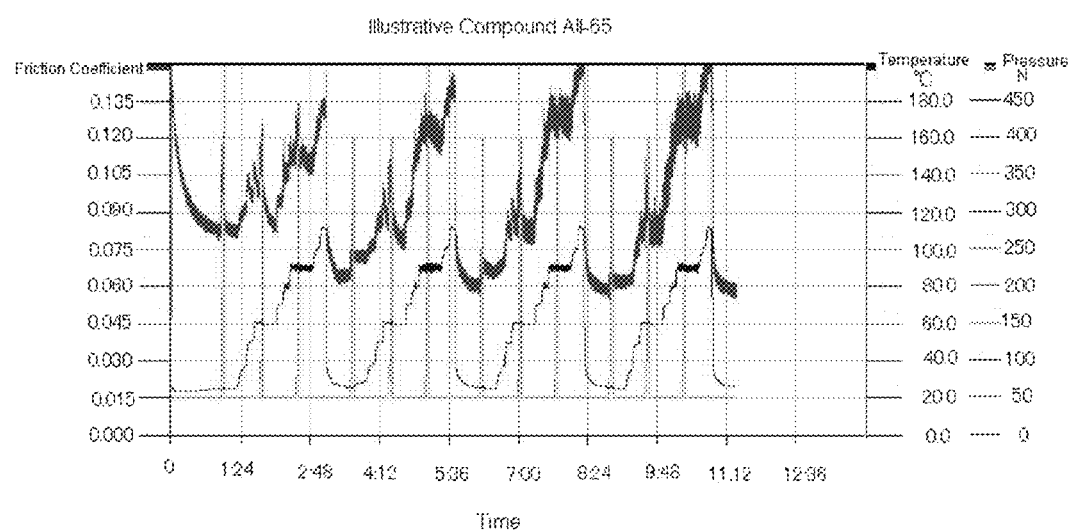
FIG. 15 is a graph showing the results of Test Example 2 of the composition containing Illustrative Compounds AII-65.
Figure 16:
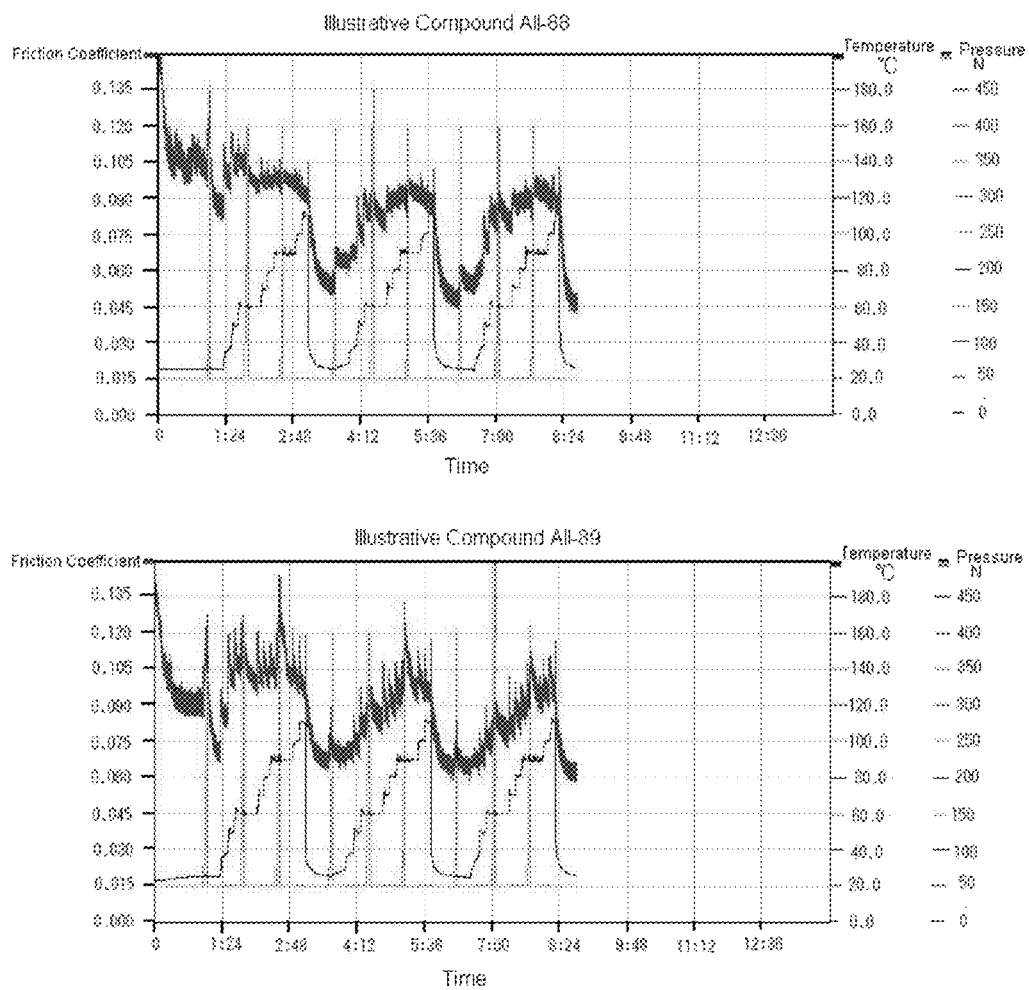
FIG. 16 is a graph showing the results of Test Example 2 of the composition containing Illustrative Compounds AII-88 and AII-89, respectively.
Figure 17:
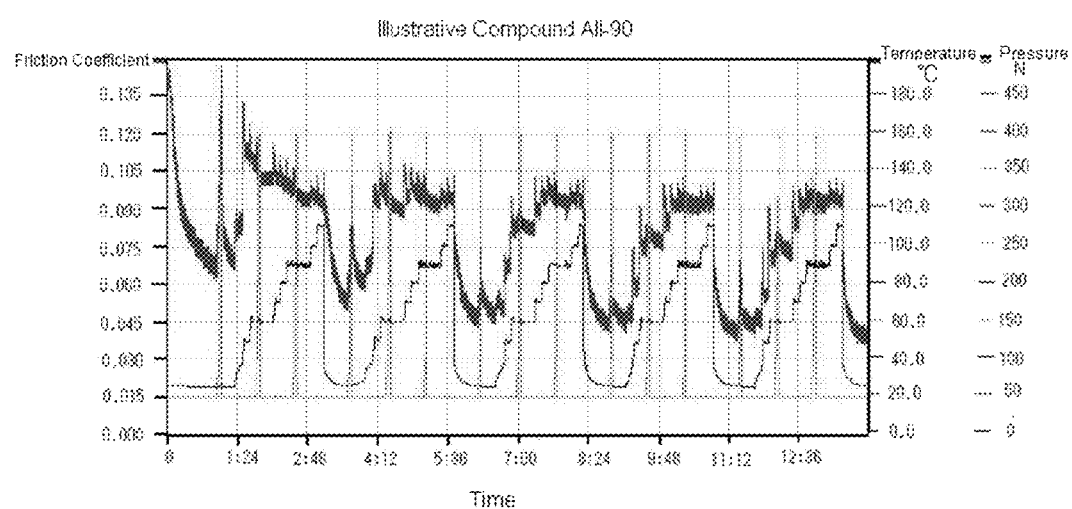
FIG. 17 is a graph showing the results of Test Example 2 of the composition containing Illustrative Compounds AII-90.
Figure 18:
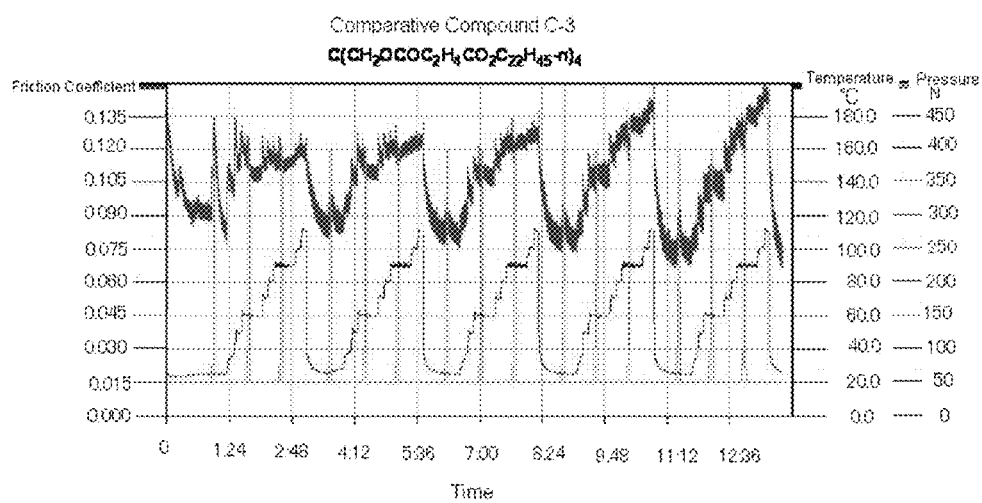
FIG. 18 is a graph showing the results of Test Example 2 of the compositions containing Comparative Compounds C-3 and C-6, respectively.
Figure 18:
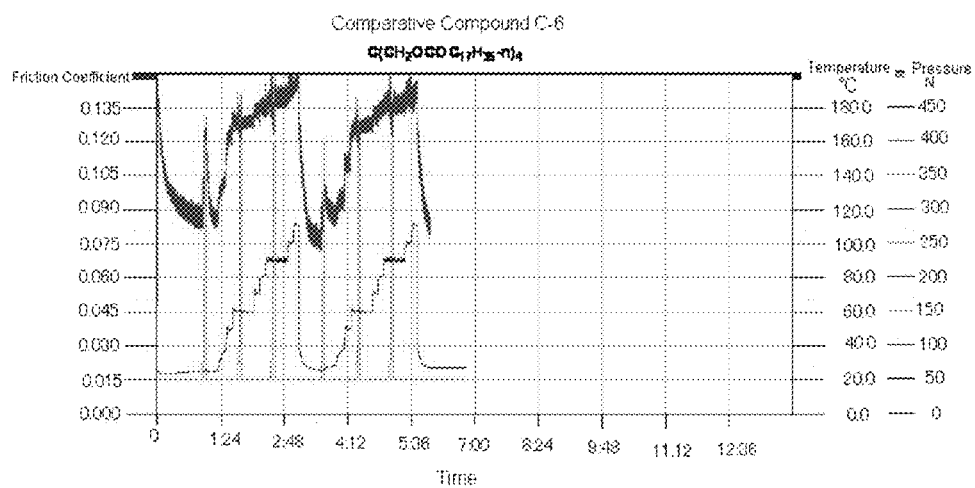
Figure 19:
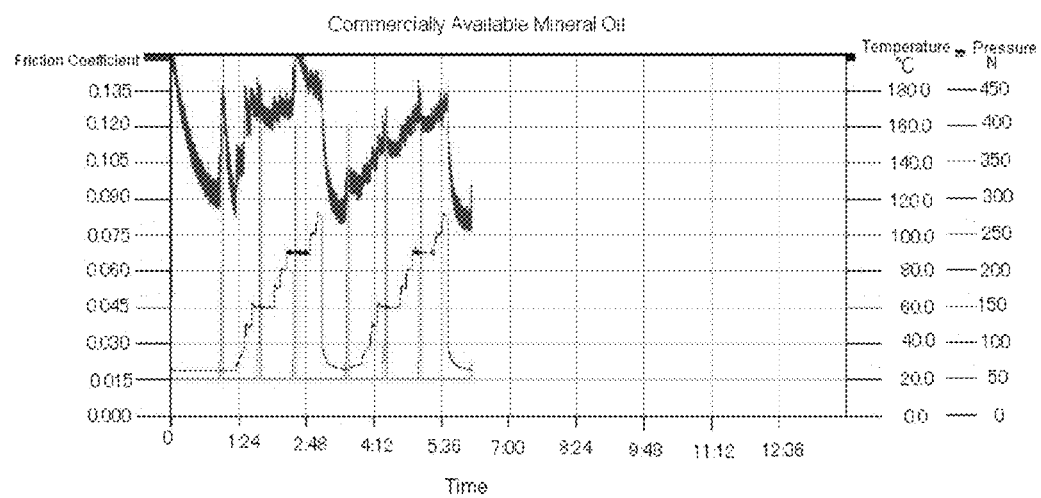
FIG. 19 is a graph showing the results of Test Example 2 of a commercially available mineral oil.
Figure 20:
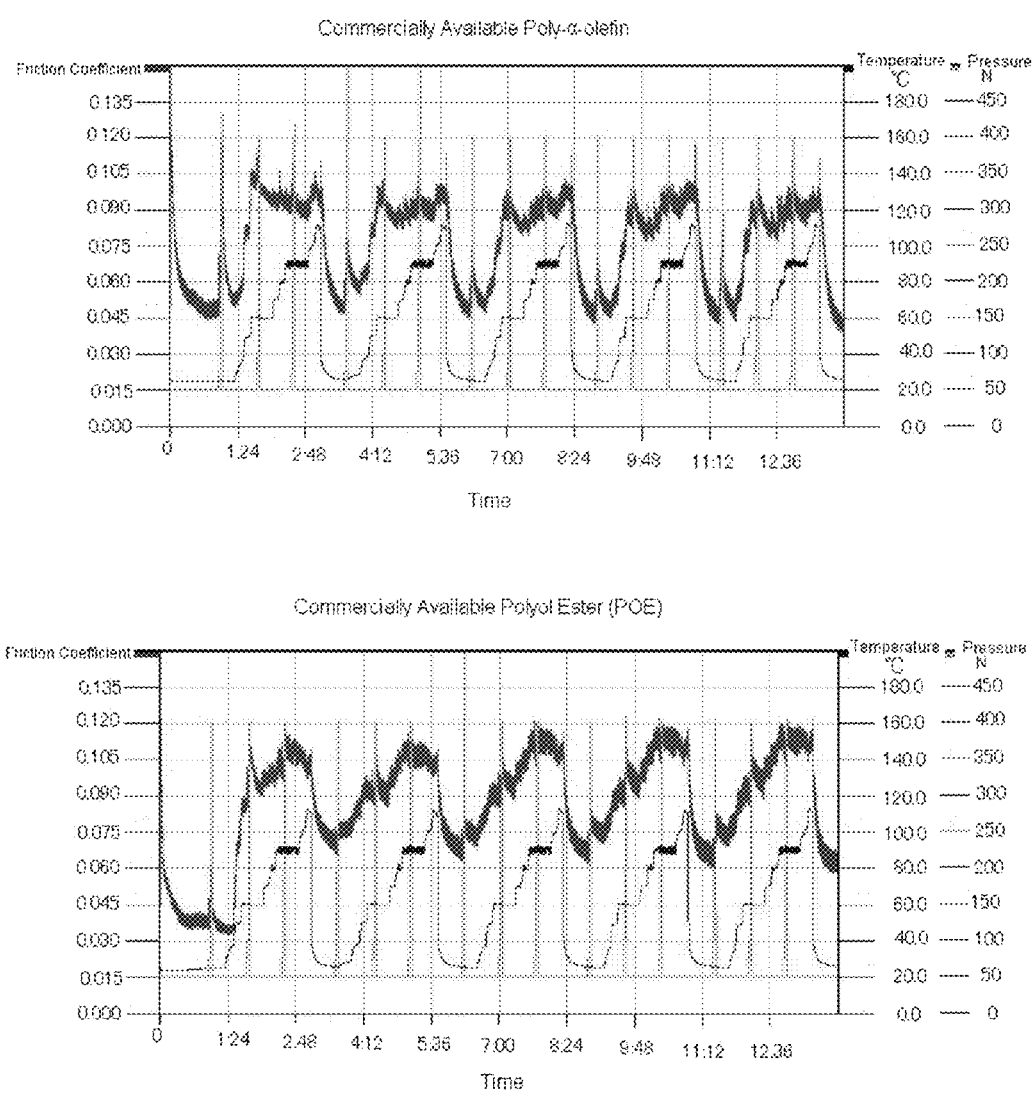
FIG. 20 is a graph showing the results of Text Example 3 of the compositions prepared using Illustrative Compound AII-4 and a commercially available poly-α-olefin and a polyol ester, respectively.
Figure 21:
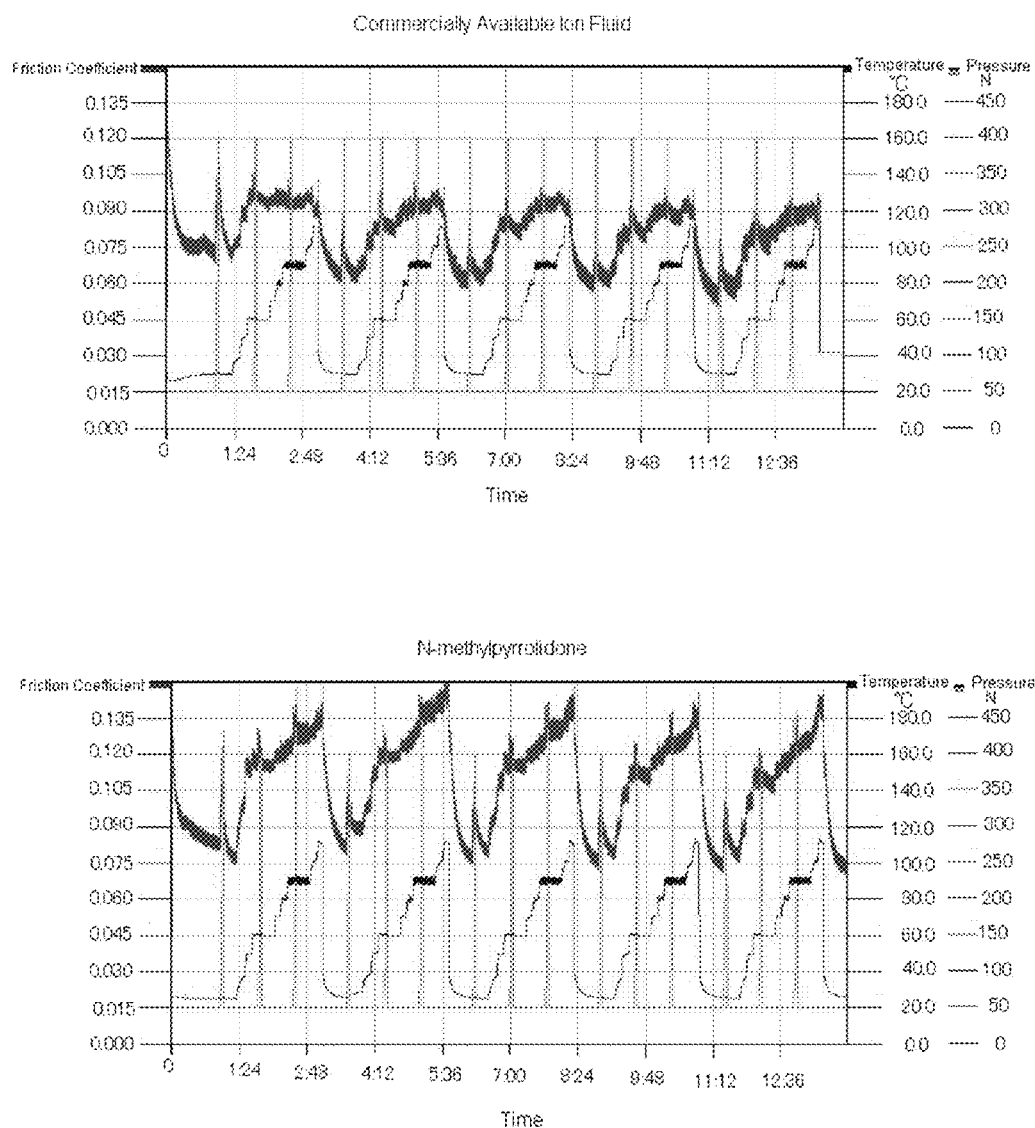
FIG. 21 is a graph showing the results of Text Example 3 of the compositions prepared using Illustrative Compound AII-4 and a commercially available ion fluid and N-methylpyrrolidone, respectively.
Figure 22:
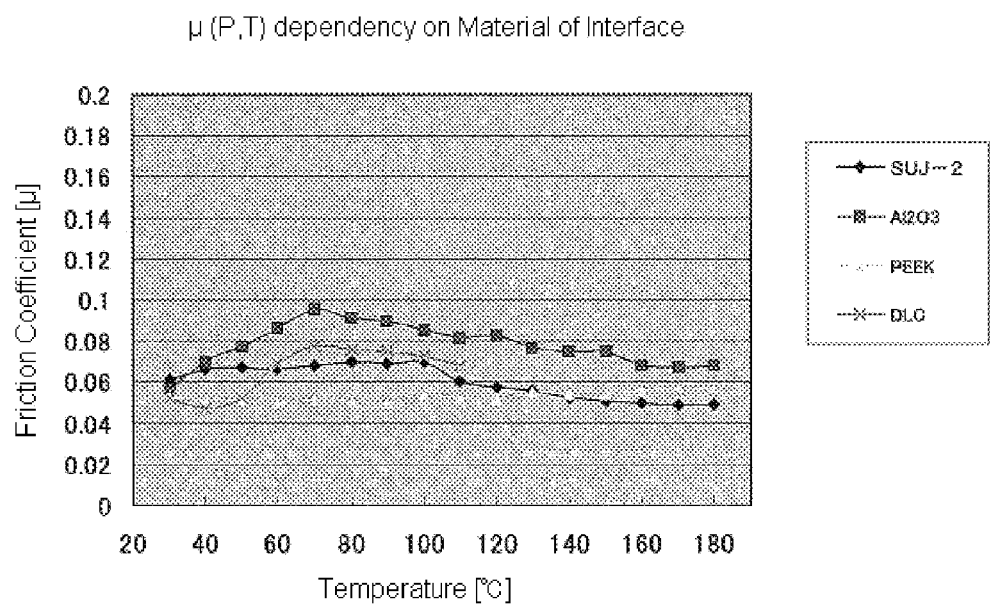
FIG. 22 is a graph showing the results of Test Example 4 of the composition containing Illustrative Compound AII-1.
Figure 23:
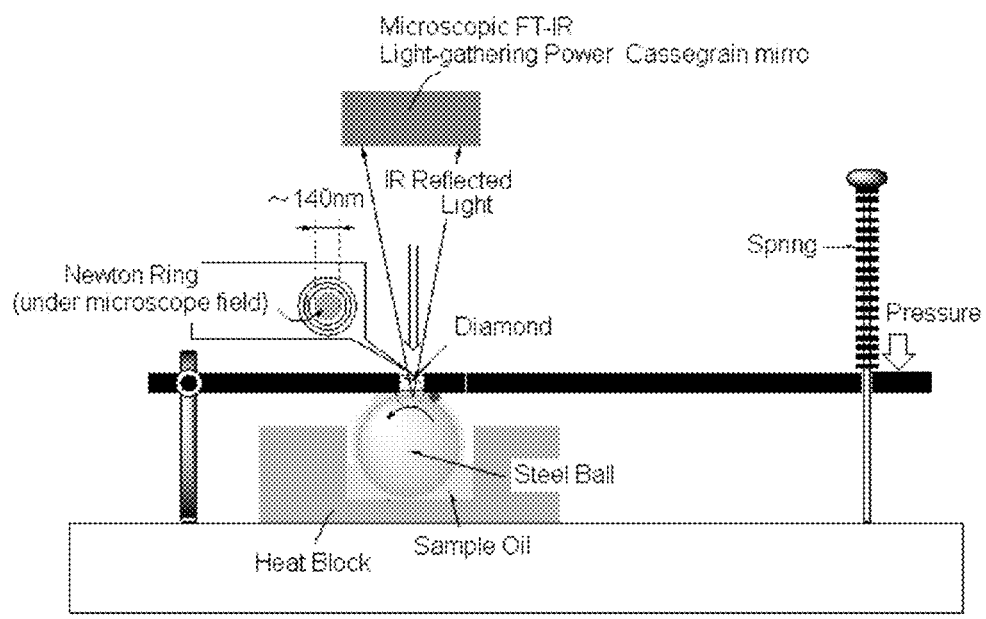
FIG. 23 is a diagrammatic view of the apparatus used in Test Example 5.
Figure 24:
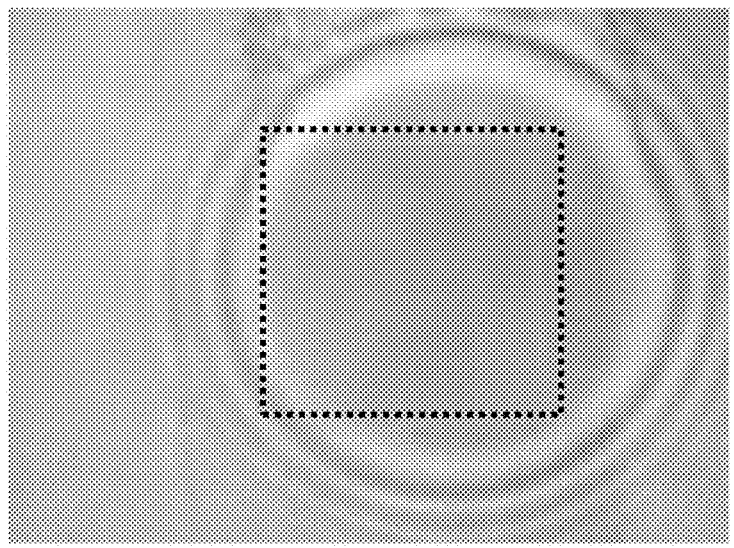
FIG. 24 is a microscopic photograph of the Newtonian ring observed in Test Example 5.
Figure 25:
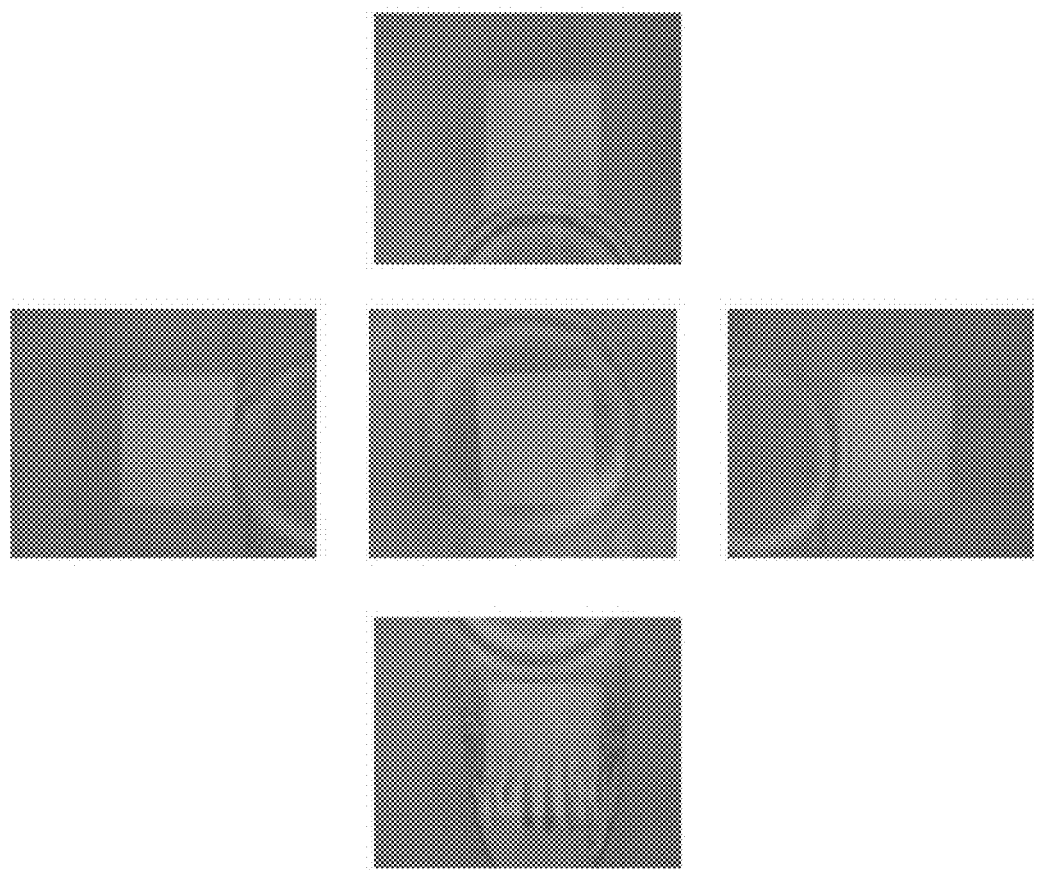
FIG. 25 is a microscopic photograph of the Newtonian ring observed in Test Example 5.
Figure 26:
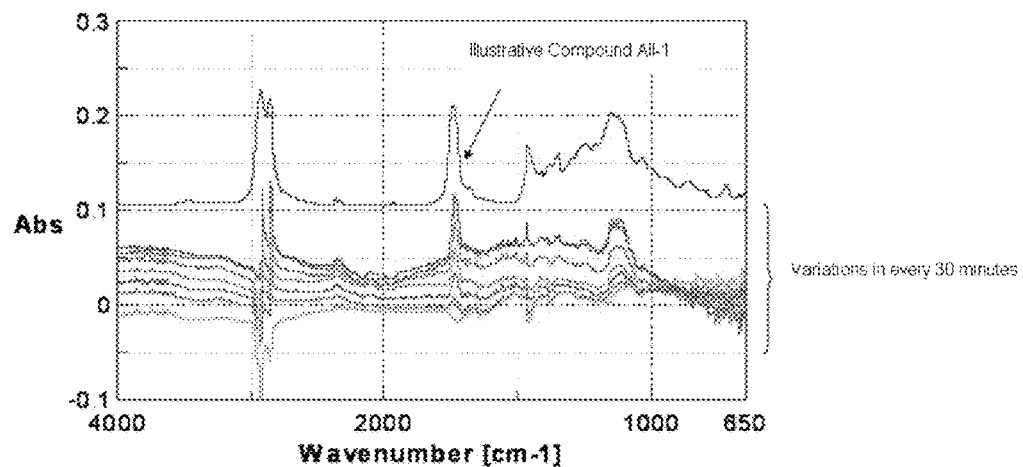
FIG. 26 is an IR spectrum measured in Test Example 5.
Figure 27:
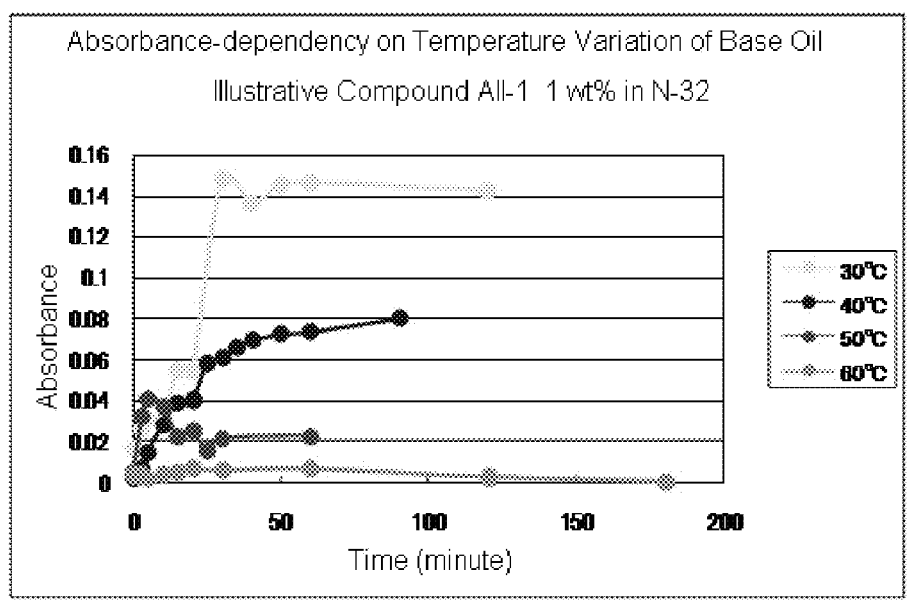
FIG. 27 is a graph showing a fluctuation of an absorbance of an IR spectrum measured in Test Example 5 relative to a temperature change.
Figure 28:
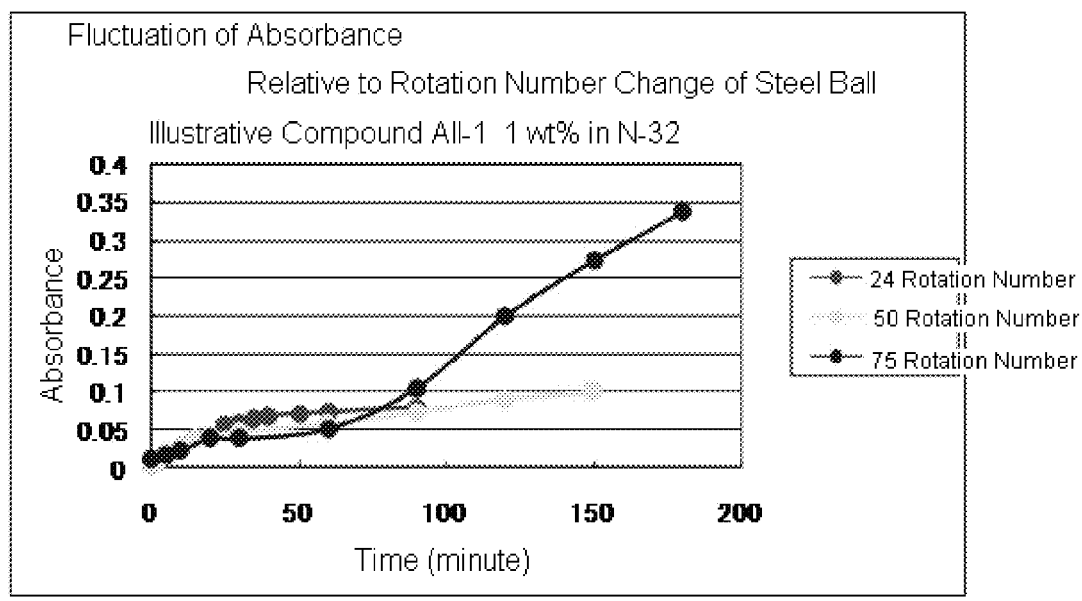
FIG. 28 is a graph showing a fluctuation of an absorbance of an IR spectrum measured in Test Example 5 relative to the rotation number change of a steel ball.

The invention claimed is:

1. A compound represented by following formula (Z):

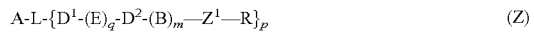

wherein

A is a group represented by the following formula (A1) or (AIII);

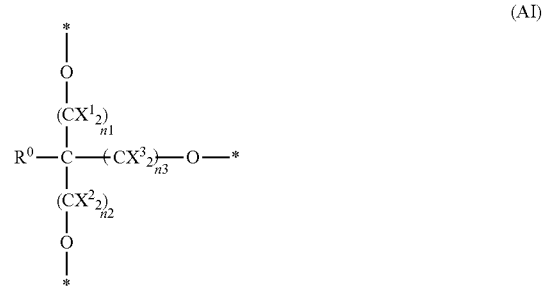

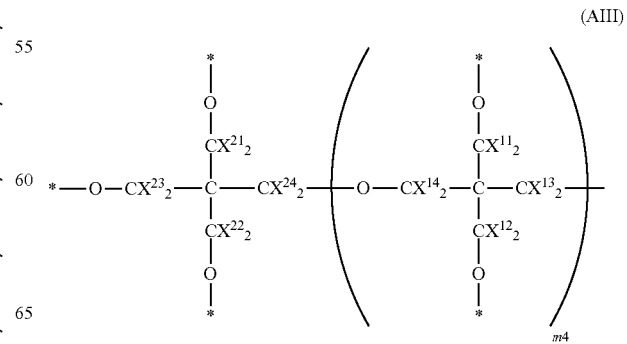

-continued

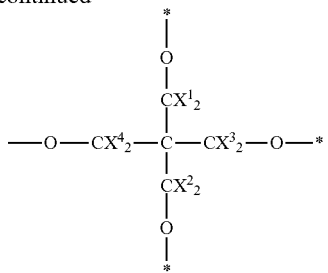

wherein
* means a bonding site to $-L-D^1-(E)_q-D_2-(B)_m-Z^1-R$; C represents a carbon atom; $R^0$ represents a hydrogen atom or a substituent; each of $X^1$ to $X^4$, $X^{11}$ to $X^{14}$ and $X^{21}$ to $X^{24}$ represents a hydrogen atom or a halogen atom and may be the same as or different from every other; each of n1 to n3 represents an integer of from 0 to 5; and m4 represents an integer of from 0 to 2;

L represents a single bond, an oxy group, a substituted or non-substituted oxymethylene group represented by following formula (A-a), or a substituted or nonsubstituted oxyethyleneoxy group represented by following formula (A-b):

—(O—C(Alk)$_2$)- (A-a)

—(O—C(Alk)$_2$C(Alk)$_2$O)— (A-b)

Alk represents a hydrogen atom, a $C_1$-$C_6$ alkyl group or a cycloalkyl group;

p represents an integer of 3 or more;

$D^1$ represents a carbonyl group (—C(=O)—) or a sulfonyl group (—S(=O)$_2$—), and each $D^1$ may be the same as or different from every other $D^1$;

$D^2$ represents a carbonyl group (—C(=O)—), a sulfonyl group (—S(=O)$_2$—), a carboxyl group (—C(=O)O—), a sulfonyloxyl group (—S(=O)$_2$O—), a carbamoyl group (—C(=O)N(Alk)-) or a sulfamoyl group (—S(=O)$_2$N(Alk)-), and each $D^2$ may be the same as or different from every other $D^2$, wherein Alk represents a hydrogen atom, a $C_1$-$C_6$ alkyl group or a cycloalkyl group;

E represents a substituted or nonsubstituted alkylene group, cycloalkylene group, alkenylene group, alkynylene group or arylene group, a divalent heterocyclic aromatic ring group or heterocyclic non-aromatic ring group, a divalent group selected among an imino group, an alkylimino group, an oxy group, a sulfide group, a sulfenyl group, a sulfonyl group, a phosphoryl group and an alkyl-substituted silyl group, or a divalent group composed of a combination of two or more of these groups; q represents an integer of 0 or more; and when q is 2 or more, each E may be the same as or different from every other E;

R represents a hydrogen atom, a substituted or non-substituted $C_8$ or longer alkyl group, a perfluoroalkyl group or a trialkylsilyl group, and each R may be the same as or different from every other R;

B varies depending upon R;

in the case where R represents a hydrogen atom or a substituted or non-substituted $C_8$ or longer alkyl group, B represents a substituted or non-substituted oxyethylene group or a substituted or non-substituted oxypropylene group; plural Bs connecting to each other may be the same as or different from each other; and m represents a natural number of 1 or more;

in the case where R represents a perfluoroalkyl group, B represents an oxyperfluoromethylene group, an oxyperfluoroethylene group or an optionally branched oxyperfluoropropylene group; plural Bs connecting to each other may be the same as or different from each other; and m represents a natural number of 1 or more;

in the case where R represents a trialkylsilyl group, B represents a dialkylsiloxy group in which the alkyl group is selected among a methyl group, an ethyl group and an optionally branched propyl group; each B may be the same as or different from every other B; plural Bs connecting to each other may be the same as or different from each other; and m represents a natural number of 1 or more; and $Z^1$ represents a single bond, a divalent group selected among a carbonyl group, a sulfonyl group, a phosphoryl group, an oxy group, a substituted or non-substituted amino group, a sulfide group, an alkenylene group, an alkynylene group and an arylene group or a divalent group composed of a combination of two or more of these groups.

2. The compound according to claim 1, wherein in the formula (Z), each —(B)$_m$—$Z^1$—R is a group represented by following formula (ECa), and each —(B)$_m$—$Z^1$—R may be the same as or different from every other —(B)$_m$—$Z^1$—R:

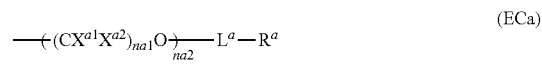

wherein
in the formula (ECa), C represents a carbon atom; O represents an oxygen atom; $R^a$ corresponding to R in the formula (Z) represents a substituted or non-substituted $C_8$ or longer alkyl group; $L^a$ corresponding to $Z^1$ in the formula (Z) represents a single bond or a divalent connecting group; each of $X^{a1}$ and $X^{a2}$ represents a hydrogen atom or a halogen atom; na1 represents an integer of from 1 to 4; when na1 is 2 or more, plural $X^{a1}$s and $X^{a2}$s may be the same as or different from each other; and na2 represents a number of from 1 to 35.

3. The compound according to claim 2, wherein in formula (Z), $L^a$ corresponding to $Z^1$ is a single bond or a divalent connecting group composed of a combination of one or more members selected among a carbonyl group, a sulfonyl group, a phosphoryl group, an oxy group, a substituted or non-substituted amino group, a thio group, an alkylene group, an alkenylene group, an alkynylene group and an arylene group.

4. The compound according to claim 1, wherein in formula (Z), each —(B)$_m$—$Z^1$—R is a group represented by following formula (ECb), and each —(B)$_m$—$Z^1$—R may be the same as or different from every other —(B)$_m$—$Z^1$—R:

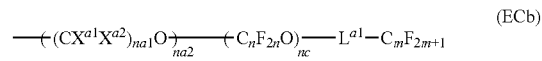

wherein
in the formula (ECb), C represents a carbon atom; O represents an oxygen atom; each of $X^{a1}$ and $X^{a2}$ represents a hydrogen atom or a halogen atom; na1 represents an integer of from 1 to 4; when na1 is 2 or more, plural $X^{a1}$s and $X^{a2}$s may be the same as or different from each other; $L^{a1}$ corresponding to $Z^1$ in the formula (Z) represents a single bond; na2 represents a number of from 0 to 2; nc represents a number of from 1 to 10; m represents a number of from 1 to 12; and n represents a number of from 1 to 3.

5. The compound according to claim 1, wherein in formula (Z), each —$(B)_m$—$Z^1$—R is a group represented by following formula (ECc), and each —$(B)_m$—$Z^1$—R may be the same as or different from every other —$(B)_m$—$Z^1$—R:

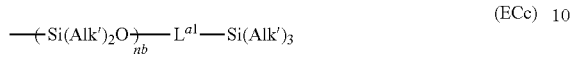

(ECc)

wherein
in formula (ECc), the same symbols as those in formula (ECa) according to claim 4 are synonymous, respectively; each Alk' may be the same as or different from every other Alk' and represents a $C_1$-$C_4$ alkyl group; $L^{a1}$ corresponding to $Z^1$ in the formula (Z) represents a single bond; and nb represents a number of from 1 to 10.

* * * * *